United States Patent [19]
Palkowitz

[11] Patent Number: 5,977,093
[45] Date of Patent: Nov. 2, 1999

[54] BENZOTHIOPHENE COMPOUNDS, INTERMEDIATES, COMPOSITIONS, AND METHODS

[75] Inventor: Alan David Palkowitz, Carmel, Ind.

[73] Assignee: Eli Lilly and Company, Indianapolis, Ind.

[21] Appl. No.: 08/552,565

[22] Filed: Nov. 3, 1995

Related U.S. Application Data

[60] Continuation-in-part of application No. 08/470,510, Jun. 6, 1995, abandoned, which is a division of application No. 08/396,401, Feb. 28, 1995, Pat. No. 5,510,357.

[51] Int. Cl.[6] .................. A61K 31/56; A61K 31/445; C07D 409/12
[52] U.S. Cl. .................. 514/171; 514/212; 514/233.5; 514/320; 514/324; 514/422; 514/469; 540/596; 544/153; 546/202; 548/525; 549/49
[58] Field of Search .................. 540/596; 564/153; 546/202; 548/525; 549/49; 514/324, 171, 233.5, 312, 320, 422, 469

[56] References Cited

U.S. PATENT DOCUMENTS

| | | | |
|---|---|---|---|
| 3,293,263 | 12/1966 | Lednicer | 546/205 |
| 3,320,271 | 5/1967 | Lednicer | 548/570 |
| 3,394,125 | 7/1968 | Crenshaw | 548/525 |
| 3,413,305 | 11/1968 | Crenshaw | 548/525 |
| 3,862,232 | 1/1975 | Lednicer | 564/324 |
| 4,117,128 | 9/1978 | Brenner | 514/212 |
| 4,133,814 | 1/1979 | Jones et al. | 546/202 |
| 4,230,862 | 10/1980 | Suarez et al. | 546/237 |
| 4,418,068 | 11/1983 | Jones | 514/320 |
| 4,910,212 | 3/1990 | Boyle et al. | 514/383 |
| 5,013,761 | 5/1991 | Beedle et al. | 514/650 |
| 5,223,510 | 6/1993 | Gubin et al. | 514/299 |
| 5,254,568 | 10/1993 | Kapil et al. | 514/320 |
| 5,384,332 | 1/1995 | Fontana | 514/648 |
| 5,488,058 | 1/1996 | Palkowitz | 514/324 |
| 5,492,922 | 2/1996 | Palkowitz | 514/324 |
| 5,510,357 | 4/1996 | Palkowitz | 514/324 |
| 5,510,498 | 4/1996 | Palkowitz | 549/52 |

FOREIGN PATENT DOCUMENTS

| | | |
|---|---|---|
| 0 124 369 | 11/1984 | European Pat. Off. . |
| 0 516 257 | 5/1992 | European Pat. Off. . |
| WO93/10113 | 5/1993 | WIPO . |
| WO93/1074 | 6/1993 | WIPO . |
| WO95/10513 | 4/1995 | WIPO . |

OTHER PUBLICATIONS

Sitruk–Ware, R. "Menopause which progestin to use . . . " BA 85:051565, 1987.
Robison et al., "Reveral of the antitumor effects of tamoxifen by progesterone . . . " BA 85:006817, 1987.
Jeng et al. "Estrogenic potention of ptogestins . . . " Can. Res. v.52, p. 6537–46, 1992.
Christman et al. "Chemotherapy of metastatic breast cancer in the elderly . . . " AMA abstract, 1992.
Need et al. "Effects of nandrolone decanoate on forearm mineral density and calcium metabolism in osteoporotic postmenopausal women" index Medicus 87:01037, 1987.
Crenshaw, R. R., et al., *J. Med. Chem.*, 14(12) :1185–1190 (1971).
Durani, N., et al., *Indian J. Chem.*, 22B:489–490 (1983).
Jones, C. D., et al., *J. Med. Chem.*, 35:931–938 (1992).
Lednicer, D., et al., *J. Med. Chem.*, 8:52–57 (1964).
Madesclaire, M., *Tetrahedren*, 42 (20); 5459–5495 (1986).
Trost, B.M., et al., *Tetrahedren Letters*, 22 (14) ; 1287–1290, (1981).
Drabowicz, J., et al., *Synthetic Communications*, 11 (12); 1025–1030 (1981).
Kramer, J.B., et al. *34th National Organic Symposium*, Williamsburg, VA, (Jun. 11–15, 1995).
Wyngaarden, et al., *Cecil Textbook of Medicine*, 16: 1271 (1983).

*Primary Examiner*—Ceila Chang
*Attorney, Agent, or Firm*—William R. Boudreaux

[57] ABSTRACT

A method for alleviating the symptoms of post-menopausal syndrome comprising administering to a woman in need thereof an effective amount of a compound of formula I

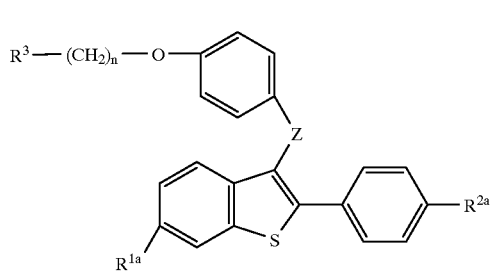

wherein
 $R^{1a}$ is —H or —$OR^{7a}$ in which $R^{7a}$ is —H or a hydroxy protecting group;
 $R^{2a}$ is —H, halo, or —$OR^{8a}$ in which $R^{8a}$ is —H or a hydroxy protecting group;
 $R^3$ is 1-piperidinyl, 1-pyrrolidino, methyl-1-pyrrolidinyl, dimethyl-1-pyrrolidino, 4-morpholino, dimethylamino, diethylamino, diisopropylamino, or 1-hexamethyleneimino;
 n is 2 or 3; and
 Z is —O— or —S—;
or a pharmaceutically acceptable salt thereof, and further comprising administering to said woman an effective amount of progestin.

11 Claims, No Drawings

BENZOTHIOPHENE COMPOUNDS, INTERMEDIATES, COMPOSITIONS, AND METHODS

This application is a continuation-in-part of application Ser. No. 08/470,510, filed June 6, 1995, now abandoned which is a divisional of application Ser. No. 08/396,401, filed Feb. 28, 1995, now U.S. Pat. No. 5,510,357.

FIELD OF THE INVENTION

This invention relates to the fields of pharmaceutical and organic chemistry and provides novel benzothiophene compounds which are useful for the treatment of the various medical indications associated with post-menopausal syndrome, and uterine fibroid disease, endometriosis, and aortal smooth muscle cell proliferation. The present invention further relates to intermediate compounds useful for preparing the pharmaceutically active compounds of the present invention, and pharmaceutical compositions.

BACKGROUND OF THE INVENTION

"Post-menopausal syndrome" is a term used to describe various pathological conditions which frequently affect women who have entered into or completed the physiological metamorphosis known as menopause. Although numerous pathologies are contemplated by the use of this term, three major effects of post-menopausal syndrome are the source of the greatest long-term medical concern:
 osteoporosis, cardiovascular effects such as hyperlipidemia, and estrogen-dependent cancer, particularly breast and uterine cancer.

Osteoporosis describes a group of diseases which arise from diverse etiologies, but which are characterized by the net loss of bone mass per unit volume. The consequence of this loss of bone mass and resulting bone fracture is the failure of the skeleton to provide adequate structural support for the body. One of the most common types of osteoporosis is that associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among post-menopausal women.

There are an estimated 25 million women in the United States, alone, who are afflicted with this disease. The results of osteoporosis are personally harmful and also account for a large economic loss due its chronicity and the need for extensive and long term support (hospitalization and nursing home care) from the disease sequelae. This is especially true in more elderly patients. Additionally, although osteoporosis is not generally thought of as a life threatening condition, a 20% to 30% mortality rate is related with hip fractures in elderly women. A large percentage of this mortality rate can be directly associated with post-menopausal osteoporosis.

The most vulnerable tissue in the bone to the effects of post-menopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This inter-connected network of trabeculae gives lateral support to the outer cortical structure and is critical to the bio-mechanical strength of the overall structure. In post-menopausal osteoporosis, it is, primarily, the net resorption and loss of the trabeculae which leads to the failure and fracture of bone. In light of the loss of the trabeculae in post-menopausal women, it is not surprising that the most common fractures are those associated with bones which are highly dependent on trabecular support, e.g., the vertebrae, the neck of the weight bearing bones such as the femur and the fore-arm. Indeed, hip fracture, collies fractures, and vertebral crush fractures are hall-marks of post-menopausal osteoporosis.

At this time, the only generally accepted method for treatment of post-menopausal osteoporosis is estrogen replacement therapy. Although therapy is generally successful, patient compliance with the therapy is low primarily because estrogen treatment frequently produces undesirable side effects.

Throughout premenopausal time, most women have less incidence of cardiovascular disease than age-matched men. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can upregulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that post-menopausal women having estrogen replacement therapy have a return of serum lipid levels to concentrations to those of the pre-menopausal state. Thus, estrogen would appear to be a reasonable treatment for this condition. However, the side-effects of estrogen replacement therapy are not acceptable to many women, thus limiting the use of this therapy. An ideal therapy for this condition would be an agent which would regulate the serum lipid level as does estrogen, but would be devoid of the side-effects and risks associated with estrogen therapy.

The third major pathology associated with post-menopausal syndrome is estrogen-dependent breast cancer and, to a lesser extent, estrogen-dependent cancers of other organs, particularly the uterus. Although such neoplasms are not solely limited to a post-menopausal women, they are more prevalent in the older, post-menopausal population. Current chemotherapy of these cancers has relied heavily on the use of anti-estrogen compounds such as, for example, tamoxifen. Although such mixed agonist-antagonists have beneficial effects in the treatment of these cancers, and the estrogenic side-effects are tolerable in acute life-threatening situations, they are not ideal. For example, these agents may have stimulatory effects on certain cancer cell populations in the uterus due to their estrogenic (agonist) properties and they may, therefore, be contraproductive in some cases. A better therapy for the treatment of these cancers would be an agent which is an anti-estrogen compound having negligible or no estrogen agonist properties on reproductive tissues.

In response to the clear need for new pharmaceutical agents which are capable of alleviating the symptoms of, inter alia, post-menopausal syndrome, the present invention provides new benzothiophene compounds, pharmaceutical compositions thereof, and methods of using such compounds for the treatment of post-menopausal syndrome and other estrogen-related pathological conditions such as those mentioned below.

Uterine fibrosis (uterine fibroid disease) is an old and ever present clinical problem which goes under a variety of names, including uterine fibroid disease, uterine hypertrophy, uterine lieomyomata, myometrial hypertrophy, fibrosis uteri, and fibrotic metritis. Essentially, uterine fibrosis is a condition where there is an inappropriate deposition of fibroid tissue on the wall of the uterus.

This condition is a cause of dysmenorrhea and infertility in women. The exact cause of this condition is poorly understood but evidence suggests that it is an inappropriate response of fibroid tissue to estrogen. Such a condition has been produced in rabbits by daily administrations of estrogen for 3 months. In guinea pigs, the condition has been produced by daily administration of estrogen for four months. Further, in rats, estrogen causes similar hypertrophy.

The most common treatment of uterine fibrosis involves surgical procedures both costly and sometimes a source of complications such as the formation of abdominal adhesions and infections. In some patients, initial surgery is only a temporary treatment and the fibroids regrow. In those cases a hysterectomy is performed which effectively ends the fibroids but also the reproductive life of the patient. Also, gonadotropin releasing hormone antagonists may be administered, yet their use is tempered by the fact they can lead to osteoporosis. Thus, there exists a need for new methods for treating uterine fibrosis, and the methods of the present invention satisfy that need.

Endometriosis is a condition of severe dysmenorrhea, which is accompanied by severe pain, bleeding into the endometrial masses or peritoneal cavity and often leads to infertility. The cause of the symptoms of this condition appear to be ectopic endometrial growths which respond inappropriately to normal hormonal control and are located in inappropriate tissues. Because of the inappropriate locations for endometrial growth, the tissue seems to initiate local inflammatory-like responses causing macrophage infiltration and a cascade of events leading to initiation of the painful response. The exact etiology of this disease is not well understood and its treatment by hormonal therapy is diverse, poorly defined, and marked by numerous unwanted and perhaps dangerous side effects.

One of the treatments for this disease is the use of low dose estrogen to suppress endometrial growth through a negative feedback effect on central gonadotropin release and subsequent ovarian production of estrogen; however, it is sometimes necessary to use continuous estrogen to control the symptoms. This use of estrogen can often lead to undesirable side effects and even the risk of endometrial cancer.

Another treatment consists of continuous administration of progestins which induces amenorrhea and by suppressing ovarian estrogen production can cause regressions of the endometrial growths. The use of chronic progestin therapy is often accompanied by the unpleasant CNS side effects of progestins and often leads to infertility due to suppression of ovarian function.

A third treatment consists of the administration of weak androgens, which are effective in controlling the endometriosis; however, they induce severe masculinizing effects. Several of these treatments for endometriosis have also been implicated in causing a mild degree of bone loss with continued therapy. Therefore, new methods of treating endometriosis are desirable.

SUMMARY OF THE INVENTION

The present invention relates to compounds of formula I

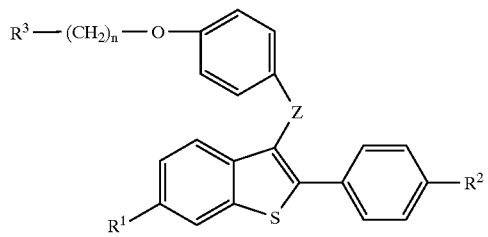

I wherein $R^1$ is —H, —OH, —O($C_1$–$C_4$ alkyl), —OCOC$_6$H$_5$, —OCO($C_1$–$C_6$ alkyl), or —OSO$_2$($C_2$–$C_6$ alkyl);

$R^2$ is —H, —OH, —O($C_1$–$C_4$ alkyl), —OCOC$_6$H$_5$, —OCO($C_1$–$C_6$ alkyl), —OSO$_2$($C_2$–$C_6$ alkyl) or halo;

$R^3$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;

n is 2 or 3; and z is —O— or —S—;

or a pharmaceutically acceptable salt thereof.

Further provided by the present invention are the following intermediate compounds which are useful for preparing pharmaceutically active compounds of the present invention, some of which are also pharmaceutically active:

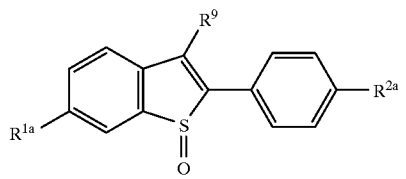

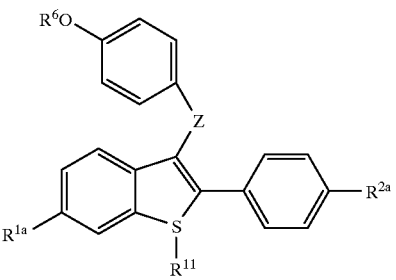

II

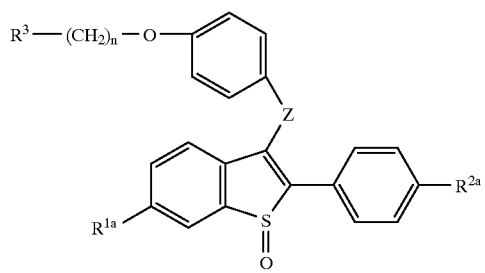

wherein

R$^{1a}$ is —H or —OR$^7$ in which R$^7$ is a hydroxy protecting group;

R$^{2a}$ is —H, halo, or —OR$^8$ in which R$^8$ is a hydroxy protecting group;

R$^3$ is 1-piperidinyl, 1-pyrrolidinyl, methyl-1-pyrrolidinyl, dimethyl-1-pyrrolidinyl, 4-morpholino, dimethylamino, diisopropylamino, or 1-hexamethyleneimino;

R$^6$ is —H or a hydroxy protecting group which can be selectively removed;

R$^9$ is a leaving group;

R$^{11}$ is non-existent or=O;

n is 2 or 3; and

Z is —O— or —S—;

or a pharmaceutically acceptable salt thereof.

Also provided is a process for preparing compounds of the formula

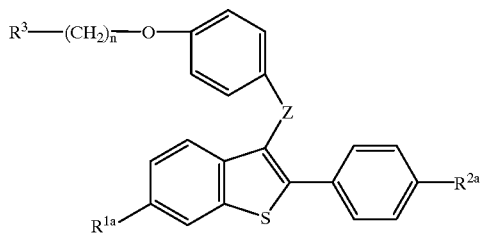

wherein

R$^{1a}$ is —H or —OR$^{7a}$ in which R$^{7a}$ is —H or a hydroxy protecting group;

R$^{2a}$ is —H, halo, or —OR$^{8a}$ in which R$^{8a}$ is —H or a hydroxy protecting group;

R$^3$ is 1-piperidinyl, 1-pyrrolidino, methyl-1-pyrrolidinyl, dimethyl-1-pyrrolidino, 4-morpholino, dimethylamino, diethylamino, diisopropylamino, or 1-hexamethyleneimino;

n is 2 or 3; and

Z is —O— or —S—;

or a pharmaceutically acceptable salt thereof, comprising a) oxidizing the sulfur atom of a formula IV compound

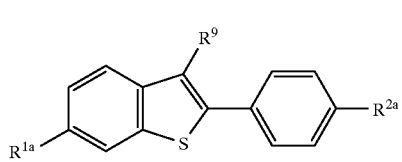

wherein

R$^{1a}$ and R$^{2a}$ are as previously defined; and

R$^9$ is a leaving group;

b) reacting the product of step a), a compound of formula XIV

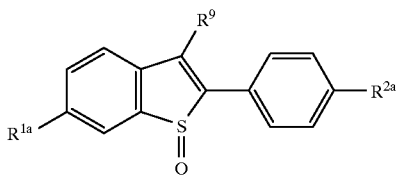

with a nucleophilic group of the formula

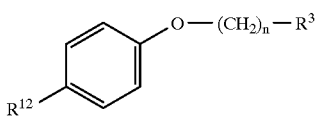

wherein R$^{12}$ is —OH or —SH;

c) reducing the product of step b), a compound of formula XVI

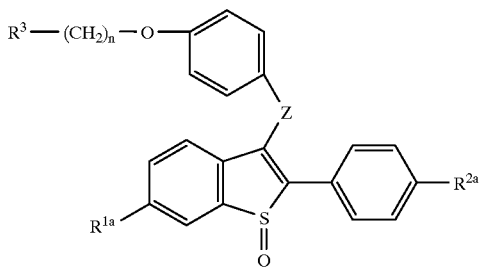

to provide a compound of the formula

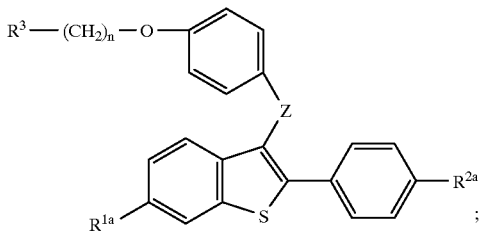

d) optionally removing the R$^{1a}$ and/or R$^{2a}$ hydroxy protecting groups, when present, of the product of step c); and e) optionally forming a salt of the product of step c) or step d).

"The present invention further relates to pharmaceutical compositions containing compounds of formula I, optionally containing estrogen or progestin, and the use of such compounds, alone, or in combination with estrogen or progestin, for alleviating the symptoms of post-menopausal syndrome, particularly osteoporosis, cardiovascular related pathological condtions, and hormonally-dependent cancer, particularly estrogen-dependent cancer." As used herein, the term "estrogen" includes steroidal compounds having estrogenic activity such as, for example, 17b-estradiol, estrone, conjugated estrogen (Premarin®), equine estrogen 17b-ethynyl estradiol, and the like. As used herein, the term "progestin" includes compounds having progestational activity such as, for example, progesterone, norethylnodrel, nongestrel, megestrol acetate, norethindrone, and the like.

The compounds of the present invention also are useful for inhibiting uterine fibroid disease and endometriosis in women, and aortal smooth muscle cell proliferation, particularly restenosis, in humans.

DETAILED DESCRIPTION OF THE INVENTION

One aspect of the present invention includes compounds of formula I

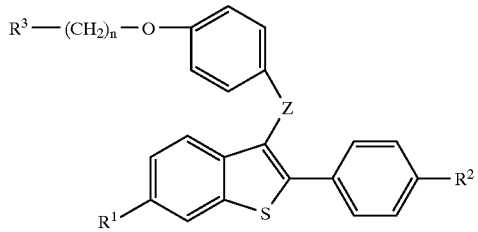

wherein $R^1$ is —H, —OH, —O($C_1$-$C_4$ alkyl), —OCOC$_6$H$_5$, —OCO($C_1$-$C_6$ alkyl), or —OSO$_2$($C_2$-$C_6$ alkyl);

$R^2$ is —H, —OH, —O($C_1$-$C_4$ alkyl), —OCOC$_6$H$_5$, —OCO($C_1$-$C_6$ alkyl), —OSO$_2$($C_2$-$C_6$ alkyl), or halo;

$R^3$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;

n is 2 or 3; and z is —O— or —S—;

or a pharmaceutically acceptable salt thereof.

General terms used in the description of compounds herein described bear their usual meanings. For example, "$C_1$-$C_6$ alkyl" refers to straight or branched aliphatic chains of 1 to 6 carbon atoms including moieties such as methyl, ethyl, propyl, isopropyl, butyl, n-butyl, pentyl, isopentyl, hexyl, isohexyl, and the like. Similarly, the term "$C_1$-$C_4$ alkoxy" represents a $C_1$-$C_4$ alkyl group attached through an oxygen molecule and include moieties such as, for example, methoxy, ethoxy, n-propoxy, isopropoxy, and the like.

The starting material for one route for preparing compounds of formula I of the present invention, compounds of formula III, are prepared essentially as described by C. D. Jones in U.S. Pat. Nos. 4,418,068, and 4,133,814, each of which is herein incorporated by reference. Formula III has the structure

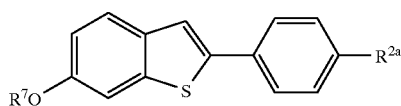

wherein $R^7$ and $R^{2a}$ are as defined above.

The $R^7$ and $R^8$ hydroxy protecting groups are moieties which generally are not found in the final, therapeutically active compounds of formula I, but which are intentionally introduced during a portion of the synthetic process to protect a group which otherwise might react in the course of chemical manipulations, and is then removed at a later stage of the synthesis. Since compounds bearing such protecting groups are of importance primarily as chemical intermediates (although some derivatives also exhibit biological activity), their precise structure is not critical. Numerous reactions for the formation, removal, and possibly, reformation of such protecting groups are described in a number of standard works including, for example, Protective Groups in Organic Chemistry, Plenum Press (London and New York, 1973); Green, T. W., Protective Groups in Organic Synthesis, Wiley (New York, 1981); and The Peptides, Vol. I, Schrooder and Lubke, Academic Press, (London and New York, 1965).

Representative hydroxy protecting groups include, for example, —$C_1$-$C_4$ alkyl, —$C_1$-$C_4$ alkoxy, —CO—($C_1$-$C_6$ alkyl), —SO$_2$—($C_4$-$C_6$ alkyl), and —CO—Ar in which Ar is benzyl or optionally substituted phenyl. The term "substituted phenyl" refers to a phenyl group having one or more substituents selected from the group consisting of $C_1$-$C_4$ alkyl, $C_1$-$C_4$ alkoxy, hydroxy, nitro, halo, and tri(chloro or fluoro) methyl. The term "halo" refers to bromo, chloro, fluoro, and iodo.

For compounds of formula III, preferred $R^7$ and $R^8$ ($R^{2a}$) substituents are methyl, isopropyl, benzyl, and methoxymethyl. Compounds in which $R^7$ and $R^8$ each are methyl are prepared via the procedure described in the above-referenced Jones patent. Another preferred hydroxy protecting group is methoxymethyl. However, a formula IV compound, as shown below, is first prepared bearing the preferred methyl or other hydroxy protecting group(s). These protecting groups are then removed, forming phenolic moieties, which are then reprotected with methoxymethyl protecting groups.

Compounds of formula III are also prepared in which $R^7$ hydroxy protecting groups are selectively removed, leaving the $R^8$($R^{2a}$) hydroxy protecting group as part of the final product. The same is true in which the $R^8$($R^{2a}$) hydroxy protecting group is selectively removed, leaving the $R^7$ hydroxy protecting group in place. For example, $R^7$ is isopropyl or benzyl and $R^8$($R^{2a}$) is methyl. The isopropyl or benzyl moiety is selectively removed via standard procedures, and the $R^8$ methyl protecting group is left as part of the final product.

The first steps of the present process for preparing certain compounds of formula I include selectively placing a leaving group at the 3 position of a formula III compound, coupling the reaction product of the first step with a 4-(protected-hydroxy)phenol, and removing the phenol's hydroxy protecting group. The present process is depicted in Scheme I below.

Scheme I

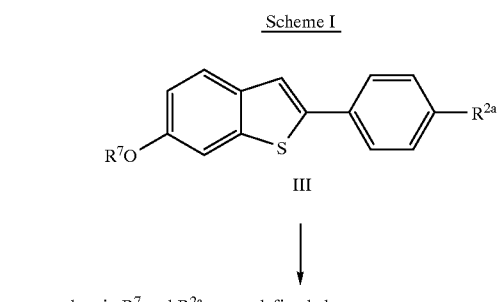

wherein $R^7$ and $R^{2a}$ are as defined above

-continued

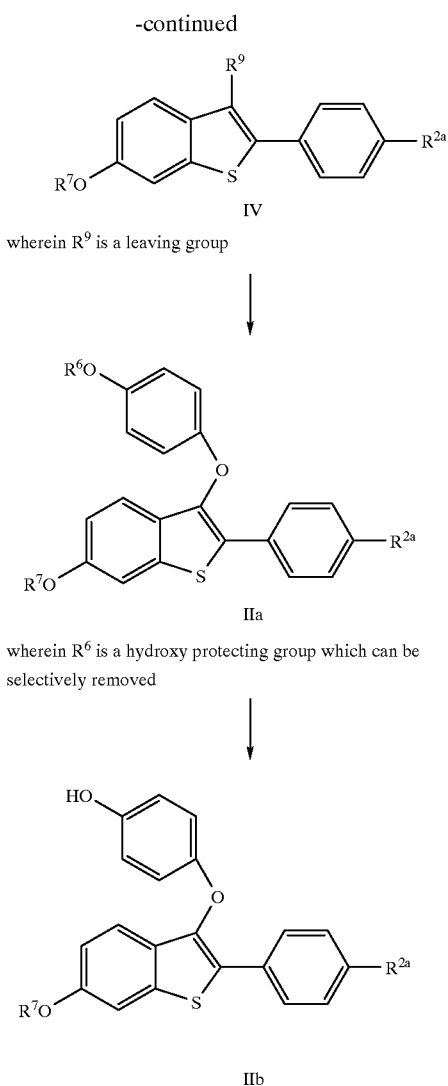

wherein $R^9$ is a leaving group wherein $R^6$ is a hydroxy protecting group which can be selectively removed In the first step of Scheme I, an appropriate leaving group is selectively placed at the 3-position of the formula III starting material via standard procedures. Appropriate $R^9$ leaving groups include the sulfonates such as methanesulfonate, 4-bromobenzenesulfonate, toluenesulfonate, ethanesulfonate, isopropanesulfonate, 4-methoxybenzene-sulfonate, 4-nitrobenzenesulfonate, 2-chlorobenzenesulfonate, triflate, and the like, halogens such as bromo, chloro, and iodo, and other related leaving groups. However, to insure proper placement of the leaving group, the named halogens are preferred, and bromo is especially preferred.

The present reaction is carried out using standard procedures. For example, when the preferred halogenating agents are used, an equivalent of such a halogenating agent, preferably bromine, is reacted with an equivalent of the formula III substrate, in the presence of a suitable solvent such as, for example, chloroform or acetic acid. The reaction is run at a temperature from about 40° C. to about 80° C.

The reaction product from the above process step, a compound of formula IV, is then reacted with a 4-(protected-hydroxy)phenol to form compounds of formula IIa in which $R^6$ is a selectively removable hydroxy protecting group. Generally, the 4-hydroxy protecting moiety of the phenol may be any known protecting group which can be selectively removed without removing, in this instance, the $R^7$ and, when present, $R^8$ moieties of a formula IIa compound. Preferred $R^6$ protecting groups include methoxymethyl, when $R^7$ and/or $R^8$ are not methoxymethyl, and benzyl. Of these, benzyl is especially preferred. The 4-(protected-hydroxy)phenol reactants are commercially available or can be prepared via standard procedures.

This coupling reaction is known in the art as an Ullman reaction and is run according to standard procedures [see, e.g., Advanced Organic Chemistry: Reactions, mechanisms, and Structure, Fourth Edition, 3–16, (J. March, ed., John Wiley & Sons, Inc. 1992); Jones, C. D., J. Chem. Soc. Perk. Trans. I, 4:407 (1992)].

In general, equivalent amounts of the two aryl substrates, in the presence of up to an equimolar amount of a copper(I) oxide catalyst and an appropriate solvent, are heated to reflux under an inert atmosphere. Preferably, an equivalent of a formula IV compound in which $R^9$ is bromo is reacted with an equivalent amount of 4-benzyloxyphenol in the presence of an equivalent of cuprous oxide.

Appropriate solvents for this reaction are those solvents or mixture of solvents which remain inert throughout the reaction. Typically, organic bases, particularly a hindered base such as, for example, 2,4,6-collidine, are preferred solvents.

The temperature employed in this step should be sufficient to effect completion of this coupling reaction, and will influence the amount of time required therefore. When the reaction mixture is heated to reflux under an inert atmosphere such as nitrogen, the time-to-completion usually will be from about 20 to about 60 hours.

Following coupling, which forms a formula IIa compound, formula IIb compounds are prepared by selectively removing the $R^6$ hydroxy protecting group of a formula IIa compound via well known reduction procedures. It is imperative that the selected procedure will not affect the $R^7$ and, when present, $R^8$ hydroxy protecting groups.

When $R^6$ is the preferred benzyl moiety, and $R^7$ and, when present, $R^8$ each are methyl, the present process step is carried out via standard hydrogenolysis procedures. Typically, the formula IIa substrate is added to a suitable solvent or mixture of solvents, followed by the addition of a proton donor to accelerate the reaction and an appropriate hydrogenation catalyst.

Appropriate catalysts include noble metals and oxides such as palladium, platinum, and rhodium oxide on a support such as carbon or calcium carbonate. Of these, palladium-on-carbon, particularly 10% palladium-on-carbon, is preferred.

Solvents for this reaction are those solvents or mixture of solvents which remain inert throughout the reaction. Typically, ethylacetate and $C_1$–$C_4$ aliphatic alcohols, particularly ethanol, is preferred.

For the present reaction, hydrochloric acid serves as an adequate and preferred proton donor.

When run at ambient temperature and a pressure ranging form about 30 psi to about 50 psi, the present reaction runs quite rapidly. Progress of this reaction may be monitored by standard chromatographic techniques such as thin layer chromatography.

Compounds of formula IIa and IIb are novel, are encompassed within the genus described herein as formula II compounds, and are useful for preparing the pharmaceutically active compounds of formula I.

Upon preparation of a formula IIb compound, it is reacted with a compound of formula V

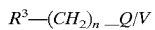

wherein $R^3$ and n are as defined above, and Q is a bromo or, preferably, a chloro moiety, to form a compound of formula VI. The formula VI compound is then deprotected to form a compound of formula Ia. These steps of the present process are shown in Scheme II below

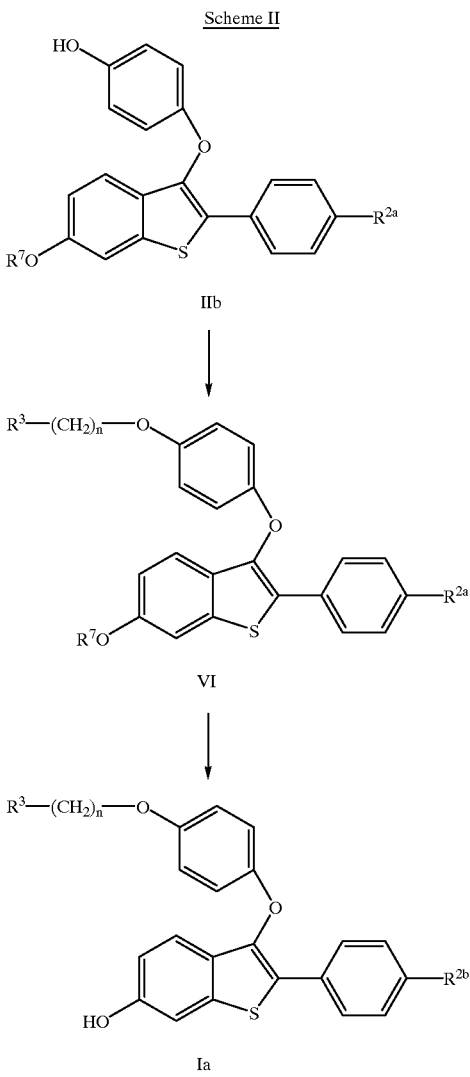

wherein $R^3$, $R^7$, $R^{2a}$, and n are as defined above, and $R^{2b}$ is —H, —OH, or halo.

In the first step of the process shown in Scheme II, the alkylation is carried out via standard procedures. Compounds of formula V are commercially available or are prepared by means well known to one of ordinary skill in the art. Preferably, the hydrochloride salt of a formula V compound, particularly 2-chloroethylpiperidine hydrochloride, is used.

Generally, at least about 1 equivalent of formula IIb substrate are reacted with 2 equivalents of a formula V compound in the presence of at least about 4 equivalents of an alkali metal carbonate, preferably cesium carbonate, and an appropriate solvent.

Solvents for this reaction are those solvents or mixture of solvents which remain inert throughout the reaction. N,N-dimethylformamide, especially the anhydrous form thereof, is preferred.

The temperature employed in this step should be sufficient to effect completion of this alkylation reaction. Typically, ambient temperature is sufficient and preferred.

The present reaction preferably is run under an inert atmosphere, particularly nitrogen.

Under the preferred reaction conditions, this reaction will run to completion in about 16 to about 20 hours. Of course, the progress of the reaction can be monitored via standard chromatographic techniques.

As an alternative for preparing compounds of formula VI, a formula IIb compound is reacted with an excess of an alkylating agent of the formula

wherein Q and Q' each are the same or different leaving group, in an alkali solution. Appropriate leaving groups are the aforementioned leaving groups used in the preparation of compounds of formula IV.

A preferred alkali solution for this alkylation reaction contains potassium carbonate in an inert solvent such as, for example, methyethyl ketone (MEK) or DMF. In this solution, the 4-hydroxy group of the benzoyl moiety of a formula IIb compound exists as a phenoxide ion which displaces one of the leaving groups of the alkylating agent.

This reaction is best when the alkali solution containing the reactants and reagents is brought to reflux and allowed to run to completion. When using MEK as the preferred solvent, reaction times run from about 6 hours to about 20 hours.

The reaction product from this step is then reacted with 1-piperidine, 1-pyrrolidine, methyl-1-pyrrolidine, dimethyl-1-pyrrolidine, 4-morpholine, dimethylamine, diethylamine, diisopropylamine, or 1-hexamethyleneimine, via standard techniques, to form compounds of formula VI. Preferably, the hydrochloride salt of piperidine is reacted with the alkylated compound of formula IIb in an inert solvent, such as anhydrous DMF, and heated to a temperature in the range from about 60° C. to about 110° C. When the mixture is heated to a preferred temperature of about 90° C., the reaction only takes about 30 minutes to about 1 hour. However, changes in the reaction conditions will influence the amount of time this reaction needs to be run for completion. Of course, the progress of this reaction step can be monitored via standard chromatographic techniques.

Compounds of formula VI, in which $R^7$ and when present, $R^8$ each are $C_1$–$C_4$ alkyl, preferably methyl, and in which $R^{2a}$ is —H or halo, are novel and are pharmaceutically active for the methods herein described. Accordingly, such compounds are encompassed by the definition herein of compounds of formula I.

Certain preferred compounds of formula I are obtained by cleaving the $R^7$ and, when present, $R^8$ hydroxy protecting groups of formula VI compounds via well known procedures. Numerous reactions for the formation and removal of such protecting groups are described in a number of standard works including, for example, Protective Groups in Organic Chemistry, Plenum Press (London and New York, 1973); Green, T. W., Protective Groups in Organic Synthesis, Wiley, (New York, 1981); and The Peptides, Vol. I, Schrooder and Lubke, Academic Press (London and New York, 1965). Methods for removing preferred $R^7$ and/or $R^8$ hydroxy protecting groups, particularly methyl and methoxymethyl, are essentially as described in the Examples, infra.

Compounds of formula Ia are novel, are pharmaceutically active for the methods herein described, and are encompassed by formula I as defined herein.

Compounds of formula I in which $R^1$ is —H are prepared via the synthetic route shown below in Scheme III. Using this route, a 3-position leaving group ($R^9$) is placed on commercially available thianaphthene (formula VII) to form a compound of formula VIII, which is then coupled with a 4-(protected-hydroxy)phenol, providing compounds of formula IX.

Scheme III

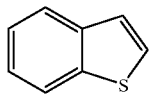

VII

↓

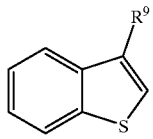

VIII

↓

-continued

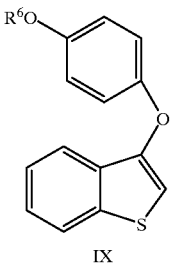

IX wherein $R^6$ is a hydroxy protecting group which can be selectively removed and $R^9$ is a leaving group.

The compound of formula VII is commercially available. Preparation of formulae VIII and IX compounds, including the definition of $R^6$ and $R^9$ substituents, as well as preferred reactants and conditions, unless otherwise herein stated, are the same as described above and shown in Scheme I, supra.

Compounds of formula IX are then arylated via Suzuki coupling [see, e.g., Suzuki, A., Pure and Appl. Chem., 6(2):213–222 (1994)]. Using one Suzuki coupling option, a formula IX compound is selectively halogenated at the 2-position, and then coupled with an arylboronic acid compound of formula XIa (Route A of Scheme IV below).

Preferably, however, an arylboronic acid of formula Xb is formed from a compound of formula IX, and then reacted with a halo-arene of formula XIb to give novel intermediates of formula IIc (Route B of Scheme IV below). Such novel intermediates are useful for preparing pharmaceutically active compounds of the present invention (formula Ib compounds) via alkylation and deprotection.

Scheme IV

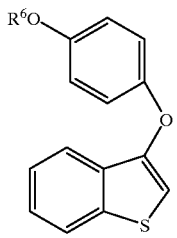

IX

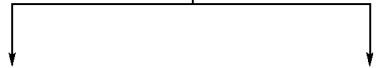

-continued
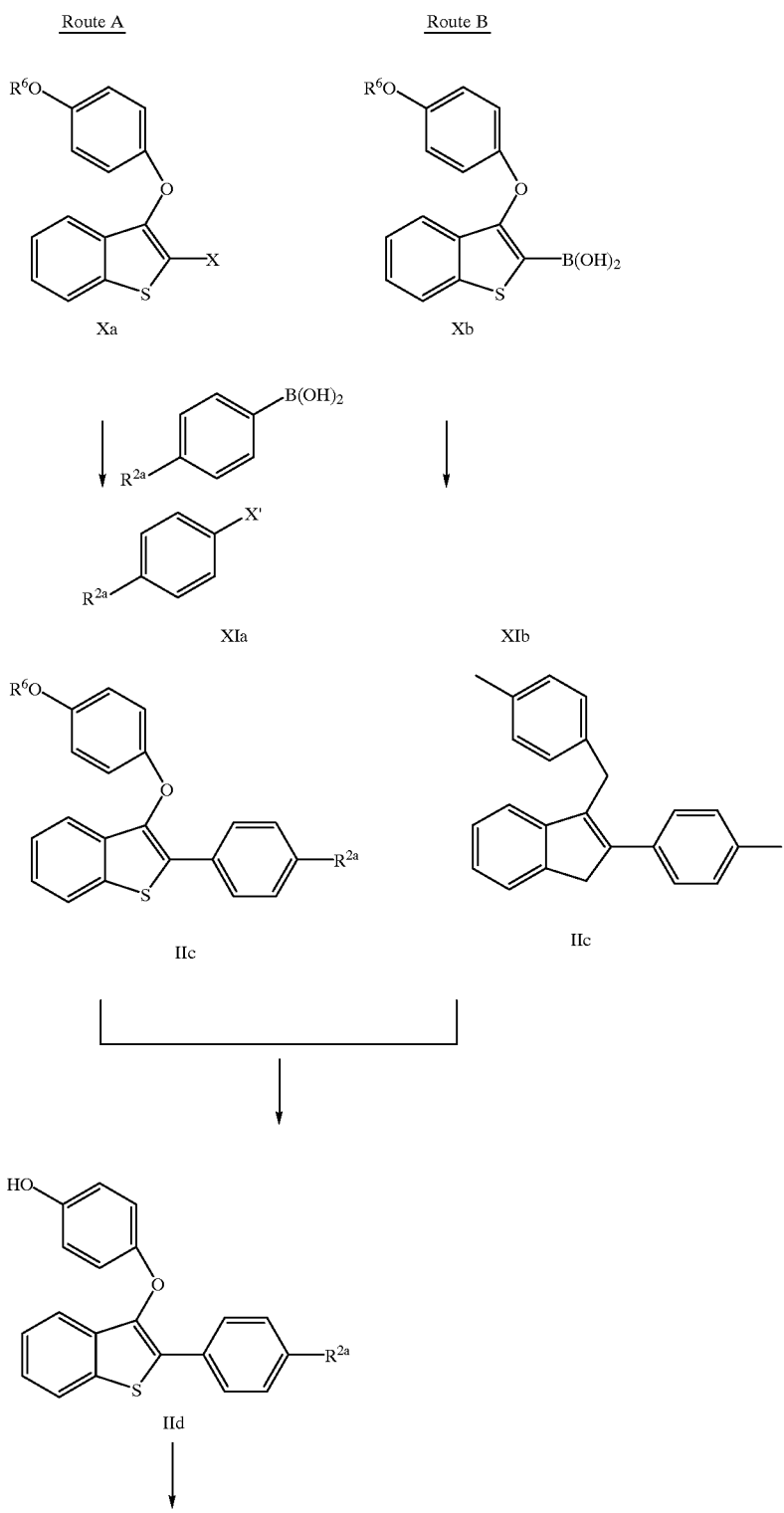

-continued

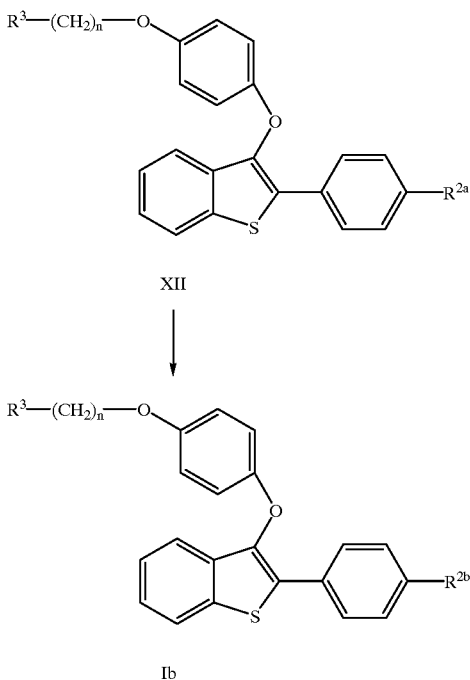

wherein $R^{2a}$, $R^{2b}$, $R^3$, $R^6$ and n are as defined above;

X is iodo, bromo, or fluoro, in the order of preference; and

X' is iodo, bromo, or fluoro, in the order of preference, or triflate.

The first step in Route A in Scheme IV is the 2-position iodination or bromination of a formula IX compound using standard procedures. Generally, a formula IX compound is reacted with a slight excess of n-butyllithium in hexane, in an appropriate solvent and under an inert atmosphere such as nitrogen, followed by the dropwise addition of a slight excess of the desired halogenating agent in an appropriate solvent. Preferably, the halogenating agent for this step is iodine, but the use of bromine, N-bromosuccinimide is also permitted.

Appropriate solvents include an inert solvent or mixture of solvents such as, for example, diethyl ether, dioxane, and tetrahydrofuran (THF). Of these, tetrahydrofuran, particularly anhydrous THF, is preferred.

The present selective, 2-position halogenation reaction optionally is run at a temperature from about −75° C. to about 85° C.

The product of the above reaction, a halo-arene of formula Xa, is then coupled with an arylboronic acid of formula XIa, via standard Suzuki coupling procedures, to provide compounds of formula IIc. Compounds of formula XIa, in which $R^{2a}$ is —H, halo, or —$OR^8$ ($R^8$ is a hydroxy protecting group as defined, supra) are derived from commercially available compounds via procedures well known to one of ordinary skill in the art (see, e.g., March J.; and Suzuki, A., supra).

In the present coupling reaction, a slight excess of a formula XIa compound is reacted with each equivalent of a formula Xa compound in the presence of a palladium catalyst and an appropriate base in an inert solvent such as toluene.

Although various palladium catalysts drive Suzuki coupling reactions, the catalyst selected usually is reaction specific. Thus, the use of tetrakistriphenylphosphine palladium in the present reaction is highly preferred.

Likewise, various bases may be used in the present coupling reaction. However, it is preferred to use an alkali metal carbonate, particularly 2N sodium carbonate.

The temperature employed in this step should be sufficient to effect completion of the coupling reaction. Typically, heating the reaction mixture to reflux for a period from about 2 to about 4 hours is adequate and preferred.

In Route B of Scheme IV, a 2-position arylboronic of formula Xb is prepared using well known procedures. Generally, a compound of formula IX is treated with a slight excess of n-butyllithium in hexanes, in an appropriate solvent and under an inert atmosphere such as nitrogen, following by the dropwise addition of an appropriate trialkylborate.

Appropriate solvents include an inert solvent or mixture of solvents such as, for example, diethyl ether, dioxane, and tetrahydrofuran (THF). THF, particularly anhydrous THF, is preferred.

The preferred trialkylborate used in the present reaction is triisopropyl borate.

The product of this reaction, a compound of formula Xb, is then reacted with a aryl halide or aryl triflate of formula XIb, via standard Suzuki coupling procedures, to provide compounds of formula IIc. The preferred reaction conditions for the present reaction are as described for the reaction of compounds of formulae XIa and Xa, in Scheme IV, which also provide compounds of formula IIc.

The transformation of compounds of formula IIc to formula Ia compounds is carried out as described above for the conversion of formula IIa compounds to compounds of formula Ia.

Compounds of formulae IIc and IId are novel, and are useful for the preparation of pharmaceutically active compounds of the present invention.

Compounds of formulae XII and Ib also are novel, are useful for the methods herein described, and are encompassed by formula I as herein defined.

Compounds of formula I in which either $R^1$ or $R^2$ is —H and the other $R^1$ or $R^2$ substituent is —OH also are prepared from compounds of formula I in which both $R^1$ or $R^2$ are —OH. The dihydroxy compound of formula I is converted to a mixture of 6- and 4'-monotriflates, and the triflate moiety is reduced to hydrogen [see, Saa, J. M., et al., J. Org. Chem., 51:991 (1990)]. The resulting mixture of monohydroxy derivatives, either as the free base or pharmaceutically acceptable salt, preferably the hydrochloride salt, can then be separated by standard crystallization techniques.

In general, a dihydroxy compound of formula I is treated with about 4 to about 6 equivalents of a amine base, such as triethylamine, in a non-reactive solvent followed by the addition of 1 equivalent of trifluoromethanesulfonic anhydride. A statistical mixture of mono- and di-triflates are produced and separated by standard chromatographic techniques. A preferred solvent for this step is anhydrous dichloromethane.

When run at a temperature range from about 0° C. to about 250° C., the present reaction is completed within from about 1 to about 5 hours.

The isolated mixture of mono-triflated compounds is then hydrogenated, in a non-reactive solvent, in the presence of from about 3 to about 6 equivalents of an amine base, preferably triethylamine, and a hydrogenation catalyst such as palladium-on-carbon, which is preferred. Preferred solvents for this reaction include ethyl acetate and ethanol or, alternatively, a mixture thereof. When this step of the present reaction is run under about 40 psi of hydrogen gas, at ambient temperature, the reaction time is from about 2 hours to about 5 hours.

The resulting mixture of monohydroxy derivatives of formula I have different solubilities in ethyl aceate and the 6-hydroxy-4'-hydrogen derivatives can be partially separated from the 6-hydrogen-4'-hydroxy derivatives by selective crystallization. Further separation, which provides pure monohydroxy compounds of formula I, can be achieved by conversion of the enriched mixtures to the hydrochloride salts followed by crystallization from ethyl acetate-ethanol.

A more direct method for the preparation of compounds of formula I in which either $R^1$ or $R^2$ is —H and the other $R^1$ or $R^2$ substituent is —OH, as well as an alternative method for the preparation of compounds of formula I in which either $R^1$ or $R^2$ is —H and the other $R^1$ or $R^2$ substituent is —O—($C_1$–$C_4$ alkyl) uses a compound of the formula

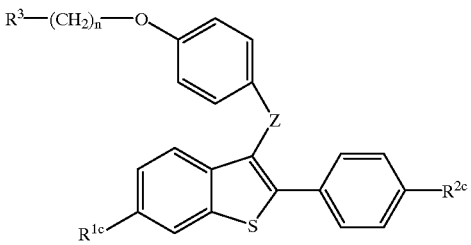

wherein $R^3$ and n are defined above;

$R^{1c}$ is —OH or —O—($C_1$–$C_4$ alkyl); and $R^{2c}$ is —OH or —O—($C_1$–$C_4$ alkyl);

providing when $R^{1c}$ is —OH, $R^{2c}$ is —O—($C_1$–$C_4$ alkyl), and when $R^{1c}$ is —O—($C_1$–$C_4$ alkyl) $R^{2c}$ is —OH.

In this process, the hydroxy moiety of such a compound is converted to a triflate derivative by treatment with trifluoromethane sulfonic anhydride. The triflate moiety is then reduced under standard conditions, preferably by catalytic hydrogenation. The hydroxy protecting moiety is then removed via standard procedures, as in those herein described, providing compounds of formula I in which either $R^1$ or $R^2$ is —H and the other $R^1$ or $R^2$ substituent is —OH.

Another alternative, and preferred, method for the preparation of compounds of the present invention is shown in Scheme V. In the present process, the sulfur atom of a formula IV compound (infra) is oxidized to form a sulfoxide (formula XIV), which is then reacted with a nucleophilic group to introduce the oxygen or sulphur atom linker of formula I and formula II compounds. The sulfoxide moiety of formula XVI compounds is then reduced to provide certain compounds of the present invention.

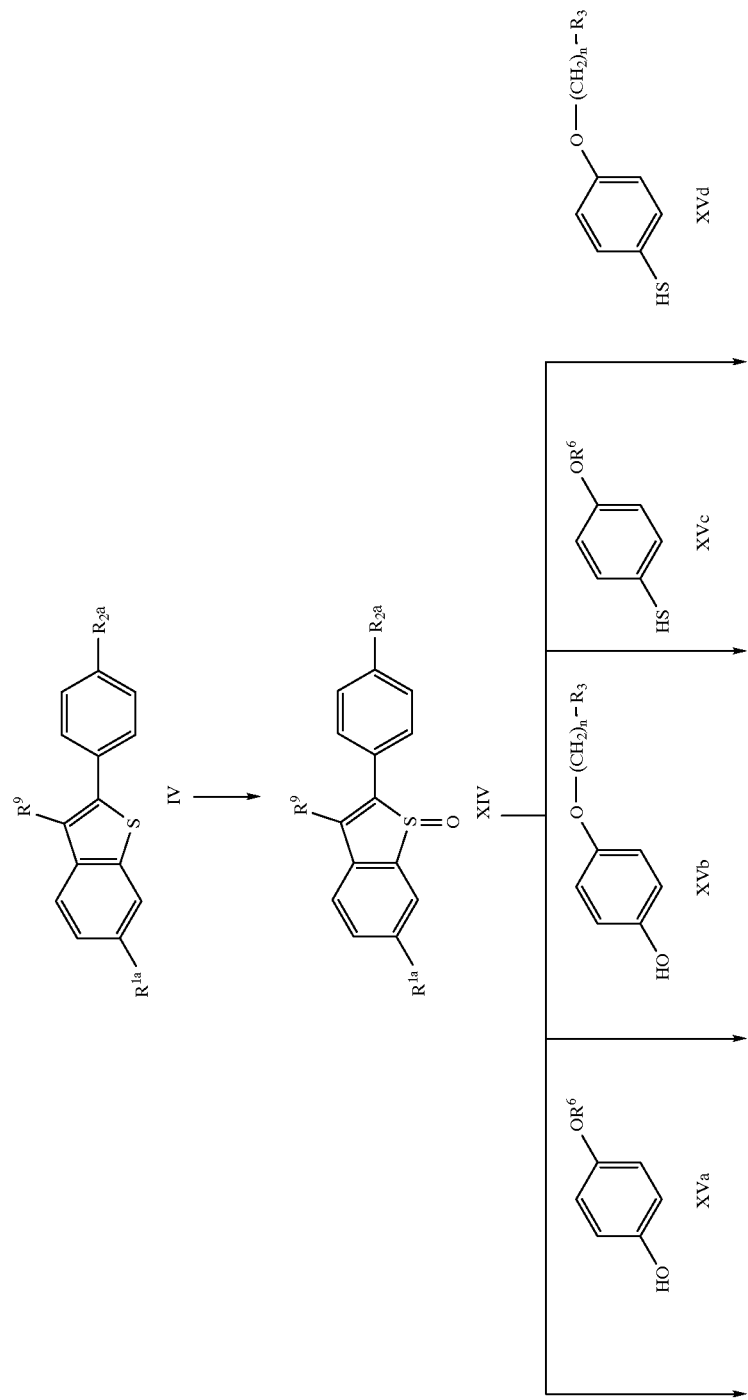

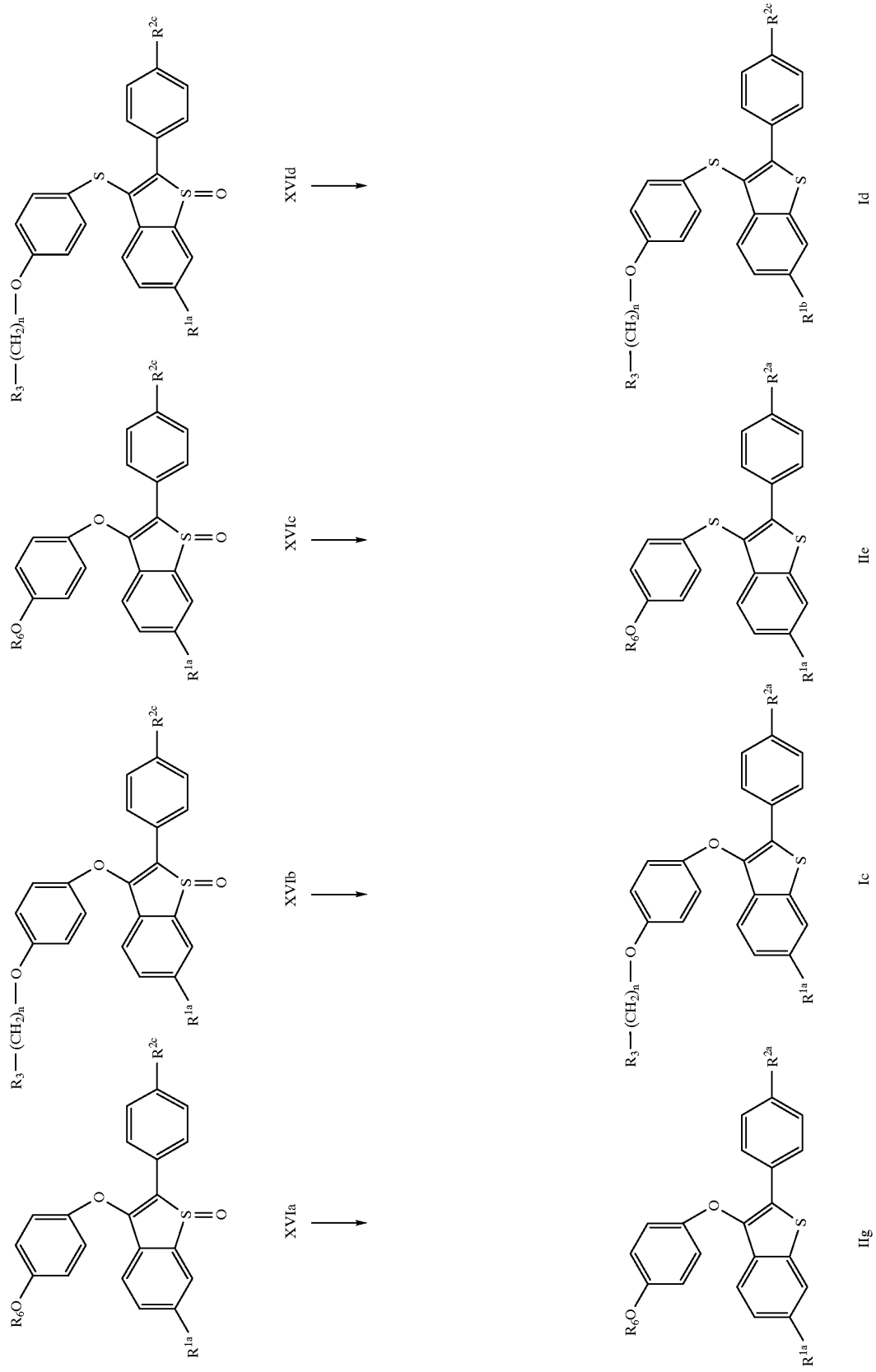

wherein each variable has its previously defined meaning.

In the first step of this process, a compound of formula IV is selectively oxidized to the sulfoxide. A number of known methods are available for the process step [see, e.g., Madesclaire, M., Tetrahedron, 42 (20); 5459–5495 (1986); Trost, B. M., et al., Tetrahedron Letters, 22 (14); 1287–1290 (1981); Drabowicz, J., et al., Synthetic Communications, 11 (12); 1025–1030 (1981); Kramer, J. B., et al., 34th National Organic Symposium, Williamsburg, VA., June 11–15, 1995]. However, many oxidants provide only poor conversion to the desired product as well as significant over-oxidation to the sulfone. The present, novel process, however, converts a formula IV compound to a sulfoxide of formula XIV in high yield with little or no formation of sulfones. This process involves the reaction of a formula IV compound with about 1 to about 1.5 equivalents of hydrogen peroxide in a mixture of about 20% to about 50% trifluoroacetic acid in methylene chloride. The reaction is run at a temperature from about 10° C. to about 50° C., and usually required from about 1 to about 2 hours to run to completion.

Next, the 3-position leaving group ($R^9$) is displaced by the desired nucleophilic derivative of formula XV. Such nucleophilic derivatives are prepared via standard methods.

In this step of the process, the acidic proton of the nucleophilic group is removed by treatment with a base, preferably a slight excess of sodium hydride or potassium tertbutoxide, in a polar aprotic solvent, preferably DMF or tetrahydrofuran. Other bases that can be employed include potassium carbonate and cesium carbonate. Additionally, other solvents such as dioxane or dimethylsulfoxide can be employed. The deprotonation is usually run at a temperature between about 0° C. and about 30° C., and usually requires about 30 minutes for completion. A compound of formula XIV is then added to the solution of the nucleophile. The displacement reaction is run at a temperature between 0° C. and about 50° C., and is usually run in about 1 to about 2 hours. The product is isolated by standard procedures.

When a benzyl moiety is used as a hydroxy protecting group, hydrogenolysis of the sulfoxide moiety will also provide removal of the benzyl protecting group, eliminating the requirement for selectively removing such a group at a later stage in the process.

In the next step of the present process, novel sulfoxides of formulae XVI a, b, c, and d (collectively formula XVI) are reduced to a benzothiophene compound of formulae IIg, Ic, IIe, and Id, respectively. Prior to the present reduction process, compounds of formulae IIg and IIe can first be alkylated as herein described. Reduction of the sulfoxide compounds can be accomplished by using one of a multitude of methods known in the art including, for example, hydride reduction (lithium aluminum hydride), catalytic hydrogenation, transfer hydrogenolysis and trimethylsilyl iodide (TMS-I). In this reduction, the choice of reagent is dependent upon the compatibility of other functionalities in the molecule. For the compounds described in the present invention, lithium aluminum hydride ($LiAlH_4$) and transfer hydrogenolysis (palladium black/ammonium formate) are the preferred reagents. For $LiAlH_4$ reduction, appropriate solvents such as, for example, diethyl ether, dioxane, and tetrahydrofuran (THF). Of these, THF, particularly anhydrous THF, is preferred. For transfer hydrogenolysis, alcohol solvents, particularly ethanol, is preferred. The reaction is run at a temperature from about 0° C. to about 60° C., and requires from about 0.5 hours to about 2 hours for completion.

When desired, the hydroxy protecting group or groups of the products of the process shown in Scheme v can be removed, and a salt of the product of any step of the process. Accordingly, the present invention provides a process for preparing compounds of the formula

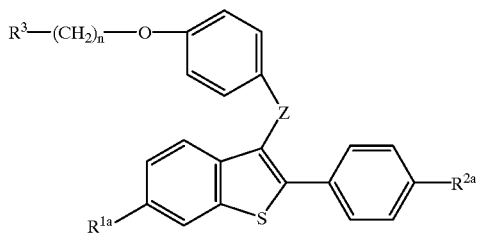

wherein $R^{1a}$ is —H or —$OR^{7a}$ in which $R^{7a}$ is —H or a hydroxy protecting group;

$R^{2a}$ is —H, halo, or —$OR^{8a}$ in which $R^{8a}$ is —H or a hydroxy protecting group;

$R^3$ is 1-piperidinyl, 1-pyrrolidino, methyl-1-pyrrolidinyl, dimethyl-1-pyrrolidino, 4-morpholino, dimethylamino, diethylamino, diisopropylamino, or 1-hexamethyleneimino;

n is 2 or 3; and

Z is —O— or —S—;

or a pharmaceutically acceptable salt thereof, comprising a) oxidizing the sulfur atom of a formula IV compound

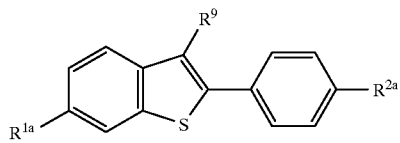

IV wherein $R^{1a}$ and $R^{2a}$ are as previously defined; and $R^9$ is a leaving group;

b) reacting the product of step a), a compound of formula XIV

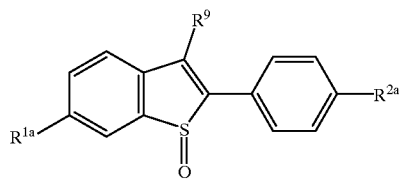

XIV with a nucleophilic group of the formula

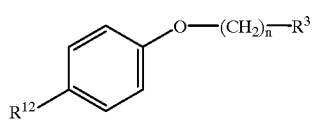

wherein $R^{12}$ is —OH or —SH;

c) reducing the product of step b), a compound of formula XVI

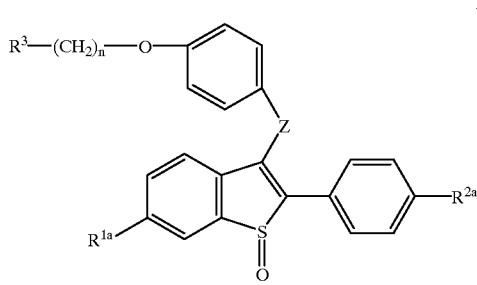

XVI to provide a compound of the formula

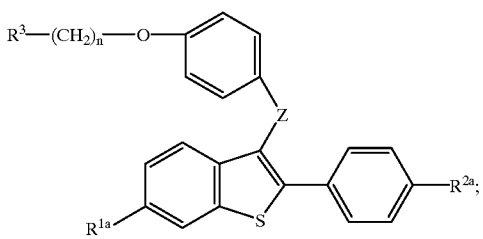

d) optionally removing the $R^{1a}$ and/or $R^{2a}$ hydroxy protecting groups, when present, of the product of step c); and e) optionally forming a salt of the product of step c) or step d).

This novel process also provides novel compounds of formulae XIV, and XVI a, b, c, and d, each of which is an intermediate useful for preparing the pharmaceutically active compounds of the present invention.

Compounds of formulae I in which Z is S are also prepared using the process described below in Scheme VI in which a compound of formula IVa is metallated. The resulting product, a compound of formula XVII is reacted with a 4-(protected hydroxy)phenyl disulfide of formula XVIII, and the phenol protecting group of a formula IIe compound is removed to provide compounds of formula IIf. One will note that, in using this process, $R^2$ cannot be halo because of chemical limitations.

Scheme VI

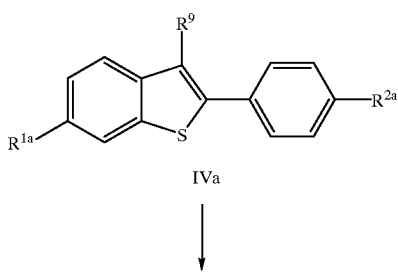

IVa

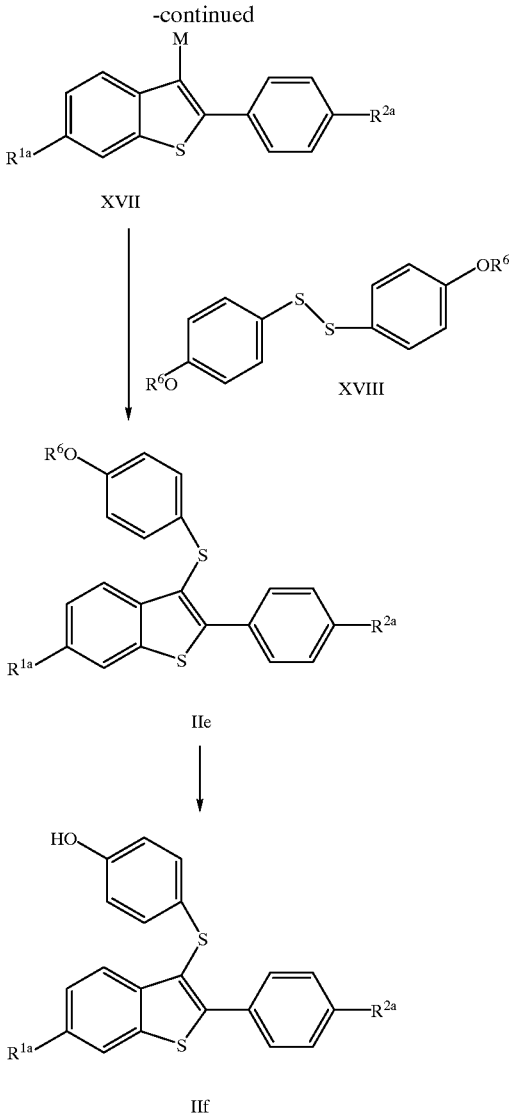

wherein $R^{1a}$ is —H or —$OR^7$ and $R^7$ is a hydroxy protecting group;

$R^{2a}$ is —H, or —$OR^8$ and $R^8$ is a hydroxy protecting group;

$R^6$ is a hydroxy protecting group which can be selectively removed;

$R^9$ is a leaving group; and

M is a metal ion.

In the first two steps of Scheme VI, a formula IVa compound is metallated via well known procedures. Most commonly, and preferably, a formula IVa compound is treated with a slight excess of n-butyllithium in hexanes in an appropriate solvent, followed by the dropwise addition of a solution of a disulfide compound of formula XVIII in an appropriate solvent.

Both of these reaction steps are run under an inert atmosphere such as nitrogen, while appropriate solvents for both steps include one or more inert solvents such as diethyl ether, dioxane, and THF. Of these, THF, particularly the anhydrous form thereof, is preferred. In addition, the present reaction steps are run at a temperature from about -78° C. to about 85° C.

In the first step of the present reaction, a metallated compound of formula XVII is provided. The 4-(protected-hydroxy)phenyl disulfide (a formula XVIII compound) which is reacted with such a formula XVII compound to give a compound of formula IIe, is prepared by protecting the hydroxy group of commercially available 4-hydroxyphenylsulfide with an appropriate protecting group via procedures known in the art. A preferred $R^6$ protecting group is methoxymethyl, providing $R^7$ and $R^8$, if either or both are present, is a hydroxy protecting group other than methoxymethyl. It is imperative that the $R^6$ hydroxy protecting group is a moiety different than those formed by $R^7$ and $R^8$ hydroxy protecting groups, when present, so that the $R^6$ group can selectively be removed, via standard procedures, to provide compounds of formula IIf.

To effect deprotection by removal of the $R^6$ protecting group, a formula IIe compound in a protic solvent or mixture of solvents is reacted in an acid media containing at least one equivalent of acid, preferably methanesulfonic acid, and heating from about 25° to about 110° C. Typically, the reaction time is from about 6 to about 24 hours, but the progress of the reaction may be monitored via standard chromatographic techniques.

Appropriate solvents for the present reaction include, for example, water and methanol.

Compounds of formulae IIe and IIf are novel, are useful for preparing pharmaceutically active compounds of formula I and are herein encompassed within the above depiction of formula II.

Compounds of formula Id

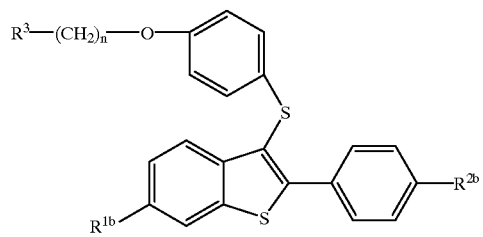

Id wherein $R^{1b}$ is —H or —OH;

$R^{2b}$ is —H or —OH; and $R^3$ and n, are as defined above, are prepared by using the above-described procedures related to the process steps shown in Schemes II and IV. Such compounds of formula Id also are novel, are useful for the methods of the present invention, and are herein encompassed within the above depiction of formula I.

Compounds of formula I, in which $R^1$ and $R^2$ are different hydroxy protecting groups or either $R^1$ and $R^2$ is a hydroxy protecting group and the other is hydroxy are selectively prepared by using a modified 2-arylbenzothiophene starting material of formula III above, providing that hydroxy protecting groups designated $R^7$ and $R^8$ are sufficiently different so that one protecting group is removed while the other group remains. Such 2-arylbenzothiophenes are prepared via procedures well known in the art.

Particularly useful for the preparation of formula I compounds in which $R^1$ and $R^2$ are different protecting groups is Suzuki coupling as described above in Scheme IV. However, 6-(protected hydroxy) benzothiophene-2-boronic acid is reacted with a formula XIb compound above in which $R^{2a}$ is —$OR^8$ and $R^7$ does not equal $R^8$. This reaction allows preparation of compounds of the present invention in which $R^7$ and $R^8$ are different hydroxy protecting groups so that one protecting group may selectively be removed and the other remains as a moiety of the final product. Preferably, the $R^7$ protecting group, especially benzyl or isopropyl, is removed to form a hydroxy moiety while the $R^8$ protecting group, particularly methyl, remains.

Suzuki coupling also is accomplished by using the above-described procedures but replacing a formula XIb compound with a compound of formula XIX

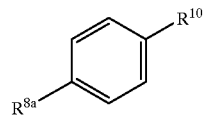

XIX wherein $R^{8a}$ is $C_1$–$C_6$ alkyl sulfonate, preferably methansulfonate or $C_4$–$C_6$ aryl sulfonate; and $R^{10}$ is a leaving group, preferably bromo or triflate.

In this process, a 6-(protecting hydroxy) benzothiophene-2-boronic acid as described above is reacted with a compound of formula XIX to provide a compound of formula XX, which is reacted with boron tribromide in methylene chloride to provide a monohydroxy compound which is subsequently converted to, for example, a benzyl moiety by standard procedures (formula XXI). The 4'-sulfonate ester is then selectively removed by basic hydrolysis or, preferably, by treatment with $LiAlH_4$, in an appropriate aprotic solvent such as, for example, THF. This reaction provides a compound of formula XXII which is finally, for example, methylated at the 4'-position via standard procedures (formula IIIa). of course, one skilled in the art will recognize that various processes can be utilized to provide formula IIIa compounds in which the hydroxy protecting groups are other than shown in Scheme VII below, but which can be selectively removed to provide monohydroxy compounds of formula I of the present invention.

Scheme VII

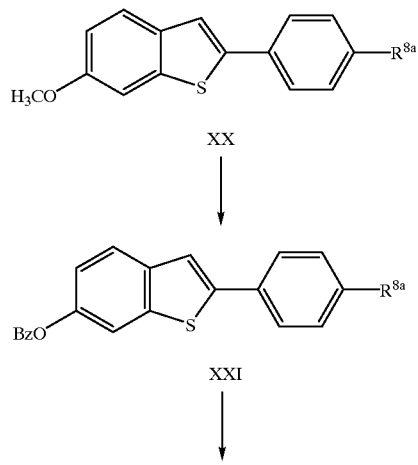

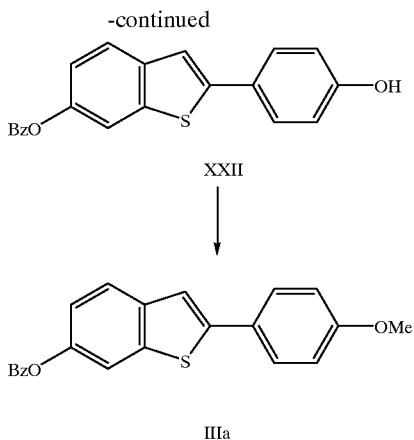

XXII

↓

IIIa

Compounds of IIIa are then subjected to the various processes herein described to provide compounds of formula I and II of the present invention.

Other preferred compounds of formula I are prepared by replacing 6- and/or 4'-position hydroxy moieties, when present, with a moiety of the formula —O—CO—($C_1$-$C_6$ alkyl), or —O—$SO_2$—($C_2$-$C_6$ alkyl) via well known procedures. See, e.g., U.S. Pat. No. 4,358,593.

For example, when an —O—CO($C_1$-$C_6$ alkyl) group is desired, a mono- or dihydroxy compound of formula I is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, e.g., Haslam, et al., Tetrahedron, 36:2409–2433 (1980).

The present reactions are carried out at moderate temperatures, in the range from about −25° C. to about 100° C., frequently under an inert atmosphere such as nitrogen gas. However, ambient temperature is usually adequate for the reaction to run.

Acylation of a 6-position and/or 4'-position hydroxy group also may be performed by acid-catalyzed reactions of the appropriate carboxylic acids in inert organic solvents. Acid catalysts such as sulfuric acid, polyphosphoric acid, methanesulfonic acid, and the like are used.

The aforementioned $R^1$ and/or $R^2$ groups of formula I compounds also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, e.g., Bull. Chem. Soc. Japan, 38:1979 (1965), and Chem. Ber., 788 and 2024 (1970).

Each of the above techniques which provide —O—CO—($C_1$-$C_6$ alkyl) moieties are carried out in solvents as discussed above. Those techniques which do not produce an acid product in the course of the reaction, of course, do not call for the use of an acid scavenger in the reaction mixture.

When a formula I compound is desired in which the 6- and/or 4'-position hydroxy group of a formula I compound is converted to a group of the formula —O—SO2—($C_2$-$C_6$ alkyl), the mono- or dihydroxy compound is reacted with, for example, a sulfonic anhydride or a derivative of the appropriate sulfonic acid such as a sulfonyl chloride, bromide, or sulfonyl ammonium salt, as taught by King and Monoir, J. Am. Chem. Soc., 97:2566–2567 (1975). The dihydroxy compound also can be reacted with the appropriate sulfonic anhydride or mixed sulfonic anhydrides. Such reactions are carried out under conditions such as were explained above in the discussion of reaction with acid halides and the like.

Although the free-base form of formula I compounds can be used in the methods of the present invention, it is preferred to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, b-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethane-sulfonate, methanesulfonate, naphthalene-1-sulfonate, naphthalene-2-sulfonate, p-toluenesulfonate, xylenesulfonate, tartarate, and the like. Preferred salts are the hydrochloride and oxalate salts.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

Representative preferred compounds of the present invention include the following:

Group I

[6-methoxy-2-(4-methoxyphenyl)-3-bromo]benzo[b]thiophene-(S-oxide)

[6-isopropoxy-2-(4-methoxyphenyl)-3-bromo]benzo[b]thiophene-(S-oxide)

[6-methoxy-2-(4-isopropoxyphenyl)-3-bromo]benzo[b]thiophene-(S-oxide)

[2-(4-methoxyphenyl)-3-bromo]benzo[b]thiophene-(S-oxide)

[6-methoxy-3-[4-[2-(1-piperidinyl)ethoxy]phenoxy]-2-(4-methoxyphenyl)]benzo[b]thiophene-(S-oxide)

[3-[4-[2-(1-piperidinyl) ethoxy]phenoxy]-2-(4-methoxyphenyl)]benzo[b]thiophene-(S-oxide)
[6-benzyloxy-2-(4-methoxyphenyl)-3-bromo]benzo[b]thiophene-(S-oxide)
[6-isopropoxy-2-(4-methoxyphenyl)-3-bromo]benzo[b]thiophene-(S-oxide)
[6-methoxy-2-(4-benzyloxyphenyl)-3-bromo]benzo[b]thiophene-(S-oxide)
[6-methoxy-2-(4-isopropoxyphenyl)-3-bromo]benzo[b]thiophene-(S-oxide)
[6-benzyloxy-3-[4-[2-(1-piperidinyl)ethoxy]phenoxy]-2-(4-methoxyphenyl)]benzo[b]thiophene-(S-oxide)
[6-isopropoxy-3-[4-[2-(1-piperidinyl)ethoxy]phenoxy]-2-(4-methoxyphenyl)]benzo[b]thiophene-(S-oxide)
[6-methoxy-3-[4-[2-(1-piperidinyl)ethoxy]phenoxy]-2-(4-benzyloxyphenyl)]benzo[b]thiophene-(S-oxide)
[6-methoxy-3-[4-[2-(1-piperidinyl)ethoxy]phenoxy]-2-(4-isopropoxyphenyl)]benzo[b]thiophene-(S-oxide)
[6-methoxy-2-(4-methoxyphenyl)-3-(4-methoxymethyleneoxy) thiophenoxy]benzo[b]thiophene
[6-methoxy-2-(4-methoxyphenyl)-3-(4-hydroxy) thiophenoxy]benzo[b]thiophene Group II

[3-[4-[2-(1-piperidinyl)ethoxy]phenoxy]-2-(4-hydroxyphenyl)]benzo[b]thiophene
[3-[4-[2-(1-piperidinyl)ethoxy]phenoxy]-2-(4-hydroxyphenyl)]benzo[b]thiophene hydrochloride
[3-[4-[2-(1-pyrolidinyl)ethoxy]phenoxy]-2-(4-hydroxyphenyl)]benzo[b]thiophene
[3-[4-[2-(1-hexamethyleneimino)ethoxy]phenoxy]-2-(4-hydroxyphenyl)]benzo[b]thiophene
[3-[4-[2-(1-N,N-diethylamino)ethoxy]phenoxy]-2-(4-hydroxyphenyl)]benzo[b]thiophene
3-[4-[2-(1-piperidinyl)ethoxy]phenoxy]-2-(4-methoxyphenyl)]benzo[b]thiophene hydrochloride
[3-[4-[2-(1-piperidinyl)ethoxy]phenoxy]-2-(phenyl)]benzo[b]thiophene hydrochloride
[3-[4-[2-(1-piperidinyl)ethoxy]phenoxy]-2-(4-fluorophenyl)]benzo[b]thiophene
[6-methoxy-2-(4-methoxyphenyl)-3-(4-benzyloxy) phenoxy]-benzo[b]thiophene
[6-isopropoxy-2-(4-methoxyphenyl)-3-(4-benzyloxy) phenoxy]-benzo[b]thiophene
[6-methoxy-2-(4-isopropoxyphenyl)-3-(4-benzyloxy) phenoxy]-benzo[b]thiophene
[6-methoxy-3-[4-[2-(1-piperidinyl)ethoxy]-phenoxy]-2-(4-methoxyphenyl)]benzo[b]thiophene
[6-methoxy-3-[4-[2-(1-piperidinyl)ethoxy]-phenoxy]-2-(4-methoxyphenyl)]benzo[b]thiophene hydrochloride
[6-methoxy-3-[4-[2-(1-pyrolodinyl)ethoxy]phenoxy]-2-(4-methoxyphenyl)]benzo[b]thiophene
[6-methoxy-3-[4-[2-(1-hexamethyleneimino)ethoxy]phenoxy]-2-(4-methoxyphenyl)]benzo[b]thiophene hydrochloride
[6-methoxy-3-[4-[2-(1-N,N-diethylamino)ethoxy]phenoxy]-2-(4-methoxyphenyl)]benzo[b]thiophene hydrochloride
[6-methoxy-3-[4-[2-(morpholino)ethoxy]phenoxy]-2-(4-methoxyphenyl)]benzo[b]thiophene hydrochloride
[6-methoxy-3-[4-[3-(piperidino)propoxy]phenoxy]-2-(4-methoxyphenyl)]benzo[b]thiophene hydrochloride
[6-methoxy-3-[4-[3-(1-N,N-diethylamino)propoxy] phenoxy]-2-(4-methoxyphenyl)]benzo[b]thiophene hydrochloride
[6-hydroxy-3-[4-[2-(1-piperidinyl)ethoxy]-phenoxy]-2-(4-hydroxyphenyl)]benzo[b]thiophene
[6-hydroxy-3-[4-[2-(1-piperidinyl)ethoxy]phenoxy]-2-(4-hydroxyphenyl)]benzo[b]thiophene oxalate
[6-hydroxy-3-[4-[2-(1-piperidinyl)ethoxy]phenoxy]-2-(4-hydroxyphenyl)]benzo[b]thiophene hydrochloride
[6-hydroxy-3-[4-[2-(1-pyrolidinyl)ethoxy]phenoxy]-2-(4-hydroxyphenyl)]benzo[b]thiophene
[6-hydroxy-3-[4-[2-(1-hexamethyleneimino)ethoxy] phenoxy]-2-(4-hydroxyphenyl)]benzo[b]thiophene
[6-hydroxy-3-[4-[2-(1-N,N-diethylamino)ethoxy]phenoxy]-2-(4-hydroxyphenyl)]benzo[b]thiophene
[6-hydroxy-3-[4-[2-(morpholino)ethoxy]phenoxy]-2-(4-hydroxyphenyl)]benzo[b]thiophene hydrochloride
[6-hydroxy-3-[4-[3-(1-N,N-diethylamino)propoxy] phenoxy]-2-(4-hydroxyphenyl)]benzo[b]thiophene hydrochloride
[6-hydroxy-3-[4-[2-(1-N,N-diisopropylamino)-ethoxy] phenoxy]-2-(4-hydroxyphenyl)]benzo[b]thiophene hydrochloride
[6-hydroxy-3-[4-[3-(piperidino)propoxy]phenoxy]-2-(4-hydroxyphenyl)]benzo[b]thiophene hydrochloride
[6-methoxy-3-[4-[2-(1-piperidinyl)ethoxy]phenoxy]-2-(4-methoxyphenyl)]benzo[b]thiophene hydrochloride
[6-benzyloxy-3-[4-[2-(1-piperidinyl)ethoxy]phenoxy]-2-(4-methoxyphenyl)]benzo[b]thiophene
[6-benzyloxy-3-[4-[2-(1-pyrrolidinyl)ethoxy]phenoxy]-2-(4-methoxyphenyl)]benzo[b]thiophene
[6-benzyloxy-3-[4-[2-(1-hexamethylimino)ethoxy] phenoxy]-2-(4-methoxyphenyl)]benzo[b]thiophene
[6-benzyloxy-3-[4-[2-(1-N,N-dimethylamino)ethoxy] phenoxy]-2-(4-methoxyphenyl)]benzo[b]thiophene
[6-benzyloxy-3-[4-[2-(1-morpholino)ethoxy]phenoxy]-2-(4-methoxyphenyl)]benzo[b]thiophene
[6-isopropoxyoxy-3-[4-[2-(1-piperidinyl)ethoxy]phenoxy]-2-(4-methoxyphenyl)]benzo[b]thiophene
[6-isopropoxy-3-[4-[2-(1-pyrrolidinyl)ethoxy]phenoxy]-2-(4-methoxyphenyl)]benzo[b]thiophene
[6-isopropoxy-3-[4-[2-(1-hexamethylimino)ethoxy] phenoxy]-2-(4-methoxyphenyl)]benzo[b]thiophene
[6-isopropoxy-3-[4-[2-(1-N,N-dimethylamino)ethoxy] phenoxy]-2-(4-methoxyphenyl)]benzo[b]thiophene
[6-isopropoxy-3-[4-[2-(1-morpholino)ethoxy]phenoxy]-2-(4-methoxyphenyl)]benzo[b]thiophene
[6-hydroxy-3-[4-[2-(1-piperidinyl)ethoxy]phenoxy]-2-(4-methoxyphenyl)]benzo[b]thiophene
[6-hydroxy-3-[4-[2-(1-pyrrolidinyl)ethoxy]phenoxy]-2-(4-methoxyphenyl)]benzo[b]thiophene
[6-hydroxy-3-[4-[2-(1-hexamethylimino)ethoxy]phenoxy]-2-(4-methoxyphenyl)]benzo[b]thiophene
[6-hydroxy-3-[4-[2-(1-N,N-dimethylamino)ethoxy] phenoxy]-2-(4-methoxyphenyl)]benzo[b]thiophene
[6-hydroxy-3-[4-[2-(1-morpholino)ethoxy]phenoxy]-2-(4-methoxyphenyl)]benzo[b]thiophene
[6-hydroxy-3-[4-[2-(1-piperidinyl)ethoxy]phenoxy]-2-(4-methoxyphenyl)]benzo[b]thiophene hydrochloride
[6-hydroxy-3-[4-[2-(1-pyrrolidinyl)ethoxy]phenoxy]-2-(4-methoxyphenyl)]benzo[b]thiophene hydrochloride
[6-hydroxy-3-[4-[2-(1-hexamethylimino)ethoxy]phenoxy]-2-(4-methoxyphenyl)]benzo[b]thiophene hydrochloride
[6-hydroxy-3-[4-[2-(1-N,N-dimethylamino)ethoxy] phenoxy]-2-(4-methoxyphenyl)]benzo[b]thiophene hydrochloride
[6-hydroxy-3-[4-[2-(1-morpholino)ethoxy]phenoxy]-2-(4-methoxyphenyl)]benzo[b]thiophene hydrochloride
[6-methoxy-3-[4-[2-(1-piperidinyl)ethoxy]phenoxy]-2-(4-benzyloxyphenyl)]benzo[b]thiophene
[6-methoxy-3-[4-[2-(1-pyrrolidinyl)ethoxy]phenoxy]-2-(4-benzyloxyphenyl)]benzo[b]thiophene
[6-methoxy-3-[4-[2-(1-hexamethyleneimino)ethoxy] phenoxy]-2-(4-benzyloxyphenyl)]benzo[b]thiophene

[6-methoxy-3-[4-[2-(1-N,N-dimethylamino)ethoxy]
  phenoxy]-2-(4-benzyloxyphenyl)]benzo[b]thiophene
[6-methoxy-3-[4-[2-(1-morpholino)ethoxy]phenoxy]-2-(4-
  benzyloxyphenyl)]benzo[b]thiophene
[6-methoxy-3-[4-[2-(1-piperidinyl)ethoxy]phenoxy]-2-(4-
  isopropoxyphenyl)]benzo[b]thiophene
[6-methoxy-3-[4-[2-(1-pyrrolidinyl)ethoxy]phenoxy]-2-(4-
  isopropoxyphenyl)]benzo[b]thiophene
[6-methoxy-3-[4-[2-(1-hexamethyleneimino)ethoxy]
  phenoxy]-2-(4-isopropoxyphenyl)]benzo[b]thiophene
[6-methoxy-3-[4-[2-(1-N,N-dimethylamino)ethoxy]
  phenoxy]-2-(4-isopropoxyphenyl)]benzo[b]thiophene
[6-methoxy-3-[4-[2-(1-morpholino)ethoxy]phenoxy]-2-(4-
  isopropoxyphenyl)]benzo[b]thiophene
[6-methoxy-3-[4-[2-(1-piperidinyl)ethoxy]phenoxy]-2-(4-
  hydroxyphenyl)]benzo[b]thiophene
[6-methoxy-3-[4-[2-(1-pyrrolidinyl)ethoxy]phenoxy]-2-(4-
  hydroxyphenyl)]benzo[b]thiophene
[6-methoxy-3-[4-[2-(1-hexamethyleneimino)ethoxy]
  phenoxy]-2-(4-hydrooxyphenyl)]benzo[b]thiophene
[6-methoxy-3-[4-[2-(1-N,N-dimethylamino)ethoxy]
  phenoxy]-2-(4-hydroxyphenyl)]benzo[b]thiophene
[6-methoxy-3-[4-[2-(1-morpholino)ethoxy]phenoxy]-2-(4-
  hydroxyphenyl)]benzo[b]thiophene
[6-methoxy-3-[4-[2-(1-piperidinyl)ethoxy]phenoxy]-2-(4-
  hydroxyphenyl)]benzo[b]thiophene hydrochloride
[6-methoxy-3-[4-[2-(1-pyrrolidinyl)ethoxy]phenoxy]-2-(4-
  hydroxyphenyl)]benzo[b]thiophene hydrochloride
[6-methoxy-3-[4-[2-(1-hexamethyleneimino)ethoxy]
  phenoxy]-2-(4-hydrooxyphenyl)]benzo[b]thiophene
  hydrochloride
[6-methoxy-3-[4-[2-(1-N,N-dimethylamino)ethoxy]
  phenoxy]-2-(4-hydroxyphenyl)]benzo[b]thiophene
  hydrochloride
[6-methoxy-3-[4-[2-(1-morpholino)ethoxy]phenoxy]-2-(4-
  hydroxyphenyl)]benzo[b]thiophene hydrochloride
[6-benzoyloxy-3-[4-[2-(1-piperidinyl)ethoxy]phenoxy]-2-
  (4-benzoyloxyphenyl)]benzo[b]thiophene hydrochloride
[6-ethylsulfonyloxy-3-[4-[2-(1-piperidinyl)ethoxy]-
  phenoxy]-2-(4-ethylsulfonyloxyphenyl)]benzo[b]
  thiophene hydrochloride
[6-hydroxy-3-[4-[2-(1-piperidinyl)ethoxy]-phenoxy]-2-(4-
  ethylsulfonyloxyphenyl)]benzo[b]thiophene hydrochloride
[6-ethylsulfonyloxy-3-[4-[2-(1-piperidinyl)ethoxy]-
  phenoxy]-2-(4-hydroxyphenyl)]benzo[b]thiophene
  hydrochloride
[6-methoxy-3-[4-[2-(1-piperidinyl)ethoxy]-phenoxy]-2-(4-
  triflouromethanesulfonyloxyphenyl)]benzo[b]thiophene
3-[4-[2-(1-piperidinyl)ethoxy]phenoxy]-2-(4-
  benzoyloxyphenyl)]benzo[b]thiophene hydrochloride
3-[4-[2-(1-piperidinyl)ethoxy]phenoxy]-2-(4-
  pivaloyloxyphenyl)]benzo[b]thiophene hydrochloride
3-[4-[2-(1-piperidinyl)ethoxy]phenoxy]-2-(4-butylsulfonyl-
  oxyphenyl)]benzo[b]thiophene hydrochloride
[6-methoxy-3-[4-[2-(1-piperidinyl)ethoxy]thiophenoxy]-2-
  (4-methoxyphenyl)]benzo[b]thiophene
[6-methoxy-3-[4-[2-(1-pyrrolidinyl)ethoxy]thiophenoxy]-2-
  (4-methoxyphenyl)]benzo[b]thiophene
[6-methoxy-3-[4-[2-(1-hexamethyleneimino)ethoxy]
  thiophenoxy]-2-(4-methoxyphenyl)]benzo[b]thiophene
[6-methoxy-3-[4-[2-(1-N,N-dimethylamino)ethoxy]
  thiophenoxy]-2-(4-methoxyphenyl)]benzo[b]thiophene
[6-methoxy-3-[4-[2-(1-morpholino)ethoxy]thiophenoxy]-2-
  (4-methoxyphenyl)]benzo[b]thiophene
[6-benzyloxy-3-[4-[2-(1-piperidinyl)ethoxy]thiophenoxy]-
  2-(4-methoxyphenyl)]benzo[b]thiophene
[6-benzyloxy-3-[4-[2-(1-pyrrolidinyl)ethoxy]thiophenoxy]-
  2-(4-methoxyphenyl)]benzo[b]thiophene
[6-benzyloxy-3-[4-[2-(1-hexamethyleneimino)ethoxy]
  thiophenoxy]-2-(4-methoxyphenyl)]benzo[b]thiophene
[6-benzyloxy-3-[4-[2-(1-N,N-dimethylamino)ethoxy]
  thiophenoxy]-2-(4-methoxyphenyl)]benzo[b]thiophene
[6-benzyloxy-3-[4-[2-(1-morpholino)ethoxy]thiophenoxy]-
  2-(4-methoxyphenyl)]benzo[b]thiophene
[6-isopropoxy-3-[4-[2-(1-piperidinyl)ethoxy]thiophenoxy]-
  2-(4-methoxyphenyl)]benzo[b]thiophene
[6-isopropoxy-3-[4-[2-(1-pyrrolidinyl)ethoxy]
  thiophenoxy]-2-(4-methoxyphenyl)]benzo[b]thiophene
[6-isopropoxy-3-[4-[2-(1-hexamethyleneimino)ethoxy]-
  thiophenoxy]-2-(4-methoxyphenyl)]benzo[b]thiophene
[6-isopropoxy-3-[4-[2-(1-N,N-dimethylamino)ethoxy]
  thiophenoxy]-2-(4-methoxyphenyl)]benzo[b]thiophene
[6-isopropoxy-3-[4-[2-(1-morpholino)ethoxy]
  thiophenoxy]-2-(4-methoxyphenyl)]benzo[b]thiophene
[6-hydroxy-3-[4-[2-(1-piperidinyl)ethoxy]thiophenoxy]-2-
  (4-methoxyphenyl)]benzo[b]thiophene
[6-hydroxy-3-[4-[2-(1-pyrrolidinyl)ethoxy]thiophenoxy]-2-
  (4-methoxyphenyl)]benzo[b]thiophene
[6-hydroxy-3-[4-[2-(1-hexamethyleneimino)ethoxy]-
  thiophenoxy]-2-(4-methoxyphenyl)]benzo[b]thiophene
[6-hydroxy-3-[4-[2-(1-N,N-dimethylamino)ethoxy]
  thiophenoxy]-2-(4-methoxyphenyl)]benzo[b]thiophene
[6-hydroxy-3-[4-[2-(1-morpholino)ethoxy]thiophenoxy]-2-
  (4-methoxyphenyl)]benzo[b]thiophene
[6-hydroxy-3-[4-[2-(1-piperidinyl)ethoxy]thiophenoxy]-2-
  (4-methoxyphenyl)]benzo[b]thiophene hydrochloride
[6-hydroxy-3-[4-[2-(1-pyrrolidinyl)ethoxy]thiophenoxy]-2-
  (4-methoxyphenyl)]benzo[b]thiophene hydrochloride
[6-hydroxy-3-[4-[2-(1-hexamethyleneimino)ethoxy]-
  thiophenoxy]-2-(4-methoxyphenyl)]benzo[b]thiophene
  hydrochloride
[6-hydroxy-3-[4-[2-(1-N,N-dimethylamino)ethoxy]
  thiophenoxy]-2-(4-methoxyphenyl)]benzo[b]thiophene
  hydrochloride
[6-hydroxy-3-[4-[2-(1-morpholino)ethoxy]thiophenoxy]-2-
  (4-methoxyphenyl)]benzo[b]thiophene hydrochloride
[6-methoxy-3-[4-[2-(1-piperidinyl)ethoxy]thiophenoxy]-2-
  (4-benzyloxyphenyl)]benzo[b]thiophene
[6-methoxy-3-[4-[2-(1-pyrrolidinyl)ethoxy]thiophenoxy]-2-
  (4-benzyloxyphenyl)]benzo[b]thiophene
[6-methoxy-3-[4-[2-(1-hexamethyleneimino)ethoxy]
  thiophenoxy]-2-(4-benzyloxyphenyl)]benzo[b]thiophene
[6-methoxy-3-[4-[2-(1-N,N-dimethylamino)ethoxy]
  thiophenoxy]-2-(4-benzyloxyphenyl)]benzo[b]thiophene
[6-methoxy-3-[4-[2-(1-morpholino)ethoxy]thiophenoxy]-2-
  (4-benzyloxyphenyl)]benzo[b]thiophene
[6-methoxy-3-[4-[2-(1-piperidinyl)ethoxy]thiophenoxy]-2-
  (4-isopropoxyphenyl)]benzo[b]thiophene
[6-methoxy-3-[4-[2-(1-pyrrolidinyl)ethoxy]thiophenoxy]-2-
  (4-isopropoxyphenyl)]benzo[b]thiophene
[6-methoxy-3-[4-[2-(1-hexamethyleneimino)ethoxy]
  thiophenoxy]-2-(4-isopropoxyphenyl)]benzo[b]
  thiophene
[6-methoxy-3-[4-[2-(1-N,N-dimethylamino)ethoxy]
  thiophenoxy]-2-(4-isopropoxyphenyl)]benzo[b]
  thiophene
[6-methoxy-3-[4-[2-(1-morpholino)ethoxy]thiophenoxy]-2-
  (4-isopropoxyphenyl)]benzo[b]thiophene
[6-methoxy-3-[4-[2-(1-piperidinyl)ethoxy]thiophenoxy]-2-
  (4-hydroxyphenyl)]benzo[b]thiophene
[6-methoxy-3-[4-[2-(1-pyrrolidinyl)ethoxy]thiophenoxy]-2-
  (4-hydroxyphenyl)]benzo[b]thiophene
[6-methoxy-3-[4-[2-(1-hexamethyleneimino)ethoxy]
  thiophenoxy]-2-(4-hydroxyphenyl)]benzo[b]thiophene

[6-methoxy-3-[4-[2-(1-N,N-dimethylamino)ethoxy] thiophenoxy]-2-(4-hydroxyphenyl)]benzo[b]thiophene

[6-methoxy-3-[4-[2-(1-morpholino)ethoxy]thiophenoxy]-2-(4-hydroxyphenyl)]benzo[b]thiophene

[6-methoxy-3-[4-[2-(1-piperidinyl)ethoxy]thiophenoxy]-2-(4-hydroxyphenyl)]benzo[b]thiophene hydrochloride

[6-methoxy-3-[4-[2-(1-pyrrolidinyl)ethoxy]thiophenoxy]-2-(4-hydroxyphenyl)]benzo[b]thiophene hydrochloride

[6-methoxy-3-[4-[2-(1-hexamethyleneimino)ethoxy] thiophenoxy]-2-(4-hydroxyphenyl)]benzo[b]thiophene hydrochloride

[6-methoxy-3-[4-[2-(1-N,N-dimethylamino)ethoxy] thiophenoxy]-2-(4-hydroxyphenyl)]benzo[b]thiophene hydrochloride

[6-methoxy-3-[4-[2-(1-morpholino)ethoxy]thiophenoxy]-2-(4-hydroxyphenyl)]benzo[b]thiophene hydrochloride

[6-methoxy-3-[4-[2-(1-piperidinyl)ethoxy]thiophenoxy]-2-(4-methoxyphenyl)]benzo[b]thiophene hydrochloride

[6-hydroxy-3-[4-[2-(1-piperidinyl)ethoxy]thiophenoxy]-2-(4-hydroxyphenyl)]benzo[b]thiophene

[6-hydroxy-3-[4-[2-(l-pyrrolidinyl)ethoxy]thiophenoxy]-2-(4-hydroxyphenyl)]benzo[b]thiophene

[6-hydroxy-3-[4-[2-(1-hexamethyleneimino)ethoxy] thiophenoxy]-2-(4-hydroxyphenyl)]benzo[b]thiophene

[6-hydroxy-3-[4-[2-(1-N,N-dimethylamino)ethoxy] thiophenoxy]-2-(4-hydroxyphenyl)]benzo[b]thiophene

[6-hydroxy-3-[4-[2-(1-morpholino)ethoxy]thiophenoxy]-2-(4-hydroxyphenyl)]benzo[b]thiophene

[6-hydroxy-3-[4-[2-(1-piperidinyl)ethoxy]thiophenoxy]-2-(4-hydroxyphenyl)]benzo[b]thiophene hydrochloride

[6-hydroxy-3-[4-[2-(1-pyrrolidinyl)ethoxy]thiophenoxy]-2-(4-hydroxyphenyl)]benzo[b]thiophene hydrochloride

[6-hydroxy-3-[4-[2-(1 -hexamethyleneimino)ethoxy] thiophenoxy]-2-(4-hydroxyphenyl)]benzo[b]thiophene hydrochloride

[6-hydroxy-3-[4-[2-(1-N,N-dimethylamino)ethoxy] thiophenoxy]-2-(4-hydroxyphenyl)]benzo[b]thiophene hydrochloride

[6-hydroxy-3-[4-[2-(1-morpholino)ethoxy]thiophenoxy]-2-(4-hydroxyphenyl)]benzo[b]thiophene hydrochloride 6-hydroxy-3-[4-[2-(1-piperidinyl)ethoxy]phenoxy]-2-phenyl]benzo[b]thiophene hydrochloride The following examples are presented to further illustrate the preparation of compounds of the present invention. It is not intended that the invention be limited in scope by reason of any of the following examples.

NMR data for the following Examples were generated on a GE 300 MHz NMR instrument, and anhydrous d-6 DMSO was used as the solvent unless otherwise indicated.

Preparation 1

Preparation of [3-[4-[2-(1-piperidinyl)ethoxy] phenoxy]-2-(4-hydroxyphenyl)]benzo[b]thiophene [3-(4-benzyloxy)phenoxy]benzo [b]thiophene

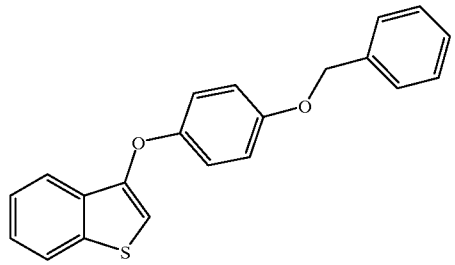

To a solution of 3-bromo-benzo[b]thiophene (69.62 g, 0.325 mol) in 55 mL of anhydrous collidine under $N_2$ was added 4-benzyloxyphenol (97.6 g, 0.488 mol) and cuprous oxide (23.3 g, 0.163 mol). The mixture was heated to reflux for 24 hours. Upon cooling, the reaction mixture was diluted with ethyl acetate (200 mL) and the crude mixture filtered through a pad of Celite® (Aldrich, Milwaukee, Wis.) to remove inorganic salts. The filtrate was washed with 1N hydrochloric acid (3 ×150 mL). The organic was dried (sodium sulfate) and concentrated in vacuo to a liquid. Thianaphthene was removed by distillation (10 mm Hg, 115–120° C.). The remainder of the material was chromatographed (silicon dioxide, hexanes: ethyl acetate 85:15) to provide 12.2 g of benzo[b]thiophene and 12.95 g (35% based on recovered starting material) of [3-(4-benzyloxy) phenoxy]benzo-[b]thiophene as an off-white solid. mp 84–86° C. $^1$H NMR (CDCl$_3$) d 7.91–7.83 (m, 2H), 7.47–7.34 (m, 7H), 7.04 (q, $J_{AB}$=9.0 Hz, 4H), 6.47 (s, 1H), 5.07 (s, 2H). Anal. calcd. for $C_{21}H_{16}O_2S$: C, 75.88; H, 4.85. Found: C, 75.75; H, 5.00.

Preparation 2

(2-Iodo-3-(4-benzyloxy)phenoxy]benzo-[b] thiophene

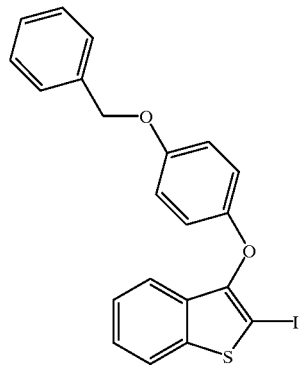

To a solution of [3-(4-benzyloxy)phenoxy]benzo[b]thiophene (6.00 g, 18.1 mmol) in anhydrous tetrahydrofuran (100 mL) under $N_2$ at −78° C. was added n-butyllithium (12.4 mL, 19.9 mmol, 1.6M in hexanes) dropwise via syringe. The solution turned from colorless to deep orange. After stirring for 20 minutes at −78° C., the lithio species was treated with $I_2$ (5.03, 19.9 mmol), added dropwise via canula as a solution in 50 mL of anhydrous tetrahydrofuran. Upon completion of the addition, the reaction turned light yellow in color, and was allowed to slowly warm to room temperature. The reaction was quenched by the addition of 0.1N sodium sulfite solution (200 mL). The layers were separated and the aqueous extracted with ethyl acetate (2×150 mL). The organic was combined, dried (sodium sulfate), and concentrated in vacuo to give an oil that crystallized on standing. Recrystallization from hexanes/ethyl ether yielded 7.10 g (86%) of [2-Iodo-3-(4-benzyloxy)phenoxy]benzo[b]thiophene as a white crystalline powder. mp 87–92° C. $^1$H NMR ($CDCl_3$) d 7.72 (d, J=8.1 Hz, 1H), 7.47–7.20 (m, 8H), 6.89 (s, 4H), 5.01 (s, 2H). Anal. Calcd. for $C_{21}H_{15}O_2SI$: C, 55.03; H, 3.30. Found: C, 55.29; H, 3.31.

Preparation 3

[2-(4-tertbutyloxyphenyl)-3-(4-benzyloxy)phenoxy]benzo[b]thiophene

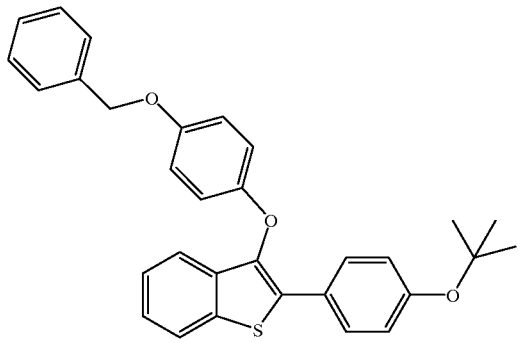

To a solution of [2-Iodo-3-(4-benzyloxy)phenoxy]-benzo[b]thiophene (4.50 g, 9.82 mmol) in toluene (20 mL) was added 4-(tertbutoxy)phenyl boronic acid (2.28 g, 11.75 mmol) followed by tetrakistriphenylphosphinepalladium (0.76 g, 0.66 mmol). To this solution was added 14.5 mL of 2N sodium carbonate solution. The resulting mixture was heated to reflux for 3 hours. Upon cooling, the reaction was diluted with 150 mL of ethyl acetate. The organic was washed with 0.1N sodium hydroxide (2×100 mL) and then dried (sodium sulfate). Concentration produced a semi-solid that was dissolved in chloroform and passed through a pad of silicon dioxide. Concentration produced an oil that was triturated from hexanes to yield 4.00 g (91%) of [2-(4-tertbutyloxy-phenyl)-3-(4-benzyloxy)phenoxy]benzo[b]thiophene as a white powder. mp 105–108° C. $^1$H NMR ($CDCl_3$) d 7.77 (d, J=7.7 Hz, 1H), 7.68 (d, J=8.6 Hz, 2H), 7.43–7.24 (m, 8H), 6.98 (d, J =8.6 Hz, 2H), 6.89 (q, $J_{AB}$=9.3 Hz, 4H), 4.99 (s, 2H), 1.36 (s, 9H). FD mass spec: 480. Anal. Calcd. for $C_{31}H_{28}O_3S$: C, 77.47; H, 5.87. Found: C, 77.35; H, 5.99.

Preparation 4

Prepared in a similar manner employing 4-methoxyphenylboronic acid was [2-(4-methoxyphenyl)-3-(4-benzyloxy)phenoxy]benzo[b]-thiophene

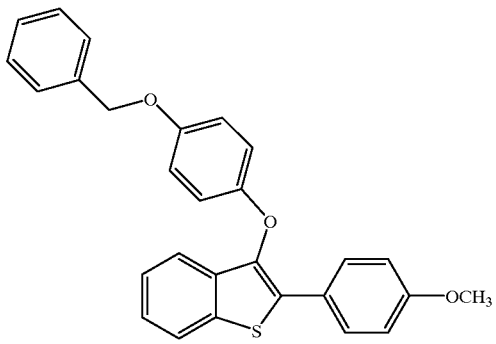

Yield=73%. mp=115–118° C. $^1$H NMR ($CDCl_3$) d 7.80–7.90 (m, 3H), 7.33–7.53 (m, 8H), 6.93–7.06 (m, 6H), 5.00 (s, 2H), 3.83 (s, 3H). FD mass spec: 438. Anal. Calcd. for $C_{28}H_{22}O_3S$: C, 76.69; H, 5.06. Found: C, 76.52; H, 5.09.

Preparation 5

[2-(4-tertbutyloxyphenyl)-3-(4-hydroxy)phenoxy]benzo[b]thiophene

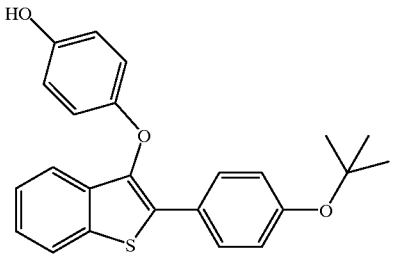

To a solution of [2-(4-tertbutyloxyphenyl)-3-(4-benzyloxy)phenoxy]benzo[b]thiophene (1.50 g, 3.37 mmol) in 30 mL of absolute ethanol containing 1% concentrated hydrochloric acid was added 0.50 g of 10% palladium-on-carbon. The mixture was hydrogenated at 40 psi for 1 hour, after which the reaction was judged to be complete by thin layer chromatography. The mixture was filtered through a pad of Celite, and the filtrate concentrated in vacuo. The crude product was dissolved in minimal ethyl acetate and passed through a short silicon dioxide column to remove Celite (ethyl acetate as eluant). Concentration provided a white solid that was triturated from hexanes/ethyl ether. Filtration provided 868 mg (73%) of [2-(4-tertbutyloxy-phenyl) -3-(4-hydroxy)phenoxy]-benzo[b]thiophene. mp 210–213° C. $^1$H NMR (DMSO-$d_6$) d 9.13 (s, 1H), 7.94 (d, J=7.7 Hz, 1H), 7.63 (d, J=8.6 Hz, 2H), 7.35–7.26 (m, 3H), 7.01 (d, J =8.6 Hz, 2H), 6.70 (q, $J_{AB}$=8.9 Hz, 4H), 1.28 (s, 9H). FD mass spec: 390. Anal. Calcd. for $C_{24}H_{22}O_3S$: C, 73.82; H, 5.68. Found: C, 73.98; H, 5.84.

Preparation 6

Prepared in a similar manner was [2-(4-methoxyphenyl)-3-(4-hydroxy)phenoxy]benzo[b]thiophene

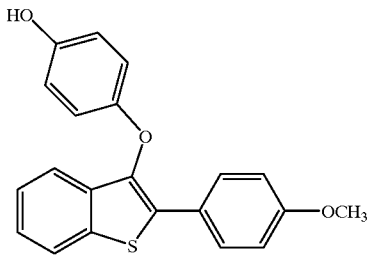

Yield=80%. mp =120–1250° C. $^1$H NMR (CDCl$_3$) d 7.80–7.90 (m, 3H), 7.48 (m, 1H), 7.30–7.48 (m, 2H), 6.90–7.03 (m, 4H), 6.76–6.86 (m, 2H), 3.82 (s, 3H). FD mass spec: 348; Anal Calcd. for C$_{21}$H$_{16}$O$_3$S: C, 72.39; H, 4.63. Found: C, 72.68; H, 4.82.

EXAMPLE 1

[3-[4-[2-(1-piperidinyl)ethoxy]phenoxy]-2-(4-hydroxyphenyl)]benzo[b]thiophene

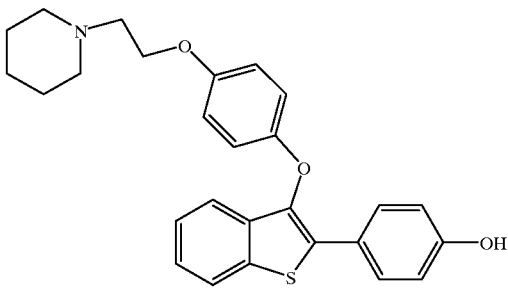

To a solution of [2-(4-tertbutyloxyphenyl)-3-(4-hydroxy)phenoxy]benzo[b]thiophene (1.25 g, 3.20 mmol) in anhydrous N,N-dimethylformamide (10 mL) at ambient temperature was added cesium carbonate (5.70 g, 17.6 mmol). After stirring for 20 minutes, 2-chloroethylpiperidine hydrochloride (1.95 g, 10.56 mmol) was added in small portions. The resulting heterogeneous mixture was stirred vigorously for 24 hours. The contents of the reaction were then diluted with water (200 mL). The aqueous phase was extracted with ethyl acetate (3×100 mL). The combined organic layer was then washed with water (2×200 mL). Drying of the organic layer (sodium sulfate) and concentration in vacuo gave an oil. Chromatography (5–10% methanol/chloroform) provided 1.47 g (91%) of 3-[4-[2-(1-piperidinyl)ethoxy]phenoxy]-2-(4-tertbutyloxyphenyl)]benzo[b]-thiophene that was carried on directly to the next step without characterization.

3-[4-[2-(1-piperidinyl)ethoxy]phenoxy]-2-(4-tertbutyloxy-phenyl)]benzo[b]thiophene (1.37 g, 2.73 mmol) was dissolved in triflouroacetic acid (10 mL) at ambient temperature. After stirring for 15 minutes, the solvent was removed in vacuo. The residue was dissolved in ethyl acetate (20 mL) and washed with sat. sodium bicarbonate solution (3×10 mL). The organic layer was dried (sodium sulfate) and concentrated whereupon a white solid precipitated formed in solution. The product was recrystallized from ethyl acetate-ethyl ether to provide 1.03 g (85%) of 3-[4-[2-(1-piperidinyl)ethoxy]phenoxy]-2-(4-hydroxyphenyl) ]benzo[b]-thiophene as colorless crystals. mp 169–172° C. $^1$H NMR (DMSO-d$_6$) d 9.81 (s, 1H), 7.93 (d, J=7.7 Hz, 1H), 7.54 (d, J =8.5 Hz, 2H), 7.36–7.26 (m, 3H), 6.86 (s, 4H), 6.78 (d, J=8.6 Hz, 2H), 4.10 (m, 2H), 3.29 (m, 2H), 2.95–2.75 (m, 4H), 1.68–1.40 (m, 6H). Anal. Calcd. for C$_{27}$H$_{27}$NO$_3$S.0.55 CF$_3$CO$_2$H: C, 66.40; H, 5.46; N, 2.76. Found: C, 65.99; H, 5.49; N, 2.61

EXAMPLE 2

3-[4-[2-(1-piperidinyl)ethoxy]phenoxy]-2-(4-hydroxyphenyl)]benzo[b]thiophene was converted to its hydrochloride salt in 90% yield by treatment with ethyl ether-hydrochloric acid in ethyl acetate

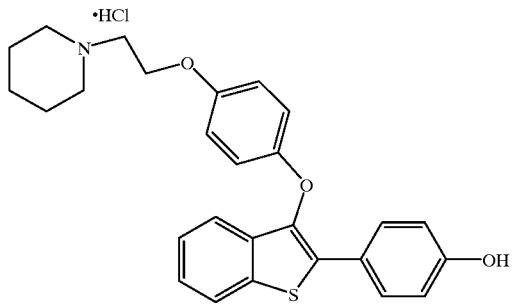

Data for Example 2 mp 233–240° C. $^1$H NMR (DMSO-d$_6$) d 10.43 (m, 1H), 9.89 (s, 1H), 7.93–7.95 (m, 1H), 7.60–7.64 (m, 2H), 7.35–7.50 (m, 3H), 6.83–7.03 (m, 6H), 4.27–4.30 (m, 2H), 3.40–3.60 (m, 4H), 2.96–3.10 (m, 2H), 1.70–1.95 (m, 5H), 1.40–1.53 (m, 1H). FD mass spec: 446. Anal. Calcd. for C27H$_{27}$NO$_3$S.1.0HCl: C, 67.28; H, 5.86; N, 2.91. Found: C, 67.07; H, 5.66; N, 2.96.

EXAMPLE 3

Prepared in an analogous manner were the following examples:

[3-[4-[2-(1-pyrolidinyl)ethoxy]phenoxy]-2-(4-hydroxyphenyl)]benzo[b]thiophene

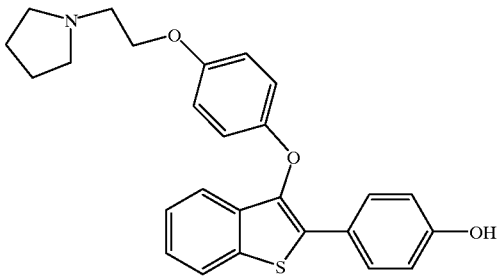

mp 150–155° C. $^1$H NMR (DMSO-d$_6$) d 9.79 (s, 1H), 7.92 (d, J=7.8 Hz, 1H), 7.54 (d, J=8.6 Hz, 2H), 7.36–7.26 (m, 3H), 6.84 (S, 4H), 6.78 )d, J=8.6 Hz, 2H), 4.00 (bt, 2H), 2.92 (m, 2H), 2.85 (m, 4H), 1.73 (m, 4H). Anal. Calcd. for C$_{26}$H$_{25}$NO$_3$S.0.33 CF$_3$CO$_2$H: C, 68.25; H, 5.44; N, 2.99. Found: C, 68.29; H, 5.46; N, 3.19.

EXAMPLE 4

[3-[4-[2-(1-hexamethyleneimino)ethoxy]phenoxy]-2-(4-hydroxyphenyl)]benzo[b]thiophene

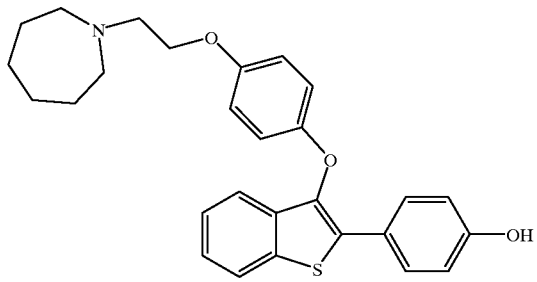

mp 189–191° C. $^1$H NMR (DMSO-d6) d 7.91 (d, J=7.6 Hz, 1H), 7.52 (d, J=8.5 Hz, 2H), 7.34–7.25 (m, 3H), 6.81 (s, 4H), 6.75 (d, J=8.6 Hz, 2H), 3.89 (bt, 2H), 2.75 (bt, 2H), 2.68 (m, 4H), 1.48 (m, 8H). Anal. Calcd. for $C_{28}H_{29}NO_3S \cdot 1.50H_2O$: C, 69.11; H, 6.79; N, 2.88. Found: C, 69.25; H, 6.79; N, 2.58.

EXAMPLE 5

[3-[4-[2-(1-N,N-diethylamino)ethoxy]phenoxy]-2-(4-hydroxyphenyl)]benzo[b]thiophene

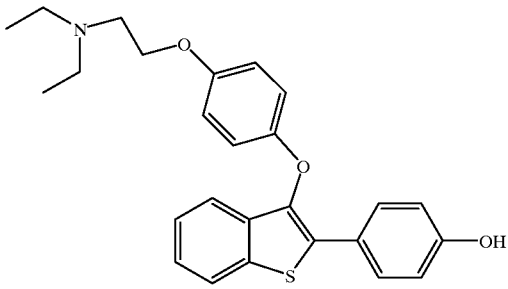

mp 70° C. $^1$H NMR (DMSO-d$_6$) d 9.91 (bs, 1H), 7.92 (d, J=7.9 Hz, 1H), 7.54 (d, J=8.6 Hz, 2H), 7.35–7.24 (m, 3H), 6.82 (s, 4H), 6.78 (d, J=8.6 Hz, 2H), 3.88 (bt, 2H), 2.76 (bt, 2H), 2.51 (m, 4H), 0.91 (m, 6H). FD mass spec: 434. Anal. Calcd. for $C_{26}H_{27}NO_3S \cdot 0.50\ H_2O$: C, 70.56; H, 6.38; N, 3.16 Found: C, 70.45; H, 6.26; N, 3.20.

EXAMPLE 6

3-[4-[2-(1-piperidinyl)ethoxy]phenoxy]-2-(4-methoxyphenyl)]benzo[b]thiophene hydrochloride

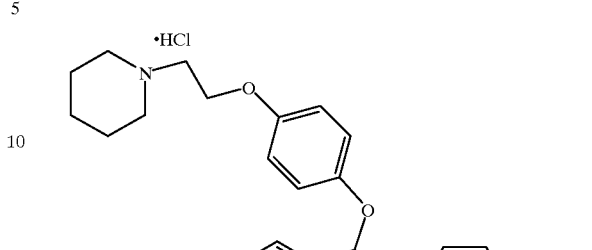

mp=228–230° C. $^1$H NMR (DMSO-d$_6$) d 7.96 (d, J=7.5 Hz, 1H), 7.66 (d, J=8.8 Hz, 2H), 7.35–7.50 (m, 3H), 6.98 (d, J =8.7 Hz, 2H), 6.86–6.90 (m, 4H), 4.28–4.31 (m, 2H), 3.74 (s, 3H), 3.37–3.45 (m, 4H), 2.92–2.96 (m, 2H), 2.46–2.48 (m, 5H), 1.74 (m, 1H). FD mass spec: 459. Anal Calcd. for $C_{28}H_{29}NO_3S \cdot 1.0HCl$: C, 67.80; H, 6.10; N, 2.82. Found: C, 68.06; H, H, 6.38; N, 2.60.

Alternate Synthesis of [2-(4-tertbutyloxyphenyl)-3-(4-benzyloxy)phenoxy]benzo[b]thiophene Preparation 7

[3-(4-benzyloxy)phenoxy]benzo[b]thiophene-2-boronic acid

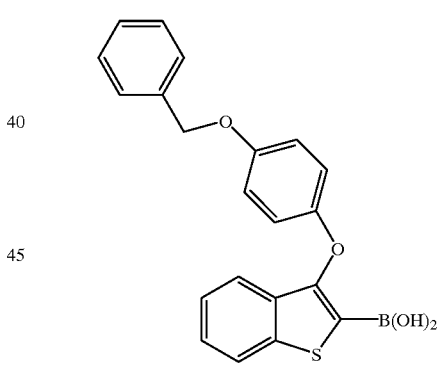

To a –78° C. solution of [3-(4-benzyloxy)phenoxy]benzo[b]-thiophene (5.00 g, 15.1 mmol) in 20 mL of anhydrous tetrahydrofuran under $N_2$ was added n-butyllithium (9.90 mL, 15.8 mmol, 1.6M in hexanes) dropwise via syringe. After stirring for 15 minutes, B(OiPr)$_3$ (3.83 mL, 16.6 mmol) was added via syringe, and the resulting mixture was allowed to warm to 0° C. The reaction was then quenched by distributing between ethyl acetate and 1.0N hydrochloric acid (100 mL each). The layers were separated and the organic was extracted with water (1×100 mL). The organic layer was dried (sodium sulfate) and concentrated in vacuo to a solid that was triturated from ethyl ether/hexanes. Filtration provided 3.96 g (70%) of [3-(4-benzyloxy)phenoxy]benzo[b]thiophene-2-boronic acid as a white solid.

mp 115–121° C. ¹H NMR (DMSO-$d_6$) d 8.16 (d, J=8.5 Hz, 1H), 7.98 (d, J=9.0 Hz, 1H), 7.42–7.23 (m, 7H), 6.90 (q, $J_{AB}$=9.0 Hz, 4H), 5.01 (s, 2H). Anal. Calcd. for $C_{21}H_{17}O_4SB$: C, 67 04; H, 4.55. Found: C, 67.17; H, 4.78.

[3-(4-Benzyloxy)phenoxy]benzo[b]thiophene-2-boronic acid was reacted with 4-(-tertbutoxy)bromobenzene according to the conditions described above for [2-iodo-3-(4-benzyloxy) phenoxy]-benzo[b]thiophene and 4-(tertbutoxy) phenyl boronic acid to give [2-(4-tertbutyloxyphenyl)-3-(4-benzyloxy)phenoxy]benzo[b]thiophene in 81% yield.

Examples prepared by employing this method are:

EXAMPLE 7

[3-[4-[2-(1-piperidinyl)ethoxy]phenoxy]-2-(phenyl)] benzo [b]thiophene hydrochloride

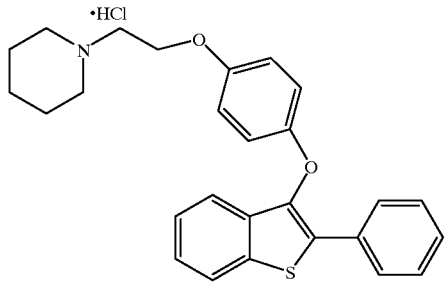

mp 223–226° C. ¹H NMR (DMSO-$d_6$) d 7.99 (d, J=8.2 Hz, 1H), 7.71 (d, J=7.3 Hz, 1H), 7.44–7.30 (m, 7H), 6.90 (s, 4H), 4.27 (m, 2H), 3.43–3.35 (m, 4H), 2.97–2.88 (m, 2H), 1.73–1.61 (m, 5H), 1.34 (m, 1H). Anal. Calcd. for $C_{27}H_{27}NO_2S.1.0$ HCl: C, 69.59; H, 6.06; N, 3.00. Found: C, 69.88; H, 6.11; N, 3.19.

EXAMPLE 8

[3-[4-[2-(1-piperidinyl)ethoxy]phenoxy]-2-(4-flourophenyl)]benzo[b]thiophene

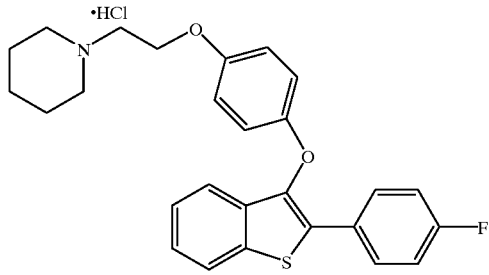

mp 219–226° C. ¹H NMR (DMSO-$d_6$) d 10.20 (bs, 1H), 7.99 (d, J=8.2 Hz, 1H), 7.77–7.73 (m, 4H), 7.42–7.25 (m, 5H), 6.90 (s, 4H), 4.27 (m, 2H), 3.44–3.31 (m, 4H), 2.96–2.89 (m, 2H), 1.78–1.61 (m, 5H), 1.34 (m, 1H). FD mass spec: 447. Anal. Calcd. for $C_{27}H_{26}NO_2SF.1.0$ HCl: C, 67.00; H, 5.62; N, 2.89. Found: C, 67.26; H, 5.67; N, 3.03.

Preparation 8

Synthesis of [6-Hydroxy-3-[4-[2-(1-piperidinyl) ethoxy]-phenoxy]-2-(4-hydroxyphenyl)]benzo[b] thiophene

[6-methoxy-2-(4-methoxyphenyl)-3-bromo]benzo-[b]thiophene

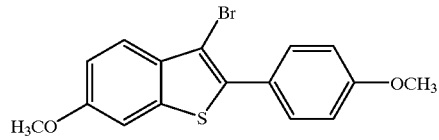

To a solution of [6-methoxy-2-(4-methoxyphenyl)]benzo [b]thiophene (27.0 g, 100 mmol) in 1.10 L of chloroform at 60° C. was added bromine (15.98 g, 100 mmol) dropwise as a solution in 200 mL of chloroform. After the addition was complete, the reaction was cooled to room temperature, and the solvent removed in vacuo to provide 34.2 g (100%) of [6-methoxy-2-(4-methoxyphenyl)-3-bromo]benzo[b] thiophene as a white solid. mp 83–85° C. ¹H NMR (DMSO-$d_6$) d 7.70–7.62 (m, 4H), 7.17 (dd, J=8.6, 2.0 Hz, 1H), 7.09 (d, J=8.4 Hz, 2H). FD mass spec: 349, 350. Anal. Calcd. for $C_{16}H_{13}O_2SBr$: C, 55.03; H, 3.75. Found: C, 54.79; H, 3.76.

EXAMPLE 9

[6-methoxy-2-(4-methoxyphenyl)-3-(4-benzyloxy) phenoxy]-benzo[b]thiophene

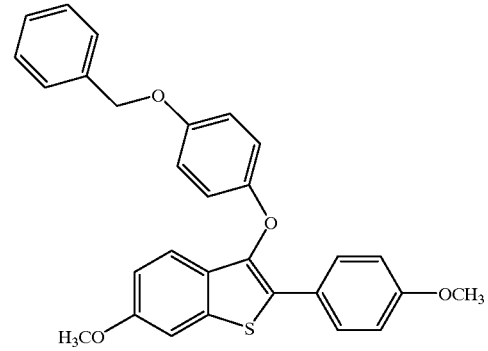

To a solution of [6-methoxy-2-(4-methoxyphenyl)-3-bromo]benzo[b]thiophene (34.00 g, 97.4 mmol) in 60 mL of collidine under $N_2$ was added 4-benzyloxyphenol (38.96 g, 194.8 mmol) and cuprous oxide (14.5 g, 97.4 mmol). The resultant mixture was heated to reflux for 48 hours. Upon cooling to room temperature, the mixture was dissolved in acetone (200 mL), and the inorganic solids were removed by filtration. The filtrate was concentrated in vacuo, and the residue dissolved in methylene chloride (500 mL). The methylene chloride solution was washed with 3N hydrochloric acid (3×300 mL), followed by 1N sodium hydroxide (3×300 mL). The organic layer was dried (sodium sulfate), and concentrated in vacuo. The residue was taken up in 100 mL of ethyl acetate whereupon a white solid formed that was collected by filtration [recovered [6-methoxy-2-(4-methoxyphenyl)]benzo-[b]thiophene (4.62 g, 17.11 mmol]. The filtrate was concentrated in vacuo, and then passed through a short pad of silica gel (methylene chloride as eluant) to remove baseline material. The filtrate was concentrated in vacuo, and the residue crystallized from hexanes/ethyl acetate to provide initially 7.19 g of [6-methoxy-2-(4-methoxyphenyl)-3-(4-benzyloxy) phenoxy]benzo[b]-thiophene as an off-white crystalline solid. The mother liquor was concentrated and chromatographed on silica gel (hexanes/ethyl acetate 80:20) to provide an additional 1.81 g of product. Total yield of [6-methoxy-2-(4-methoxyphenyl)-3-(4-benzyloxy) phenoxy]-benzo[b]thiophene was 9.00 g (24% based on recovered starting material). The basic extract was acidified to pH=4 with 5N hydrochloric acid, and the resultant precipitate collected by filtration and dried to give 13.3 g of recovered 4-benzyloxyphenol. mp 100–103° C. $^1$H NMR (CDCl$_3$): d 7.60 (d, J =8.8 Hz, 2H), 7.39–7.24 (m, 7H), 6.90–6.85 (m, 7H), 4.98 (s, 2H), 3.86 (s, 3H) 3.81 (s, 3H). FD mass spec: 468. Anal. Calcd. for C$_{29}$H$_{24}$O$_4$S: C, 74.34; H, 5.16. Found: C, 74.64; H, 5.29.

Preparation 9

[6-methoxy-2-(4-methoxyphenyl)-3-(4-hydroxy)- phenoxy]benzo[b]thiophene

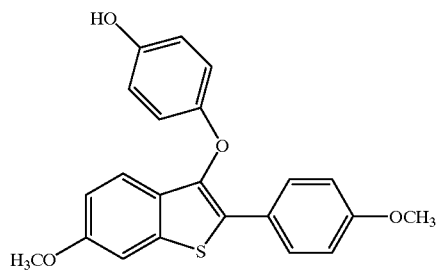

To a solution of [6-methoxy-2-(4-methoxyphenyl)-3-(4-benzyloxy)phenoxy]benzo[b]thiophene (1.50 g, 3.20 mmol) in 50 mL of ethyl acetate and 10 mL of 1% concentrated hydrochloric acid in ethanol was added 10% palladium-on-carbon (300 mg). The mixture was hydrogenated at 40 psi for 20 minutes, after which time the reaction was judged complete by thin layer chromatography. The mixture was passed through Celite to remove catalyst, and the filtrate concentrated in vacuo to a white solid. The crude product was passed through a pad of silica gel (chloroform as eluant). Concentration provided 1.10 g (91%) of [6-methoxy-2-(4-methoxyphenyl)-3-(4-hydroxy)phenoxy] benzo[b]-thiophene as a white solid. mp 123–126° C. $^1$H NMR (DMSO-d$_6$) d 9.10 (s, 1H), 7.59 (d, J=8.8 Hz, 2H), 7.52 (d, J=2.1 Hz, 1H), 7.14 (d, J=8.8 Hz, 1H), 6.95 (d, J=8.8 Hz, 2H), 6.89 (dd, J=8.8, 2.1 Hz, 1H), 6.72 (d, J=9.0 Hz, 2H), 6.63 (d, J=9.0 Hz, 2H), 3.78 (s, 3H), 3.72 (s, 3H). FD mass spec: 378. Anal. Calcd. for C$_{22}$H$_{18}$O$_4$S: C, 69.82; H, 4.79. Found: C, 70.06; H, 4.98.

EXAMPLE 10

[6-methoxy-3-[4-[2-(1-piperidinyl)ethoxy]- phenoxy]-2-(4-methoxyphenyl)]benzo[b]thiophene.

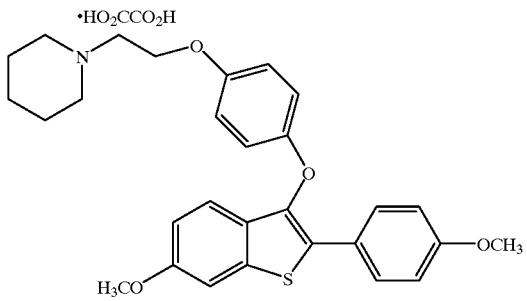

To a solution of [6-methoxy-2-(4-methoxyphenyl)-3-(4-hydroxy)phenoxy]benzo[b]thiophene (1.12 g, 2.97 mmol) in 7 mL of anhydrous N,N-dimethylformamide under N$_2$ was added cesium carbonate (3.86 g, 11.88 mmol). After stirring for 10 minutes, 2-chloroethylpiperidine hydrochloride (1.10 g, 1.48 mmol) was added. The resultant mixture was stirred for 18 hours at ambient temperature. The reaction was the distributed between chloroform/water (100 mL each). The layers were separated and the aqueous extracted with chloroform (3×50 mL). The organic was combined and washed with water (2×100 mL). Drying of the organic (sodium sulfate) and concentration provided an oil that was chromatographed on silica gel (2% methanol/chloroform). The desired fractions were concentrated to an oil that was dissolved in 10 mL of ethyl acetate and treated with oxalic acid (311 mg, 3.4 mmol). After stirring for 10 minutes, a white precipitate formed and was collected by filtration and dried to provide 1.17 g (70%) overall of [6-methoxy-3-[4-[2-(1-piperidinyl)ethoxy]-phenoxy]-2-(4-methoxyphenyl)] benzo[b]thiophene as the oxalate salt. mp 197–200° C. (dec). $^1$H NMR (DMSO-d$_6$) d 7.60 (d, J=8.7 Hz, 2H), 7.55 (d, J=1.1 Hz, 1H), 7.14 (d, J=8.8 Hz, 1H), 7.06 (d, J=8.8 Hz, 2H), 6.91 (dd, J=8.8, 1.1 Hz, 1H), 6.87 (s, 4H), 4.19 (broad t, 2H), 3.78 (s, 3H), 3.72 (s, 3H), 3.32 (broad t, 2H), 3.12–3.06 (m, 4H), 1.69–1.47 (m, 4H), 1.44–1.38 (m, 2H). FD mass spec: 489. Anal. Calcd. for C$_{29}$H$_{31}$NO$_4$S.0.88 HO$_2$CCO$_2$H: C, 64.95; H, 5.80; N, 2.46. Found: C, 64.92; H, 5.77; N, 2.54.

EXAMPLE 11

Treatment of free base with ethyl ether- hydrochloric acid provided [6-methoxy-3-f4-[2-(1- piperidinyl)ethoxy]l-phenoxy]-2-(4- methoxyphenyl)]benzo[b]thiophene hydrochloride

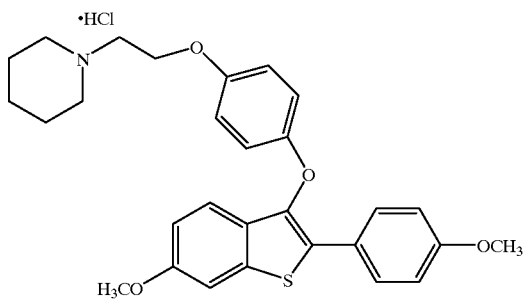

mp 216–220° C. $^1$H NMR (DMSO-d$_6$) d 10.20 (bs, 1H), 7.64 (d, J=8.7 Hz, 2H), 7.59 (d, J=1.5 Hz, 1H), 7.18 (d, J=9.0 Hz, 1H), 7.00 (d, J=8.7 Hz, 1H), 6.96 (dd, J=9.0, 1.5 Hz, 1H), 6.92 (q, J$_{AB}$=9.0 Hz, 4H), 4.31 (m, 2H), 3.83 (s, 3H), 3.77 (s, 3H), 3.43 (m, 4H), 2.97 (m, 2H), 1.77 (m, 5H), 1.37 (m, 1H). FD mass spec: 489 . Anal. Calcd. for C$_{29}$H$_{31}$NO4S.1.0 HCl: C, 66.21; H, 6.13; N, 2.66. Found: C, 66.,46; H, 6.16; N, 2.74.

Prepared in an analogous manner were the following examples:

EXAMPLE 12

[6-Methoxy-3-[4-[2-(1-pyrolodinyl)ethoxy]phenoxy]-2-(4-methoxyphenyl)]benzo[b]thiophene

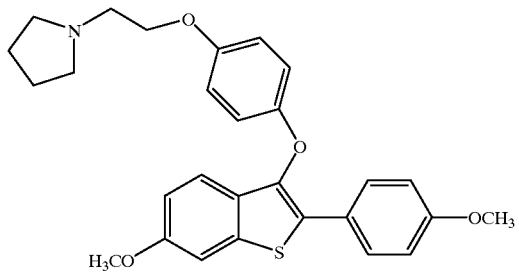

mp 95–98° C. $^1$H NMR (DMSO-d$_6$) d 7.64 (d, J=9.0 Hz, 2H), 7.58 (d, J=2.0 Hz, 1H), 7.18 (d, J=9.0 Hz, 1H), 7.00 (d, J=9.0 Hz, 2H), 6.94 (dd, J=9.0, 2.0 Hz, 1H), 6.86 (s, 4H), 3.97 (t, J=6.0 Hz, 2H), 3.83 ( s, 3H), 3.76 (s, 3H), 2.73 (t, J=6.0 Hz, 2H), 2.51 (m, 4H), 1.66 (m, 4H). FD mass spec: 477. Anal. Calcd. for C$_{28}$H$_{29}$NO$_4$S: C, 70.71; H, 6.15; N, 2.99. Found: C, 70.59; H, 6.15; N, 3.01.

EXAMPLE 13

[6-Methoxy-3-[4-[2-(1-hexamethyleneimino)ethoxy]phenoxy]-2-(4-methoxyphenyl)]benzo[b]thiophene hydrochloride

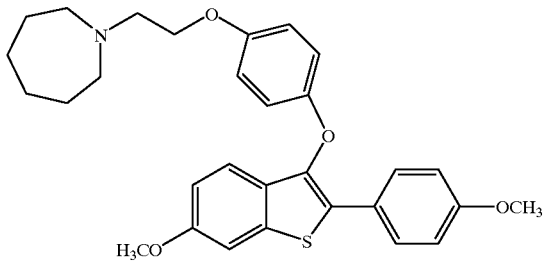

mp 189–192° C. $^1$H NMR (DMSO-d$_6$) d 10.55 (bs, 1H), 7.64 (d, J=9.0 Hz, 2H), 7.58 (d, J=2.0 Hz, 1H), 7.19 (d, J=9.0 Hz, 1H), 7.00 (d, J=9.0 Hz, 2H), 6.95 (dd, J=9.0, 2.0 Hz, H), 6.86 (s, 4H), 3.94 (t, J=6.0 Hz, 2H), 3.83 (s, 3H), 3.76 (s, 3H), 2.80 (t, J=6.0 Hz, 2H), 2.66 (m, 4H), 1.53 (m, 8H). Anal. Calcd. for C$_{30}$H$_{33}$NO$_4$S.1.0 HCl: C, 66.71; H, 6.35; N, 2.59. Found: C, 66.43; H, 6.46; N, 2.84.

EXAMPLE 14

[6-Methoxy-3-[4-[2-(1-N,N-diethylamino)ethoxy]phenoxy]-2-(4-methoxyphenyl)]benzo[b]thiophene hydrochloride

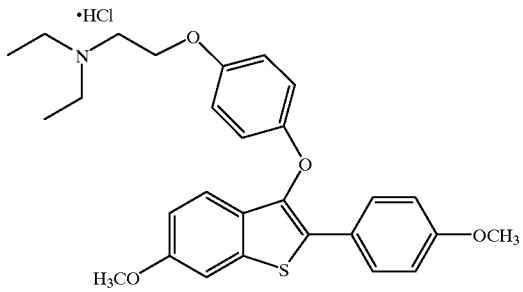

mp 196–198°C. $^1$H NMR (DMSO-d6) d 10.48 (bs, 1H), 7.64 (d, J=9.0 Hz, 2H), 7.59 (d, J=2.0 Hz, 1H), 7.19 (d, J=9.0 Hz, 1H), 7.00 (d, J=9.0 Hz, 2H), 6.97 (dd, J=9.0, 2.0 Hz, 1H), 6.87 (q, J$_{AB}$=9.0 Hz, 4H), 4.25 (m, 2H), 3.83 (s, 3H), 3.77 (s, 3H), 3.54 (m, 2H), 3.09 (m, 4H), 2.00 (m, 3H), 1.88 (m, 3H). Anal. Calcd. for C$_{28}$H$_{31}$NO$_4$S.1.5 HCl:C, 63.18; H, 6.15; N, 2.63. Found: C, 63.46; H, 5.79; N, 2.85.

EXAMPLE 15

[6-Methoxy-3-[4-[2-(morpholino)ethoxy]phenoxy]-2-(4-methoxyphenyl)]benzo[b]thiophene hydrochloride

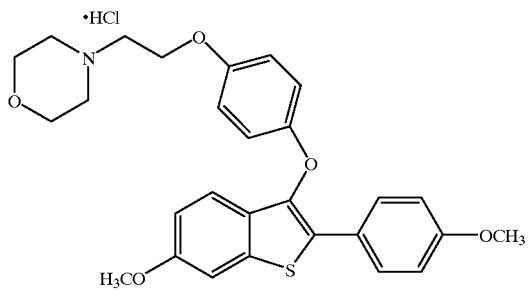

mp 208–211° C. $^1$H NMR (DMSO-d$_6$) d 10.6 (bs, 1H), 7.63 (d, J=9.0 Hz, 2H), 7.60 (d, J=2.0 Hz, 1H), 7.20 (J=9.0 Hz, 1H), 7.00 (d, J=9.0 Hz, 2H), 6.97 (dd, J=9.0, 2.0 Hz, 1H), 6.91 (q, J$_{AB}$=9.0 Hz, 4H), 4.29 (m, 2H), 4.08–3.91 (m, 4H), 3.82 (s, 3H), 3.77 (s, 3H), 3.59–3.42 (m, 4H), 3.21–3.10 (m, 2H). Anal. Calcd. for C$_{28}$H$_{29}$NO$_5$S.1.0 HCl: C, 63.09; H, 5.73; N, 2.65. Found: C, 63.39; H, 5.80; N, 2.40.

EXAMPLE 16

[6-Methoxy-3-[4-[3-(piperidino)propoxy]phenoxy]-2-(4-methoxyphenyl)]benzo[b]thiophene hydrochloride

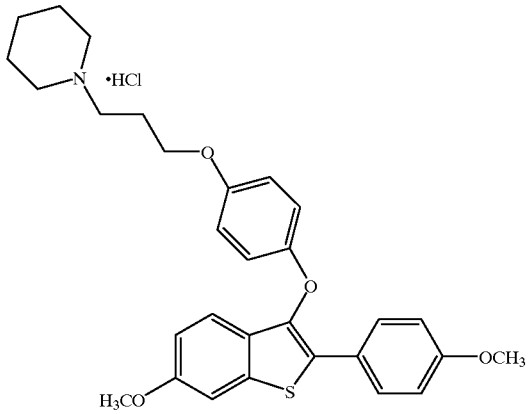

mp 195–200° C. $^1$H NMR (DMSO-$d_6$) d 9.90 (bs, 1H), 7.64 (d, J=9.0 Hz, 2H), 7.59 (d, J=2.0 Hz, 1H), 7.18 (d, J=9.0 Hz, 1H), 7.00 (d, J=9.0 Hz, 2H), 6.95 (dd, J=9.0, 2.0 Hz, 1H), 6.88 (s, 4H), 3.97 (t, J=6.0 Hz, 2H), 3.83 (s, 3H), 3.77 (s, 3H), 3.44 (m, 2H), 3.15 (m, 2H), 2.87 (m, 2H), 2.12 (m, 2H), 1.77 (m, 5H), 1.39 (m, 1H). Anal. Calcd. for $C_{30}H_{33}NO_4S.1.15$ HCl: C, 66.01; H, 6.40; N, 2.73. Found: C, 66.01; H, 6.40; N, 2.73.

EXAMPLE 17

[6-Methoxy-3-[4-[3-(1-N,N-diethylamino)propoxy]phenoxy]-2-(4-methoxyphenyl)]benzo[b]thiophene hydrochloride

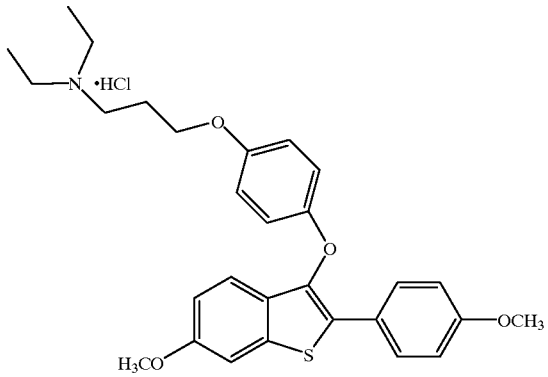

mp 164–166° C. $^1$H NMR (DMSO-$d_6$) d 9.77 (bs, 1H), 7.64 (d, J=9.0 Hz, 2H), 7.59 (d, J=2.0 Hz, 1H), 7.18 (d, J=9.0 Hz, 1H), 7.00 (d, J=9.0 Hz, 2H), 6.95 (dd, J=9.0, 2.0 Hz, 1H), 6.89 (s, 4H), 3.99 (t, J=6.0 Hz, 2H), 3.83 (s, 3H), 3.77 (s, 3H), 3.15 (m, 6H), 2.06 (m, 2H), 1.20 (t, J=7.0 Hz, 6H). Anal. Calcd. for $C_{29}H_{33}NO_4S.1.0$ HCl: C, 65.96; H, 6.49; N, 2.65. Found: C, 66.25; H, 6.64; N, 2.84.

EXAMPLE 18

[6-Hydroxy-3-[4-[2-(1-piperidinyl)ethoxy[-phenoxy]-2-(4-hydroxyphenyl)]benzo[b]thiophene

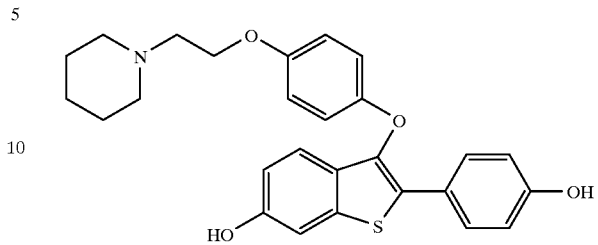

[6-methoxy-3-[4-[2-(1-piperidinyl)ethoxy]phenoxy]-2-(4-methoxyphenyl)]benzo[b]thiophene hydrochloride (10.00 g, 19.05 mmol) was dissolved in 500 mL of anhydrous methylene chloride and cooled to 8° C. To this solution was added boron tribromide (7.20 mL, 76.20 mmol). The resultant mixture was stirred at 8° C. for 2.5 hours. The reaction was quenched by pouring into a stirring solution of saturated sodium bicarbonate (1 L), cooled to 0° C. The methylene chloride layer was separated, and the remaining solids were dissolved in methanol/ethyl acetate. The aqueous layer was then extracted with 5% methanol/ethyl acetate (3×500 mL). All of the organic extracts (ethyl acetate and methylene chloride) were combined and dried (sodium sulfate). Concentration in vacuo provided a tan solid that was chromatographed (silicon dioxide, 1–7% methanol/chloroform) to provide 7.13 g (81 %) of [6-hydroxy-3-[4-[2-(1-piperidinyl) ethoxy]phenoxy]-2-(4-hydroxyphenyl)]benzo[b]-thiophene as a white solid. mp 93° C. $^1$H NMR (DMSO-$d_6$) d 9.73 (bs, 1H), 9.68 (bs, 1H), 7.45 (d, J=8.6 Hz, 2H), 7.21 (d, J =1.8 Hz, 1H), 7.04 (d, J=8.6 Hz, 1H), 6.84 (dd, J=8.6, 1.8 Hz, 1H (masked)), 6.81 (S, 4H), 6.75 (d, J=8.6 Hz, 2H), 3.92 (t, J=5.8 Hz, 2H), 2.56 (t, J=5.8 Hz, 2H), 2.36 (m. 4H), 1.43 (m, 4H), 1.32 (m, 2H). FD mass spec: 462. Anal. Calcd. for $C_{27}H_{27}NO_4S$: C, 70.20; H, 5.90; N, 3.03. Found: C, 69.96; H, 5.90; N, 3.14.

EXAMPLE 19

[6-Hydroxy-3-[4-[2-(1-piperidinyl)ethoxy]phenoxy]-2-(4-hydroxyphenyl)]benzo[b]thiophene is converted to its oxalate salt in 80% yield by the procedure described above. Data for [6-hydroxy-3-[4-[2-(1-piperidinyl)-ethoxy]phenoxyl-2-(4-hydroxyphenyl)]benzo[b]thiophene oxalate

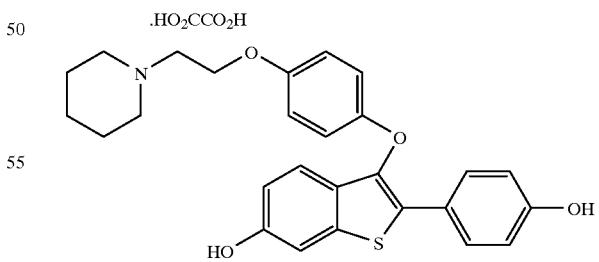

mp 246–249° C, (dec). $^1$H NMR (DMSO-$d_6$) d 7.45 (d, J=8.6 Hz, 2H), 7.22 (d, J=1.8 Hz, 1H), 7.05 (d, J=8.6 Hz, 1H), 6.87 (dd, J=8.6, 1.8 Hz, 1H (masked)), 6.84 (S, 4H), 6.75 (d, J=8.6 Hz, 2H), 4.08 (bt, 2H), 3.01 (bt, 2H), 2.79 (m, 4H), 1.56 (m, 4H), 1.40 (m, 2H). FD mass spec 462. Anal. Calcd. for $C_{27}H_{27}NO_4S.0.75$ $HO_2CCO_2H$: C, 64.63; H, 5.42; N, 2.64. Found: C, 64.61; H, 5.55; N, 2.62.

EXAMPLE 20

[6-Hydroxy-3-[4-[2-(1-piperidinyl)ethoxy]phenoxy]-2-(4-hydroxyphenyl)]benzo[b]thiophene was converted to its hydrochloride salt in 91% yield by treatment of the free base in ethyl acetate with ethyl ether-hydrochloric acid. Data for [6-hydroxy-3-[4-[2-(1-piperidinyl)ethoxy]-phenoxy]-2-(4-hydroxyphenyl)]benzo [b]thiophene hydrochloride

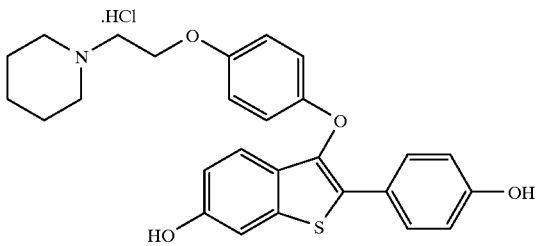

mp 158–165° C. $^1$H NMR (DMSO-$d_6$) d 9.79 (s, 1H), 9.74 (s, 1H), 7.40 (d, J=8.6 Hz, 2H), 7.23 (d, J=2.0 Hz, 1H), 7.04 (d, J=8.6 Hz, 1H), 6.86 (q, $J_{AB}$=9.3 Hz, 4H), 6.76 (dd, J=8.6, 2.0 Hz, 1), 6.74 (d, J=8.6 Hz, 2H), 4.26 (bt, 2H), 3.37 (m, 4H), 2.91 (m, 2H), 1.72 (m, 5H), 1.25 (m, 1H). FD mass spec 461. Anal. Calcd. for $C_{27}H_{27}NO_4S \cdot 1.0$ HCl: C, 65.11; H, 5.67; N, 2.81. Found: C, 64.84; H, 5.64; N, 2.91.

Prepared in an analogous manner were the following examples:

EXAMPLE 21

[6-Hydroxy-3-[4-[2-(1-pyrolidinyl)ethoxy]phenoxy]-2-(4-hydroxyphenyl)]benzo[b]thiophene

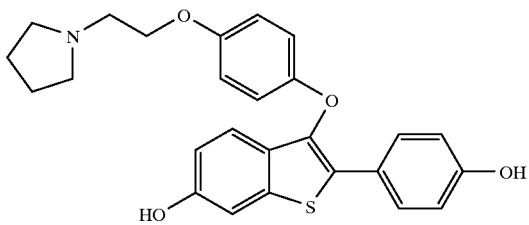

mp 99–113° C. $^1$H NMR (DMSO-$d_6$) d 9.75 (s, 1H), 9.71 (s, 1H), 7.50 (d, J=9.0 Hz, 2H), 7.25 (d, J=2.0 Hz, 1H), 7.09 (d, J=9.0 Hz, 1H), 6.85 (s, 1H), 6.80 (dd, J=9.0, 2.0 Hz, 1H), 6.79 (d, J=9.0 Hz, 2H), 3.93 (m, 2H), 2.73 (m, 2H), 2.53 (m, 4H), 0.96 (t, J=7.0 Hz, 4H). Anal. Calcd. for $C_{26}H_{25}NO_4S \cdot 0.5\ H_2O$: C, 68.40; H, 5.74; N, 3.07. Found: C, 68.52; H, 6.00; N, 3.34.

EXAMPLE 22

[6-Hydroxy-3-[4-[2-(1-hexamethyleneimino)ethoxy]phenoxy]-2-(4-hydroxyphenyl)]benzo[b]thiophene

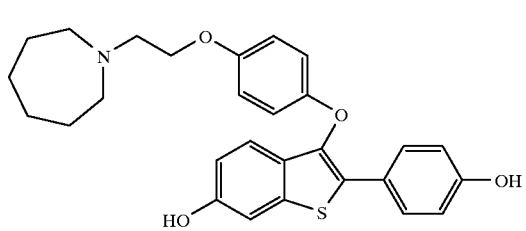

mp 125–130° C. $^1$H NMR (DMSO-$d_6$) d 9.75 (s, 1H), 9.71 (s, 1H), 7.50 (d, J=9.0 Hz, 2H), 7.26 (d, J=2.0 Hz, 1H), 7.09 (d, J=9.0 Hz, 1H), 6.85 (s, 3H), 6.80 (dd, J=9.0, 2.0 Hz, 1H), 6.79 (d, J=9.0 Hz), 3.94 (t, J=6.0 Hz, 2H), 2.80 (t, J=6.0 Hz, 2H), 2.66 (m, 4H), 1.53 (m, 8H). Anal. Calcd. for $C_{28}H_{29}NO_4S$: C, 70.71; H, 6.15; N, 2.94. Found: C, 70.67; H, 6.31; N, 2.93.

EXAMPLE 23

[6-Hydroxy-3-[4-[2-(1-N,N-diethylamino)ethoxy]phenoxy]-2-(4-hydroxyphenyl)]benzo[b]thiophene

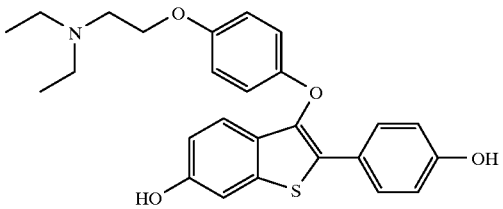

mp 137–141° C. $^1$H NMR (DMSO-$d_6$) d 9.75 (S, 1H), 9.71 (S, 1H), 7.49 (d, J=9.0 Hz, 1H), 7.25 (d, j =2.0 Hz, 1H), 7.09 (d, J=9.0 Hz, 1H), 6.85 (s, 4H), 6.80 (dd, J 9.0, 2.0 Hz, 1H), 6.79 (d, J=9.0 Hz, 2H), 3.95 (t, J=6.0 Hz, 2H), 2.74 (t, J=6.0 Hz, 2H), 2.51 (m, 4H), 1.66 (m, 6H). Anal. Calcd. for $C_{26}H_{27}NO_4S$: C, 69.46; H, 6.05; N, 3.12. Found: C, 69.76; H, 5.85; N, 3.40.

EXAMPLE 24

[6-Hydroxy-3-[4-[2-(morpholino)ethoxy]phenoxy]-2-(4-hydroxyphenyl)]benzo[b]thiophene hydrochloride

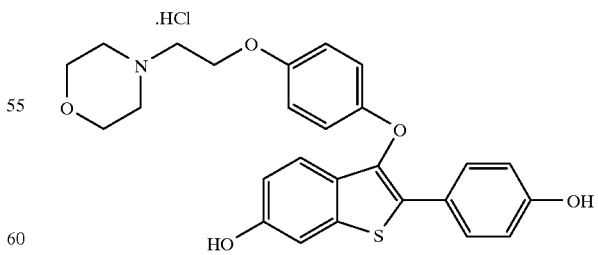

mp 157–162° C. $^1$H NMR (DMSO-$d_6$) d 10.60 (bs, 1H), 9.80 (s, 1H), 9.75 (s, 1H), 7.50 (d, J=9.0 Hz, 2H), 7.28 (d, J =2.0 Hz, 1H), 7.10 (d, J=9.0 Hz, 1H), 6.92 (q, $J_{AB}$=9.0 Hz, 4H), 6.81 (dd, J=9.0, 2.0 Hz, 1H), 6.80 (d, J=9.0 Hz, 2H), 4.30 (m, 2H), 3.95 (m, 2H), 3.75 (m, 2H), 3.51 (m, 4H), 3.18

(m, 2H). Anal. Calcd. for $C_{26}H_{25}NO_5S \cdot HCl$: C, 62.46; H, 5.24; N, 2.80. Found: C, 69.69; H, 5.43; N, 2.92.

EXAMPLE 25

[6-Hydroxy-3-[4-[3-(1-N,N-diethylamino) propoxy] phenoxy]-2-(4-hydroxyphenyl)]benzo [b]thiophene hydrochloride

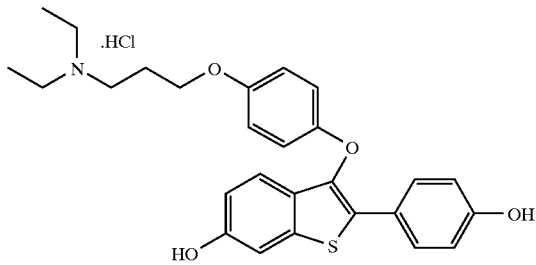

mp 185–191° C. $^1$H NMR (DMSO-$d_6$) d 9.94 (bs, 1H), 9.81 (s, 1H), 9.75 (s, 1H), 7.50 (d, J=9.0 Hz, 2H), 7.27 (dd, J=2.0 Hz, 1H), 7.10 (d, J=9.0 Hz, 1H), 6.87 (s, 4H), 6.80 (dd, J=9.0, 2.0 Hz, 1H), 6.79 (d, J=9.0 Hz, 2H), 3.99 (t, J=6.0 Hz, 2H), 3.14 (m, 6H), 2.08 (m, 2H), 1.20 (t, J=6.0 Hz, 6H). Anal. Calcd. for $C_{27}H_{29}NO_4S \cdot 1.30HCl$: C, 63.46; H, 5.98; N, 2.74. Found: C, 63.23; H, 6.03; N, 3.14.

EXAMPLE 26

[6-Hydroxy-3-[4-[2-(1-N,N-diisopropylamino)-ethoxy]phenoxy]-2-(4-hydroxyphenyl)]benzo[b]thiophene hydrochloride

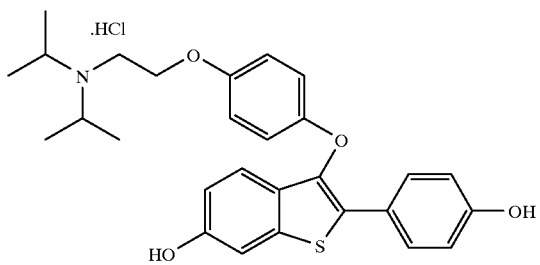

mp 128–131° C. $^1$H NMR (DMSO-$d_6$) d 9.81 (bs, 1H), 9.76 (s, 1H), 9.02 (s, 1H), 7.49 (d, J=9.0 Hz, 2H), 7.28 (m, 1H), 7.09 (d, J=9.0 Hz, 1H), 6.90 (s, 4H), 6.79 (m, 3H), 4.19 (m, 2H), 3.68 (m, 2H), 3.50 (m, 2H), 1.31 (m, 12H). Anal. Calcd. for $C_{28}H_{31}NO_4S \cdot 1.33HCl$: C, 63.92; H, 6.19; N, 2.66. Found: C, 63.82; H, 6.53; N, 2.61.

EXAMPLE 27

[6-Hydroxy-3-[4-[3-(piperidino)propoxy]phenoxy]-2-(4-hydroxyphenyl)]benzo[b]thiophene hydrochloride

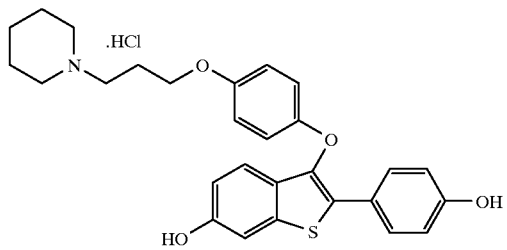

mp 258–262° C. $^1$H NMR (DMSO-$d_6$) d 9.85 (bs, 1H), 9.81 (s, 1H), 9.75 (s, 1H), 7.50 (d, J=9.0 Hz, 2H), 7.27 (d, J=2.0 Hz, 1H), 7.10 (d, J=9.0 Hz, 1H), 6.87 (s, 4H), 6.80 (dd, J=9.0, 2.0 Hz, 1H), 6.79 (d, J=9.0 Hz, 2H), 3.97 (t, J=6.0 Hz, 2H), 3.44 (m, 2H), 3.15 (m, 2H), 2.88 (m, 2H), 2.11 (m, 2H), 1.73 (m, 5H), 1.39 (m, 1H). Anal. Calcd. for $C_{28}H_{29}NO_4S \cdot 0.75HCl$: C, 66.87; H, 5.96; N, 2.78. Found: C, 67.04; H, 5.90; N, 2.68.

Alternatively, as shown in Scheme III, supra, Example 19 was prepared using the methoxymethyl (MOM) protecting groups in place of methoxy. The methods are directly analogous to those just described, with the exception that the MOM groups are removed in the final step by acid hydrolysis.

Preparation 10

[6-Methoxy-2-(4-methoxmethyloxyphenyl)-3-(4-benzyloxy) phenoxy]benzo[b]thiophene

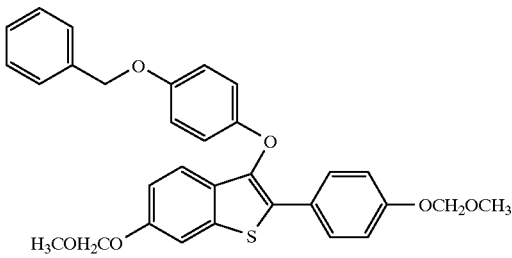

mp 94–96° C. $^1$H NMR (DMSO-$d_6$) d 7.65 (d, J=2.0 Hz, 1H), 7.64 (d, J=8.6 Hz, 2H), 7.43–7.32 (m, 5H), 7.23 (d, J=8.8 Hz, 1H), 7.08 (d, J=8.6 Hz, 2H), 7.04 (dd, J=8.8, 2.0 Hz, 1H), 6.92 (q, $J_{AB}$=9.2 Hz, 4H), 5.26 (S, 2H), 5.21 (S, 2H), 5.01 (s, 3H), 3.40 (S, 3H), 3.37 (S, 3H). FD mass spec 528.

Preparation 11

[6-Methoxy-2-(4-methoxmethyloxyphenyl)-3-(4-hydroxy)phenoxy]benzo[b]thiophene

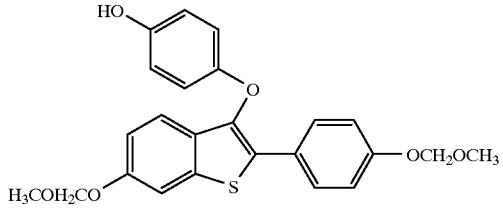

mp 90–91° C. $^1$H NMR (DMSO-$d_6$) d 9.15 (s, 1H), 7.65 (d, J =8.1 Hz, 2H), 7.63 (d, J=2.0 Hz, 1H), 7.22 (d, J=8.8 Hz, 1H), 7.05 (dd, J=8.8, 2.0 Hz, 1H), 6.72 (q, $J_{AB}$=9.1 Hz, 4H), 5.26 (s, 2H), 5.21 (s, 2H), 3.40 (s, 3H), 3.37 (s, 3H). FD mass spec 438. Anal. Calcd. for $C_{24}H_{22}O_6S$: C, 65.74; H, 5.06. Found: C, 65.50; H, 4.99.

EXAMPLE 28

[6-Methoxy-2-(4-methoxyphenyl)-3-bromo]benzo[b]thiophene-(S-oxide)

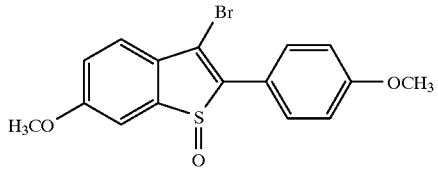

To a solution of [6-methoxy-2-(4-methoxyphenyl)-3-bromo]benzo [b]thiophene (10.0 g, 28.6 mmol) in 50 mL of anhydrous methylene chloride was added 50 mL of triflouroacetic acid. After stirring for 5 minutes, hydrogen peroxide (4.0 mL, 28.6 mmol, 30% aqueous solution) was added. The resulting mixture was stirred at ambient temperature for 2 hours. Solid sodium bisulfite (1.25 g) was added to the dark solution followed by 15 mL of water. The mixture was stirred vigorously for 15 minutes then concentrated in vacuo. The residue was partitioned between chloroform saturated sodium bicarbonate solution (200 mL ea.). The layers were separated and the organic layer was extracted with saturated sodium bicarbonate solution. The organic layer was then dried (sodium sulfate) and concentrated in vacuo to a solid that was triturated from ethyl ether/ethyl acetate. Filtration provided 8.20 g (80%) of [6-methoxy-2-(4-methoxyphenyl)-3-bromo]benzo[b]thiophene-(S-oxide) as a yellow solid that can be recrystallized from ethyl acetate. m.p. 170–173° C. $^1$H NMR (DMSO-$d_6$) d 7.24 (d, J=2.2 Hz, 1H), 7.68 (d, J=8.8 Hz, 2H), 7.54 (d, J=8.5 Hz, 1H), 7.26 (dd, J=8.5, 2.2 Hz, 1H), 7.10 (d, J=8.8 H, 2H), 3.86 (s, 3H), 3.80 (s, 3H). Anal. Calcd. for $C_{16}H_{13}O_3SBr$: C, 52.62; H, 3.59. Found: C, 52.40; H, 3.55.

EXAMPLE 29

Prepared in an analogous manner was [2-(4-methoxyphenyl)-3-bromolbenzo[b]thiophene-(S-oxide).

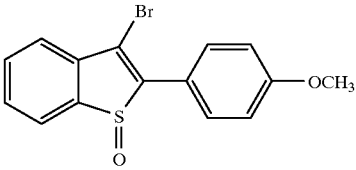

mp 120–125° C. $^1$H NMR (DMSO-$d_6$) d 8.06 (d, J=7.6 Hz, 1H), 7.78–7.59 (m, 5H), 7.13 (d, J=8.7 Hz, 2H), 3.81 (s, 3H). FD mass spec: 335. Anal. Calcd. for $C_{15}H_{11}O_2SBr$: C, 53.75; H, 3.31. Found: C, 53.71; H, 3.46.

Preparation 12

Preparation of 4-(2-(1-piperidinyl)ethoxy)-phenol.

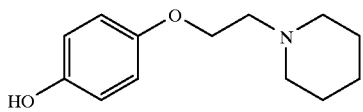

To a solution of 4-benzyloxyphenol (50.50 g, 0.25 mol) in 350 mL of anhydrous DMF was added 2-chloroethylpiperidine (46.30 g, 0.25 mol). After stirring for 10 minutes, potassium carbonate (52.0 g, 0.375 mol) and cesium carbonate (85.0 g, 0.25 mol) were added. The resulting heterogeneous mixture was stirred vigorously at ambient temperature for 48 hours. The reaction was then poured into water (500 mL) and extracted with methylene chloride. The organic was then extracted with 1N sodium hydroxide several times and finally washed with brine. The organic layer was then dried (sodium sulfate) and concentrated in vacuo to an oil. Chromatography (SiO$_2$, 1:1 hexanes/ethyl acetate) provided 60.0 g (77%) of 4-[2-(1-piperidinyl)ethoxy]phenoxybenzyl ether as a colorless oil. $^1$H NMR (DMSO-$d_6$) d 7.40–7.27 (m, 5H), 6.84 (q, $J_{AB}$= 11.5 Hz, 4H), 4.98 (s, 2H), 3.93 (t, J=6.0 Hz, 2H), 2.56 (t, J=6.0 Hz, 2H), 2.35–2.37 (m, 4H), 1.48–1.32 (m, 6H). FD mass spec: 311. Anal. Calcd. for $C_{20}H_{25}NO_2$: C, 77.14; H, 8.09; N, 4.50. Found: C, 77.34; H, 8.18; N, 4.64.

4-[2-(1-Piperidinyl)ethoxy]phenoxybenzyl ether (21.40 g, 68,81 mmol) was dissolved in 200 mL of 1:1 EtOH/EtOAc containing 1% con. HCl. The solution was transferred to a Parr bottle, and 5% palladium-on-carbon (3.4 g) was added. The mixture was hydrogenated at 40 psi for 2 hours. The mixture was then passed through a plug of Celite to remove catalyst. The filtrate was concentrated in vacuo to a solid that was slurried in ethyl ether and filtered to provide 12.10 g (83%) of 4-(2-(1-piperidinyl) ethoxy)-phenol. mp 148–150° C. $^1$H NMR (DMSO-$d_6$) d 8.40 (s, 1H), 6.70 (q, $J_{AB}$=11.5 Hz, 4H), 3.93 (t, J=6.0 Hz, 2H), 2.59 (t, J=6.0 Hz, 2H), 2.42–2.38 (m, 4H), 1.52–1.32 (m, 6H). FD mass spec: 221. Anal. Calcd. for $C_{13}H_{19}NO_2$: C, 70.56; H, 8.09; N, 4.50. Found: C, 70.75; H, 8.59; N, 6.54.

EXAMPLE 30

[6-Methoxy-3-[4-[2-(1-piperidinyl)ethoxy]phenoxy]-2-(4-methoxyphenyl)]benzo[b]thiophene-(S-oxide)

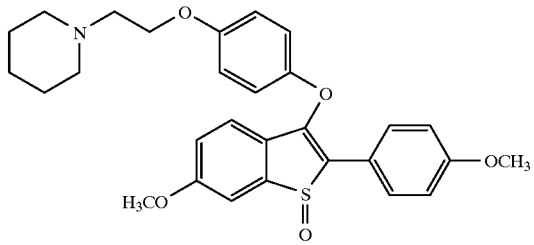

To a solution of 4-(2-(1-piperidinyl)ethoxy)-phenol (0.32 g, 1.43 mmol) in 5 mL of anhydrous DMF at ambient temperature was added sodium hydride (0.57 g, 1.43 mmol, 60% dispersion in mineral oil). After stirring for 15 minutes, [6-methoxy-2-(4-methoxyphenyl)-3-bromo]benzo[b]thiophene-(S-oxide) (0.50 g, 1.37 mmol) was added in small portions. After stirring for 1 hour, the reaction was judged complete by TLC analysis. The solvent was removed in vacuo, and the residue was distributed between water and 10% ethanol/ethyl acetate. The organic was washed several times with water and then dried (sodium sulfate). Concentration in vacuo gave an oil that was triturated from ethyl acetate/hexanes to provide 0.62 g (89%) of [6-methoxy-3-[4-[2-(1-piperidinyl)ethoxy]phenoxy]-2-(4-methoxyphenyl)]benzo [b]thiophene-(S-oxide) as a light yellow solid. mp 97–100° C. $^1$H NMR (DMSO-$d_6$) d 7.68 (d, J=2.1 Hz, 1H), 7.62 (d, J=8.8 Hz, 2H), 7.06–6.92 (m, 6H), 6.85 (d, J=8.8 Hz, 2H), 3.94 (t, J=6.0 Hz, 2H), 3.81 (s, 3H), 3.72 (s, 3H), 2.56 (t, J=6.0 Hz, 2H), 2.39–2.32 (m, 4H), 1.47–1.32 (m, 6H). Anal. Calcd. for $C_{29}H_{31}NO_5S$: C, 68.89; H, 6.18; N, 2.77. Found: C, 68.95; H, 6.04; N, 2.57.

EXAMPLE 31

Prepared in an analogous manner was [3-[4-[2-(1-piperidinyl)ethoxy]phenoxy]-2-(4-methoxyphenyl)]benzo[b]thiophene-(S-oxide)

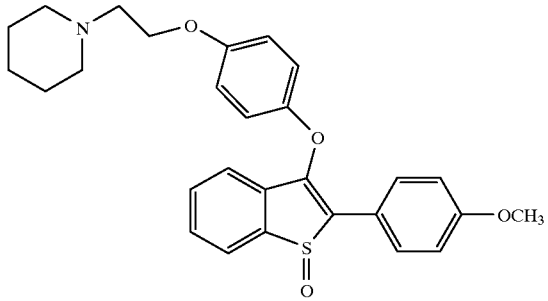

Oil. $^1$H NMR (DMSO-$d_6$) d 8.03 (m, 1H), 7.65 (d, J=8.7 Hz, 2H), 7.53–7.50 (m, 2H), 7.09–6.82 (m, 7H), 3.94 (bt, J=5.9 Hz, 2H), 3.74 (s, 3H), 2.56 (bt, J=5.9 Hz, 2H), 2.36–2.33 (m, 4H), 1.45–1.31 (m, 6H). FD mass spec: 475. Anal. Calcd. for $C_{28}H_{29}NO_4S$: C, 70.71; H, 6.15; N, 2.94. Found: C, 70.44; H, 6.43; N, 3.20.

EXAMPLE 32

[6-Methoxy-3-[4-[2-(1-piperidinyl)ethoxy]phenoxy]-2-(4-methoxyphenyl)]benzo[b]thiophene hydrochloride

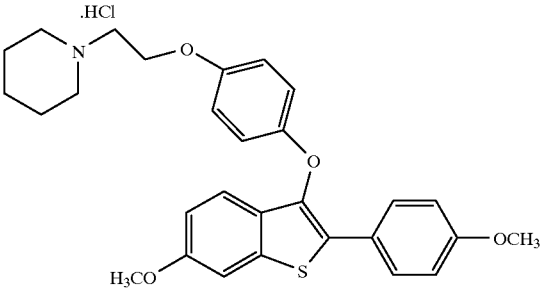

To a solution of [6-methoxy-3-[4-[2-(1-piperidinyl)ethoxy]phenoxy]-2-(4-methoxyphenyl)]benzo[b]thiophene-(S-oxide) (Example 30) (3.00 g, 5.94 mmol) in 200 mL of anhydrous THF under nitrogen gas at 0° C. was added lithium aluminum hydride (0.34 g, 8.91 mmol) in small portions. After stirring for 30 minutes, the reaction was quenched by the careful addition of 5.0 mL of 2.0N sodium hydroxide. The mixture was stirred vigorously for 30 minutes, and additional 2.0N sodium hydroxide was added to dissolve salts. The mixture was then distributed between water and 10% sodium hydroxide. The layers were separated and the aqueous extracted several times with 10% ethanol/ethyl acetate. The organic layer was dried (sodium sulfate) and concentrated in vacuo to an oil. The crude product was dissolved in 50 mL of 1:1 ethyl acetate/ethyl ether and treated with excess ethyl ether hydrochloride. The resulting precipitate was collected and dried to provide 2.98 g (96%) of [6-methoxy-3-[4-[2-(1-piperidinyl) ethoxy]phenoxy]-2-(4-methoxyphenyl)]benzo[b]thiophene hydrochloride as a white solid.

Example 6 was also prepared from Example 31 by the same procedure.

Preparation 13

6-Methoxybenzo[b]thiophene-2-boronic acid

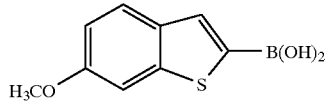

To a solution of 6-methoxybenzo[b]thiophene (18.13 g, 0.111 mol) in 150 mL of anhydrous tetrahydrofuran (THF) at −60° C. was added n-butyllithium (76.2 mL, 0.122 mol, 1.6M solution in hexanes), dropwise via syringe. After stirring for 30 minutes, triisopropyl borate (28.2 mL, 0.122 mol) was introduced via syringe. The resulting mixture was allowed to gradually warm to 0° C. and then distributed between 1N hydrochloric acid and ethyl acetate (300 mL each). The layers were separated, and the organic layer was dried over sodium sulfate. Concentration in vacuo produced a white solid that was triturated from ethyl ether hexanes. Filtration provided 16.4 g (71%) of 6-methoxybenzo[b]thiophene-2-boronic acid as a white solid. mp 200° C. (dec). $^1$H NMR (DMSO-$d_6$) d 7.83 (s, 1H), 7.78 (d, J=8.6 Hz, 1H), 7.51 (d, J=2.0 Hz, 1H), 6.97 (dd, J=8.6, 2.0 Hz, 1H), 3.82 (s, 3H). FD mass spec: 208.

Preparation 14

[6-Methoxy-2-(4-methanesulfonyloxyphenyl)]benzo[b]thiophene

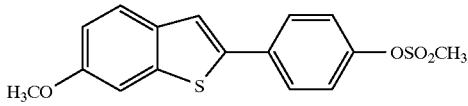

To a solution of 6-methoxybenzo[b]thiophene-2-boronic acid (3.00 g, 14.4 mmol) in 100 mL of toluene was added 4-(methanesulfonyloxy)phenylbromide (3.98 g, 15.8 mmol) followed by 16 mL of 2.0N sodium carbonate solution. After stirring for 10 minutes, tetrakistriphenylphosphinepalladium (0.60 g, 0.52 mmol) was added, and the resulting mixture was heated to reflux for 5 hours. The reaction mixture was then allowed to cool to ambient temperature whereupon the product precipitated from the organic phase. The aqueous phase was removed and the organic layer was concentrated in vacuo to a solid. Trituration from ethyl ether yielded a solid that was filtered and dried in vacuo to provide 3.70 g (77%) of [6-methoxy-2-(4-methanesulfonyloxy-phenyl)]benzo[b]thiophene as a tan solid. mp 197–201° C. $^1$H NMR (DMSO-d$_6$) d 7.82–7.77 (m, 3H), 7.71 (d, J=8.8 Hz, 1H), 7.54 (d, J=2.3 Hz, 1H), 7.40 (d, J=8.7 Hz, 2H), 6.98 (dd, J=8.7, 1.5 Hz, 1H), 3.80 (s, 3H), 3.39 (s, 3H) FD mass spec 334. Anal. Calcd. for C$_{16}$H$_{14}$O$_4$S$_2$: C, 57.46; H, 4.21. Found: C, 57.76; H, 4.21.

Preparation 15

Prepared in an analogous manner to Preparation 14 was [6-methoxy-2-(4-benzyloxyphenyl)]benzo[b]thiophene

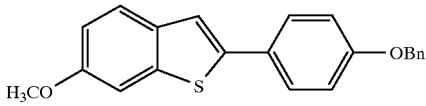

Yield=73%. mp 217–221° C. $^1$H NMR (DMSO-d$_6$) d 7.63–7.60 (m, 3H), 7.59–7.26 (m, 7H), 7.02 (d, J=8.7 Hz, 2H), 6.96 (dd, J=8.8, 2.2 Hz, 1H), 5.11 (s, 2H), 3.88 (s, 3H). FD mass spec 346. Anal. Calcd. for C$_{22}$H$_{18}$O$_2$S: C, 76.27; H, 5.24. Found: C, 76.00; H, 5.25.

Preparation 16

[6-Hydroxy-2-(4-methanesulfonyloxyphenyl)]benzo[b]thiophene

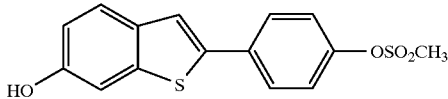

To a solution of [6-methoxy-2-(4-methanesulfonyloxy-phenyl)]benzo[b]thiophene (9.50 g, 28.40 mmol) in anhydrous methylene chloride (200 mL) at room under nitrogen gas was added boron tribromide (14.20 g, 5.36 mL, 56.8 mmol). The resulting mixture was stirred at ambient temperature for 3 hours. The reaction was quenched by slowly pouring into excess ice water. After vigorously stirring for 30 minutes, the white precipitate was collected by filtration, washed several times with water, and then dried in vacuo to provide 8.92 g (98%) of [6-hydroxy-2-(4-methanesulfonyloxyphenyl)]benzo[b]thiophene as a white solid. mp 239–243° C. $^1$H NMR (DMSO-d$_6$) d 9.70 (S, 1H), 7.76 (d, J=8.7 Hz, 2H), 7.72 (s, 1H), 7.62 (d, J=8.7 Hz, 1H), 7.38 (d, J=8.7 Hz, 2H), 7.24 (d, J=1.7 Hz, 1H), 6.86 (dd, J=8.7, 1.7 Hz, 1H), 3.38 (s, 3H). FD mass spec 320. Anal. Calcd. for C$_{15}$H$_{12}$O$_4$S$_2$: C, 56.23; H, 3.77. Found: C, 56.49; H, 3.68.

Preparation 17

[6-Benzyloxy-2-(4-methanesulfonyloxyphenyl)]benzo[b]thiophene

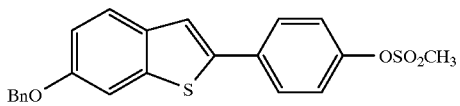

To a solution of [6-hydroxy-2-(4-methanesulfonyloxy-phenyl)]benzo[b]thiophene (3.20 g, 10.0 mmol) in 75 mL of anhydrous DMF was added Cs$_2$CO$_3$ (5.75 g, 17.7 mmol) followed by benzylchloride (1.72 mL, 11.0 mmol). The resulting mixture was stirred vigorously for 24 hours. The solvent was removed in vacuo, and the solid residue was suspended in 200 mL of water. The white precipitate was collected by filtration and washed several times with water. Upon drying in vacuo, the crude product was suspended in 1:1 hexanes:ethyl ether. The solid was collected to provide 3.72 g (91%) of [6-benzyloxy-2-(4-methanesulfonyloxy-phenyl)]benzo[b]thiophene as a white solid. mp 198–202° C. $^1$H NMR (DMSO-d$_6$) d 7.81–7.78 (m, 3H), 7.72 (d, J=8.7 Hz, 1H), 7.64 (d, J=2.2 Hz, 1H), 7.47–7.30 (m, 7H), 5.15 (s, 2H), 3.39 (s, 3H). FD mass spec 410.

Preparation 18

[6-Benzyloxy-2-(4-hydroxyphenyl)]benzo[b]thiophene

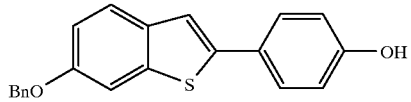

To a solution of [6-benzyloxy-2-(4-methanesulfonyloxy-phenyl)]benzo[b]thiophene (12.50 g, 30.50 mmol) in 300 mL of anhydrous THF under nitrogen gas at ambient temperature was added lithium aluminum hydride (2.32 g, 61.0 mmol) in small portions. The mixture was then stirred at ambient temperature for 3 hours and then quenched by carefully pouring the mixture into an excess of cold 1.0N hydrochloric acid. The aqueous phase was extracted with ethyl acetate. The organic was then washed several times with water and then dried (sodium sulfate) and concentrated in vacuo to a solid. Chromatography (silicon dioxide, chloroform) provided 8.75 g (87%) of [6-benzyloxy-2-(4-hydroxyphenyl)]benzo[b] thiophene as a white solid. mp 212–216° C. $^1$H NMR (DMSO-d$_6$) d 9.70 (s, 1H), 7.63 (d, J=8.7 Hz, 1H), 7.56 (d, J=2.2 Hz, 1H), 7.51–7.30 (m, 8H), 7.00 (dd, J=8.7, 2.2 Hz, 1H), 6.80 (d, J =8.6 Hz, 2H), 5.13 (s, 2H). FD mass spec 331. Anal. Calcd. for C$_{21}$H$_{16}$O$_2$S: C, 75.88; H, 4.85. Found: C, 75.64; H, 4.85.

EXAMPLE 19

[6-Benzyloxy-2-(4-methoxyphenyl)]benzo[b]thiophene

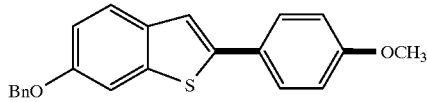

To a solution of [6-benzyloxy-2-(4-hydroxyphenyl)] benzo[b]thiophene (8.50 g, 26.40 mmol) in 200 mL of anhydrous DMF under nitrogen gas at ambient temperature was added sodium hydride (1.66 g, 41.5 mmol) in small portions. once gas evolution had ceased, iodomethane (3.25 mL, 52.18 mmol) was added dropwise. The reaction was stirred for 3 hours at ambient temperature. The solvent was then removed in vacuo, and the residue distributed between water/ethyl acetate. The layers were separated, and the organic phase was washed several times with water. The organic layer was then dried (sodium sulfate) and concentrated in vacuo to provide 9.00 g (98%) of [6-benzyloxy-2-(4-methoxyphenyl)]benzo[b]thiophene as a white solid. mp 180–185° C. $^1$H NMR (DMSO-d$_6$) d 7.67–7.58 (m, 5H), 7.46–7.29 (m, 5H), 7.02 (dd, J =8.8, 2.2 Hz, 1H), 6.98 (d, J=8.7 Hz, 2H), 5.13 (s, 2H), 3.76 (s, 3H). FD mass spec 346. Anal. Calcd. for $C_{22}H_{18}O_2S$: C, 76.27; H, 5.24. Found: C, 76.54; H, 5.43.

Preparation 20

[6-Benzyloxy-2-(4-methoxyphenyl)-3-bromo]benzo-[b] thiophene

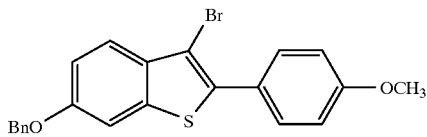

[6-Benzyloxy-2-(4-methoxyphenyl)]benzo[b]thiophene (10.0 g, 28.9 mmol) was placed in 200 mL of chloroform along with 10.0 g of solid sodium bicarbonate at ambient temperature. To this suspension was added bromine (1.50 mL, 29.1 mmol) dropwise over 30 minutes as a solution in 100 mL of chloroform. Upon completion of the addition, water (200 mL) was added and the layers were separated. The organic phase was dried (sodium sulfate) and concentrated in vacuo to a white solid. Crystallization from methylene chloride/methanol provided 10.50 g (85%) of [6-benzyloxy-2-(4-methoxyphenyl)-3-bromo]benzo-[b] thiophene as a white solid. mp 146–150° C. $^1$H NMR (DMSO-d$_6$) d 7.70 (d, J=2.2 Hz, 1H), 7.65–7.60 (m, 3H), 7.47–7.30 (m, 5H), 7.19 (dd, J=8.8, 2.2 Hz, 1H), 7.06 (d, J=8.7 Hz, 2H), 5.17 (s, 2H), 3.78 (s, 3H). FD mass spec 346. Anal. Calcd. for $C_{22}H_{17}O_2SBr$: C, 62.13; H, 4.03. Found: C, 61.87; H, 4.00.

Preparation 21

Prepared in an analogous manner was [6-methoxy-2-(4-benzyloxyphenyl)-3-bromo]benzo-[b]thiophene

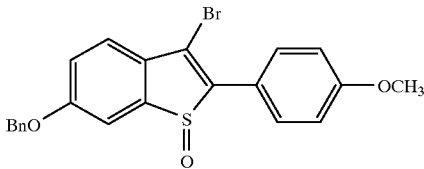

Yield=91%. mp 125–127° C. $^1$H NMR (DMSO-d6) d 7.64–7.61 (m, 4H), 7.46–7.31 (m, 5H), 7.15–7.09 (m, 3H), 5.15 (s, 2H), 3.82 (S, 3H). FD mass spec 346. Anal. Calcd. for $C_{22}H_{17}O_2SBr$: C, 62.13; H, 4.03. Found: C, 62.33; H, 3.93.

Prepared in a manner analgous to Example 28 are Examples 33–34.

EXAMPLE 33

[6-Benzyloxy-2-(4-methoxyphenyl)-3-bromo]benzo [b]thiophene-(S-oxide)

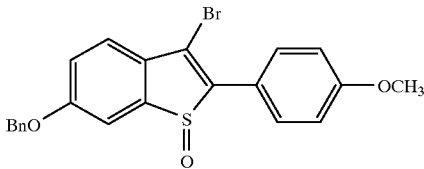

Isolated as a yellow solid by crystallization from ethyl acetate. mp 202–205° C. $^1$H NMR (DMSO-d$_6$) d 7.80 (d, J=2.2 Hz, 1H), 7.68 (d, J=8.7 Hz, 2H), 7.55(d, J=8.4 Hz, 1H) 7.47–7.32 (m, 6H), 7.10 (d, J=8.7 Hz, 2H), 5.23 (S, 2H), 3.80 (S, 3H). FD mass spec 441. Anal. Calcd. for $C_{22}H_{17}O_3SBr$: C, 59.87; H, 3.88. Found: C, 59.59; H, 3.78.

EAXMPLE 34

[6-Methoxy-2-(4-benzyloxyphenyl)-3-bromo]benzo [b]thiophene-(S-oxide)

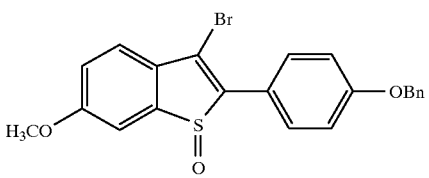

Isolated as a yellow solid by chromatography (SiO$_2$, CHCl$_3$). mp 119–123° C. $^1$H NMR (DMSO-d$_6$) d 7.73 (d, J=2.2 Hz, 1H), 7.68 (d, J=8.8 Hz, 2H), 7.55 (d, J=8.5 Hz, 1H) 7.46–7.31 (m, 5), 7.26 (dd, J=8.5, 2.2 Hz, 1H), 7.18 (d, J =8.8 Hz, 2H), 5.16 (s, 2H), 3.86 (s, 3H). FD mass spec 441. Anal. Calcd. for $C_{22}H_{17}O_3SBr$: C, 59.87; H, 3.88. Found: C, 60.13; H, 4.10.

Prepared in a manner analagous to Example 30 are Examples 35–36.

EXAMPLE 35

[6-Benzyloxy-3-[4-[2-(1-piperidinyl)ethoxy]phenoxy]-2-(4-methoxyphenyl)]benzo[b]thiophene-(S-oxide)

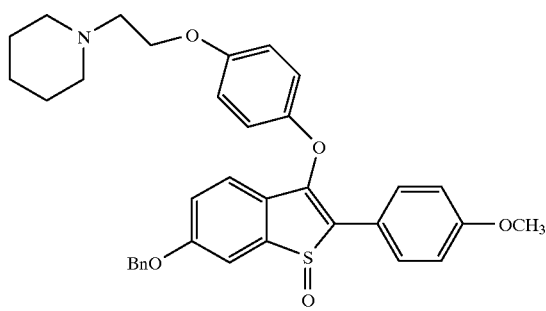

Yellow oil. $^1$H NMR (DMSO-d$_6$) d 7.76 (d, J=2.2 Hz, 1H), 7.62 (d, J=8.8 Hz, 2H), 7.44–7.30 (m, 5H), 7.12 (dd, J=8.6, 2.2 Hz, 1H), 7.03–6.93 (m, 5H), 6.85 (d, J=8.8 Hz, 2H), 5.18 (s, 2H), 3 .94 (bt, J=5.8 Hz, 2H), 3.73 (s, 3H), 2.56 (bt, J=5.8 Hz, 2H), 2.37–2.34 (m, 4H), 1.45–1.32 (m, 6H). FD mass spec 592. Anal. Calcd. for C$_{35}$H$_{35}$NO$_5$S: C, 72.26; H, 6.06; N, 2.41. Found: C, 72.19; H, 5.99; N, 2.11.

EXAMPLE 36

[6-Methoxy-3-[4-[2-(1-piperidinyl)ethoxy]phenoxy]-2-(4-benzyloxyphenyl)]benzo[b]thiophene-(S-oxide)

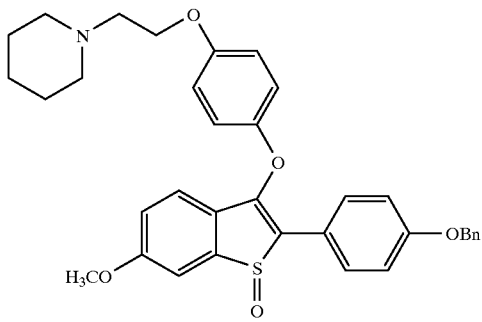

Yellow solid. mp 89–93° C. $^1$H NMR (DMSO-d$_6$) d 7.68 (d, J =2.2 Hz, 1H), 7.62 (d, J=8.8 Hz, 2H), 7.42–7.28 (m, 5H), 7.08–6.92 (m, 6H), 6.86 (d, J=8.8 Hz, 2H), 5.09 (s, 2H), 3.94 (bt, J=5.8 Hz, 2H), 3.81 (s, 3H), 2.56 (bt, J=5.8 Hz, 2H), 2.37–2.34 (m, 4H), 1.45–1.31 (m, 6H). FD mass spec 592. Anal. Calcd. for C$_{35}$H$_{35}$NO$_5$S.0.25 EtOAc: C, 71.62; H, 6.18; N, 2.32. Found: C, 71.32; H, 5.96; N, 2.71.

Prepared in a manner analagous to Example 11 are Exampes 37–38.

EXAMPLE 37

[6-Benzyloxy-3-[4-[2-(1-piperidinyl)ethoxy]phenoxy]-2-(4-methoxyphenyl)]benzo[b]thiophene

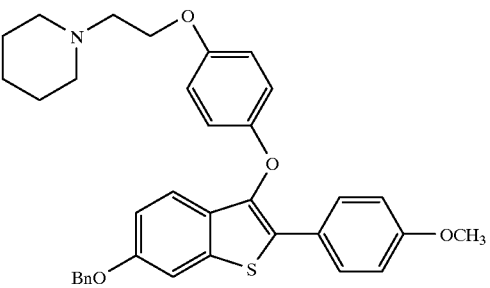

Isolated in 95% overall yield starting from [6-benzyloxy-2-(4-methoxyphenyl)-3-bromo]benzo[b]thiophene-(S-oxide). Purified by chromatography (SiO$_2$, 1–5% methanol/chloroform) to provide an off-white solid. mp 105–108° C. $^1$H NMR (DMSO-d$_6$) d 7.62 (d, J=2.2 Hz, 1H), 7.59 (d, J=8.8 Hz, 2H), 7.45–7.30 (m, 5H), 7.15 (dd, J=8.6 Hz, 1H), 7.00–6.94 (m, 3H), 6.82 (s, 4H), 5.13 (s, 2H), 3.92 (bt, J=5.8 Hz, 2H), 3.72 (s, 3H), 2.55 (bt, J=5.8 Hz, 2H), 2.37–2.34 (m, 4H), 1.44–1.31 (m, 4H). FD mass spec 565. Anal. Calcd. for C$_{35}$H$_{35}$NO$_4$S: C, 74.31; H, 6.24; N, 2.48. Found: C, 74.35; H, 6.07; N, 2.76.

EXAMPLE 38

[6-Methoxy-3-[4-[2-(1-piperidinyl)ethoxy]phenoxy]-2-(4-benzyloxyphenyl)]benzo[b]thiophene

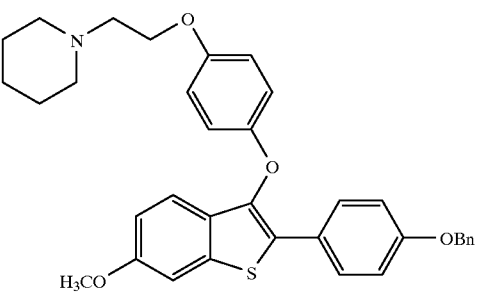

Yield=91%. mp 106–110° C. $^1$H NMR (DMSO-d$_6$) d 7.59 (d, J=8.8 Hz, 2H), 7.54 (d, J=2.2 Hz, 1H), 7.42–7.28 (m, 5H), 7.13 (d, J=8.8 Hz, 1H), 7.03 (d, J=8.8 Hz, 2H), 6.82 (s, 4H), 5.08 (s, 2H), 3.92 (bt, J=5.8 Hz, 2H), 3.78 (s, 3H), 2.55 (bt, J=5.8 Hz, 2H), 2.37–2.33 (m, 4H), 1.44–1.31 (m, 4H). FD mass spec 565. Anal. Calcd. for C$_{35}$H$_{35}$NO$_4$S: C, 74.31; H, 6.24; N, 2.48. Found: C, 74.26; H, 6.17; N, 2.73.

EXAMPLE 39

[6-Hydroxy-3-[4-[2-(1-piperidinyl)ethoxy]phenoxy]-2-(4-methoxyphenyl)]benzo[b]thiophene

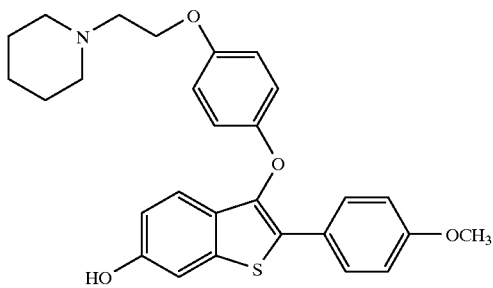

To a solution of [6-benzyloxy-3-[4-[2-(1-piperidinyl) ethoxy]phenoxy]-2-(4-methoxyphenyl)]benzo[b]thiophene (8.50 g, 15.0 mmol) in 300 mL of 5:1 ethanol/ethyl acetate was added palladium black (1.50 g), ammonium formate (3.50 g, 55.6 mmol), and 30 mL of water. The resulting mixture was heated to reflux and monitored by TLC. After approximately 3 hours, the reaction was judged complete and the solution was cooled to ambient temperature. The reaction was filtered through a pad of Celite to remove catalyst, and the filtrate was concentrated in vacuo to a solid. The concentrate was distributed between saturated sodium bicarbonate solution and 5% ethanol/ethyl acetate. The layers were separated, and the organic phase was dried (sodium sulfate) and concentrated in vacuo. The crude product was chromatographed (silicon dioxide, 1–5% methanol/chloroform) to provide 6.50 g (91%) of [6-hydroxy-3-[4-[2-(1-piperidinyl) ethoxy]phenoxy]-2-(4-methoxyphenyl)]benzo[b]thiophene as foam that converted to solid upon trituration with hexanes. mp 174–176° C. $^1$H NMR (DMSO-$d_6$) d 9.77 (s, 1H), 7.56 (d, J=8.8 Hz, 2H), 7.23 (d, J=2.0 Hz, 1H), 7.07 (d, J=8.6 Hz, 1H), 6.93 (d, J=8.8 Hz, 2H), 6.81 (S, 4H), 6.76 (dd, J=8.6, 2.0 Hz, 1H), 3.91 (bt, J=5.9 Hz, 2H), 3.71 (s, 3H), 2.55 (bt, J=5.9 Hz, 2H), 2.38–2.33 (m, 4H), 1.46–1.28 (m, 6H). FD mass spec 475. Anal. Calcd. for $C_{28}H_{29}NO_4S$: C, 70.71; H, 6.15; N, 2.94. Found: C, 70.46; H, 5.93; N, 2.71.

EXAMPLE 40

Prepared in an analogous manner to Example 39 was [6-methoxy-3-[4-[2-(1-piperidinyl)ethoxy]phenoxy]-2-(4-hydroxyphenyl)]benzo[b]thiophene

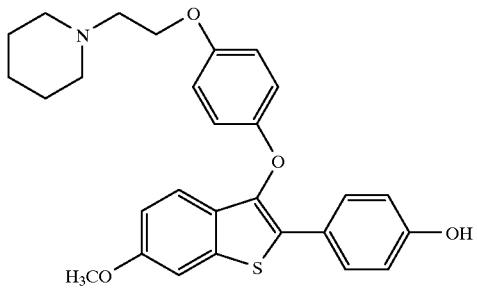

Yield=88%. mp 147–150° C. $^1$H NMR (DMSO-$d_6$) d 9.72 (s, 1H), 7.51 (d, J=2.0 Hz, 1H), 7.48 (d, J=8.6 Hz, 2H), 7.11 (d, J=8.8 Hz, 1H), 6.88 (dd, J=8.8, 2.2 Hz, 1H), 6.81 (s, 4H), 6.76 (d, J=8.6, 2H), 3.91 (bt, J=5.9 Hz, 2H), 3.77 (s, 3H), 2.55 (bt, J=5.9 Hz, 2H), 2.38–2.33 (m, 4H), 1.46–1.28 (m, 6H). FD mass spec 475. Anal. Calcd. for $C_{28}H_{29}NO_4S$: C, 70.71; H, 6.15; N, 2.94. Found: C, 71.00; H, 6.17; N, 2.94. Alternatively, Examples 39 and 40 can be prepared by the same transfer hydrogenolysis procedure directly in 90% yield from [6-methoxy-3-[4-[2-(1-piperidinyl)ethoxy] phenoxy]-2-(4-benzyloxyphenyl)]benzo[b]thiophene-(S-oxide) and [6-benzyloxy-3-[4-[2-(1-piperidinyl)ethoxy] phenoxy]-2-(4-methoxyphenyl)]benzo [b]thiophene-(S-oxide), respectively.

EXAMPLE 41

[6-Hydroxy-3-[4-[2-(1-piperidinyl)ethoxy]phenoxy]-2-(4-methoxyphenyl)]benzo[b]thiophene (Example 39) was converted to its hydrochloride salt in 85% yield by treatment with ethyl ether/hydrochloride in ethyl acetate followed by crystallization from ethanol/ethyl acetate

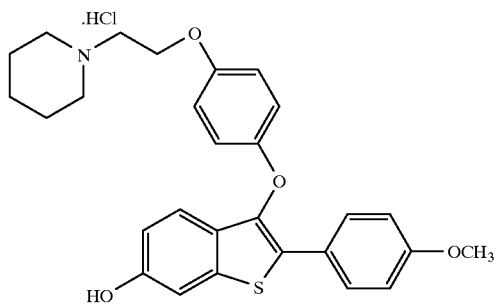

mp 156–160° C. $^1$H NMR (DMSO-$d_6$) d 10.28 (bs, 1H), 9.85 (s, 1H), 7.56 (d, J=8.8 Hz, 2H), 7.25 (d, J=2.0 Hz, 1H), 7.06 (d, J=8.7 Hz, 1H), 6.93 (d, J=8.8 Hz, 2H), 6.87 (q, $J_{AB}$=9.3 Hz, 4H), 4.27 (bt, J=5.9 Hz, 2H), 3.71 (s, 3H), 3.44–3.31 (m, 4H), 2.98–2.88 (m, 2H), 1.74–1.60 (m, 5H), 1.36–1.29 (m, 1H) FD mass spec 475. Anal. Calcd. for $C_{28}H_{29}NO_4S \cdot 1.0$ HCl: C, 65.68; H, 5.90; N, 2.73. Found: C, 65.98; H, 6.11; N, 2.64.

EXAMPLE 42

Prepared in a manner analogous to Example 41 was [6-hydroxy-3-[4-[2-(1-piperidinyl)ethoxy] phenoxy]-2-(4-methoxyphenyl)]benzo[b]thiophene hydrochloride

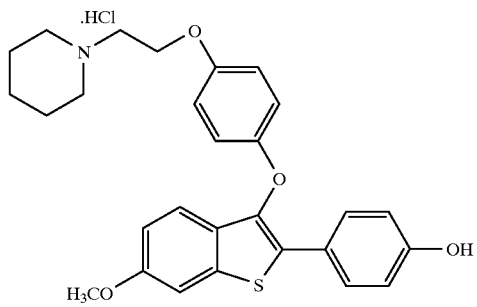

mp 215–217° C. $^1$H NMR (DMSO-$d_6$) d 10.28 (bs, 1H), 9.80 (s, 1H), 7.52 (d, J=2.2 Hz, 1H), 7.47 (d, J=8.6 Hz, 2H), 7.12 (d, J=8.4 Hz, 1H), 6.91–6.80 (m, 5H), 6.78 (d, J=8.6 Hz, 2H), 4.27 (bt, J=5.8 Hz, 2H), 3.78 (s, 3H), 3.43–3.34 (m, 4H), 2.97–2.91 (m, 2H), 1.78–1.61 (m, 5H), 1.36–1.29 (m, 1H). FD mass spec 475. Anal. Calcd. for $C_{28}H_{29}NO_4S \cdot 1.0$ HCl: C, 65.68; H, 5.90; N, 2.73. Found: C, 65.87; H, 5.79; N, 2.99.

EXAMPLE 43

[6-Benzoyloxy-3-[4-[2-(1-piperidinyl)-ethoxy]
phenoxy]-2-(4-benzoyloxyphenyl)]benzo[b]
thiophene hydrochloride

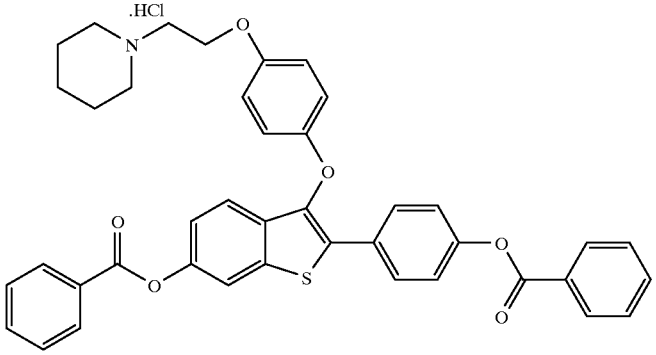

To a solution of Example 20 (0.50 g, 1.08 mmol) in 20 mL of anhydrous tetrahydrofuran at 0° C. was added triethylamine (1.00 mL). To this mixture was added benzoylchloride (0.28 mL, 2.35 mmol). After stirring at 0° C. for 2 hours, the reaction was quenched by distributing between ethyl acetate/saturated sodium bicarbonate solution (100 mL each). The layers were separated and the organic was dried (sodium sulfate) and concentrated in vacuo to a white solid. The crude product was dissolved in 10 mL of ethyl acetate and treated with ethyl ether.hydrochloric acid. A white precipitate formed that was collected by filtration. Drying provided 390 mg (50%) of [6-benzoyloxy-3-[4-[2-(1-piperidinyl) ethoxy]phenoxy]-2-(4-benzoyloxyphenyl)] benzo [b]thiophene hydrochloride as a white solid. mp 200–204° C. $^1$H NMR (DMSO-$d_6$) d 9.95 (bs, 1H), 8.18 (m, 1H), 8.16 (m, 2H), 8.12 (dd, J=10.0, 2.0 Hz, 2H), 7.87 (dd, J=7.0, 2.0 Hz, 2H), 7.78 (m, 2H), 7.64 (m, 2H), 7.42 (d, J=7.0 Hz, 2H), 7.34 (dd, J=8.0, 2.0 Hz, 1H), 7.00 (s, 4H), 4.32 (m, 2H), 3.45 (m, 4H), 2.99 (m, 2H), 1.75 (m, 5H), 1.39 (m, 1H). Anal. Calcd. for $C_{41}H_{35}NO_6S.1.5$ HCl: C, 67.97; H, 5.08; N, 1.93. Found: C, 68.05; H, 5.24; N, 2.01.

By the same procedure was prepared:

EXAMPLE 44

[6-Ethylsulfonyloxy-3-[4-[2-(1-piperidinyl)ethoxy]-
phenoxy]-2-(4-ethylsulfonyloxyphenyl)] benzo[b]
thiophene hydrochloride

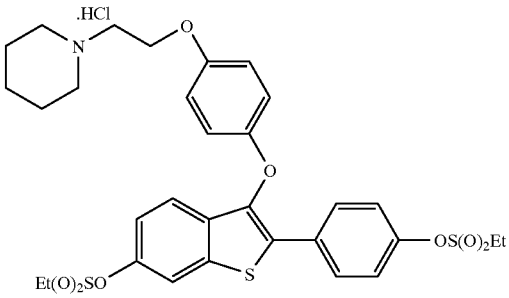

Yield=72%. mp 110–115° C. $^1$H NMR (DMSO-$d_6$) d 10.15 (bs, 1H), 8.15 (d, J=2.0 Hz, 1H), 7.85 (d, J=7.0 Hz, 2H), 7.43 (m, 3H), 7.34 (dd, J=9.0, 2.0 Hz, 1H), 6.97 (m, 4H), 4.31 (m, 2H), 3.57 (m, 4H), 3.44 (m, 4H), 2.97 (m, 2H), 1.76 (m, 5H), 1.40 (m, 7H). Anal. Calcd. for $C_{31}H_{35}NO_8S_3.1.5$ HCl: C, 54.57; H, 5.32; N, 2.05. Found: C, 54.36; H, 5.37; N, 2.05.

By a similar procedure employing triflouromethanesulfonic anhydride was:

EXAMPLE 45

[6-Methoxy-3-[4-[2-(1-piperidinyl)ethoxy]-
phenoxy]-2-(4-triflouromethanesulfonyloxyphenyl)]
benzo[b]thiophene

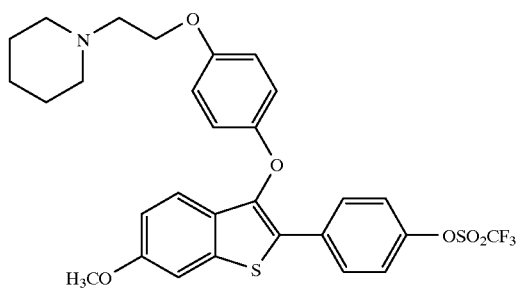

Yield=81%. Oil. $^1$H NMR (DMSO-$d_6$) d 7.82 (d, J=8.7 Hz, 2H), 7.60 (d, J=2.0 Hz, 1H), 7.54 (d, J=8.7 Hz, 2H), 7.17 (d, J=8.8 Hz, 1H), 6.93 (dd, J=8.8, 2.0 Hz, 1H), 6.84 (s, 4H), 3.92 (bt, J=5.7 Hz, 2H), 3.79 (s, 3H), 2.56 (bt, J=5.7 Hz, 2H), 2.36–2.30 (m, 4H), 1.44–1.31 (m, 6H). FD mass spec: 607. Anal. Calcd. for $C_{29}H_{28}NO_6F_3S_2$: C, 57.32; H, 4.64; N, 2.30. Found: C, 57.16; H, 4.52; N, 2.01.

Prepared from Example 1 by similar procedures were:

EXAMPLE 46

3-[4-[2-(1-piperidinyl)ethoxy]phenoxy]-2-(4-benzoyloxyphenyl)]benzo[b]thiophene hydrochloride

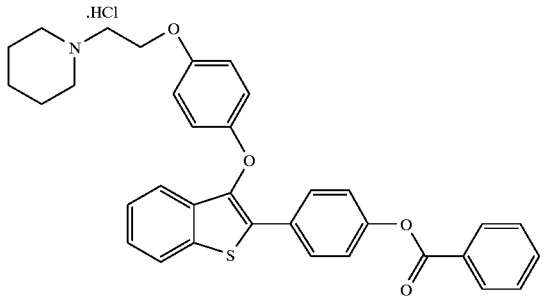

Yield=85%. mp 190–198° C. $^1$H NMR (DMSO-$d_6$) d 10.48 (br s, 1H), 8.00–8.10 (m, 2H), 7.80–8.00 (m, 3H), 7.60–7.53 (m, 4H), 7.40–7.56 (m, 6H), 6.93 (s, 2H), 4.37–4.43 (m, 2H), 3.00–3.05 (m, 2H), 2.53–2.63 (m, 6H), 1.75–1.95 (m, 3H), 1.40–1.50 (m, 1H) . FD mass spec: 550. Anal. Calcd. for $C_{34}H_{31}NO_4S.1.0$ HCl: C, 74.29; H, 5.68; N, 2.55. Found: C, 74.52; H, 5.80; N, 2.59.

EXAMPLE 47

3-[4-[2-(1-piperidinyl)ethoxy]phenoxy]-2-(4-pivaloyloxyphenyl)]benzo[b]thiophene hydrochloride

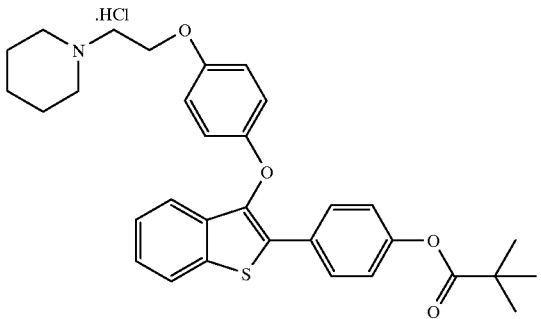

Yield=90%. mp=193–197° C. $^1$H NMR (DMSO-$d_6$) d 10.10 (br s, 1H), 8.12 (d, J=8.0 Hz, 1H), 7.85 (d, J=8.6 Hz, 1H), 7.40–7.53 (m, 3H), 7.15 (d, J=6.7 Hz, 2 H), 7.00 (s, 5H), 4.33–4.40 (m, 2H), 3.45–3.60 (m, 4H), 3.00–3.10 (m, 2H), 1.70–1.90 (m, 6H), 1.40 (s, 9H). FD mass spec: 529. Anal. Calcd. for $C_{32}H_{35}NO_4S.1.0$ HCl: C, 67.89; H, 6.41; N, 2.47. Found: C, 68.94; H, 6.61; N, 1.72.

EXAMPLE 48

3-[4-[2-(1-piperidinyl)ethoxy]phenoxy]-2-(4-butylsulfonyl-oxyphenyl)]benzo[b]thiophene hydrochloride

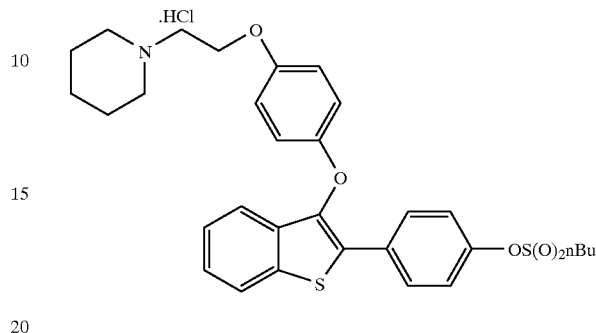

Yield=85% white solid. mp=98–104° C. $^1$H NMR (DMSO-$d_6$) d 10.20 (br s, 1H), 8.02 (d, J=8.0 Hz, 1H), 7.82 (d, J=8.7 Hz, 2H), 7.40–7.55 (m, 5H), 7.00 (s, 4H), 4.30–4.40 (m, 2H), 3.46–3.66 (m, 6H), 3.00–3.10 (m, 2H), 1.70–1.95 (m, 6H), 1.40–1.60 (m, 4H), 0.87 (t, J=7.3 Hz, 3H). FD mass spec: 565. Anal. Calcd. for $C_{31}H_{35}NO_5S_2.1.0$ HCl: C, 61.83; H, 6.03; N, 2.33. Found: C, 61.55; H, 6.15; N, 2.25.

Preparation 21

[6-Hydroxy-3-[4-[2-(1-piperidinyl)ethoxy]-thiophenoxy]-2-(4-hydroxyphenyl)]benzo[b]thiophene

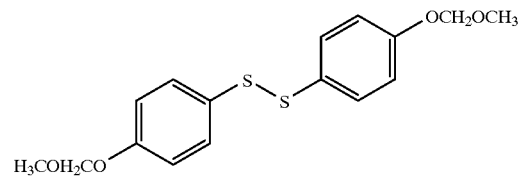

Preparation of 4-(methoxymethyloxy)phenyldisulfide.

To a solution of 4-hydroxyphenyldisulfide (650 mg, 2.60 mmol) in 10 mL of anhydrous N,N-dimethylformamide at 10° C. was added sodium hydride (230 mg, 5.75 mmol, 60% dispersion in mineral oil). After stirring for 15 minutes, chloromethylmethyl ether (0.44 mL, 5.75 mmol) was added via syringe. The reaction was warmed to ambient temperature and stirred for 0.5 hours. The mixture was distributed between brine/ethyl acetate (20 mL each). The layers were separated and the aqueous phase extracted with ethyl acetate (2×20 mL). The organic was dried (sodium sulfate) and concentrated to a yellow oil (993 mg, 100%). An analytical sample of 4-(methoxymethyloxy)-phenyldisulfide was prepared by chromatography (silicon dioxide, 4% ethyl acetate/hexanes). $^1$H NMR (DMSO-$d_6$) d 7.40 (d, J=6.9 Hz, 4H), 7.00 (d, J=6.9 Hz, 4H), 5.15 (s, 4H), 3.32 (s, 6H). FD mass spec: 338. Anal. Calcd. for $C_{16}H_{18}O_4S_2$: C, 56.78; H, 5.36. Found: c, 57.08; H, 5.44.

EXAMPLE 49

[6-Methoxy-2-(4-methoxyphenyl)-3-(4-methoxymethyleneoxy)thiophenoxy]benzo[b]thiophene

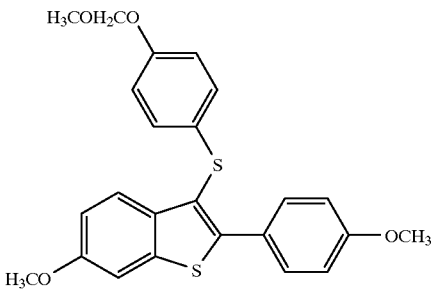

To a solution of [6-methoxy-2-(4-methoxyphenyl)-3-bromo]benzo[b]thiophene (1.82 g, 5.2 mmol) in 10 mL of anhydrous tetrahydrofuran under $N_2$ at −60° C. was added n-butyllithium (3.15 mL, 5.0 mmol, 1.6M solution in hexanes) dropwise via syringe. The resulting mixture was warmed to −20° C. for 10 minutes, then cooled back to −60° C. 4-(methoxymethyloxy)-phenyldisulfide (800 mg, 2.36 mmol) in 5 mL of anhydrous tetrahydrofuran was added to the lithio species, and the resultant mixture was allowed to gradually warm to 0° C. After stirring for 20 minutes, the reaction was quenched by distributing between brine/ethyl acetate (50 mL each). The layers were separated, and the aqueous phase was extracted with ethyl acetate(2×50 mL). The organic layer was combined, dried (sodium sulfate), and concentrated in vacuo to an oil. Chromatography (silicon dioxide, 5% ethyl acetate/hexanes) provided 287 mg (27%) of [6-methoxy-2-(4-methoxyphenyl)-3-(4-methoxymethyleneoxy)thiophenoxy] benzo[b]thiophene as a colorless oil. $^1$H NMR (DMSO-$d_6$) d 7.59 (d, J=8.4 Hz, 2H), 7.58 (d, J=2.0 Hz, 1H), 7.52 (d, J =8.8 Hz, 1H), 7.03–6.85 (m, 7H), 5.06 (s, 2H), 3.79 (s, 3H), 3.76 (s, 3H). FD mass spec: 438. Anal. Calcd. for $C_{24}H_{22}O_4S_2$: C, 65.73; H, 5.06. Found: C, 65.93; H, 5.10.

EXAMPLE 50

[6-Methoxy-2-(4-methoxyphenyl)-3-(4-hydroxy)thiophenoxy]benzo[b]thiophene

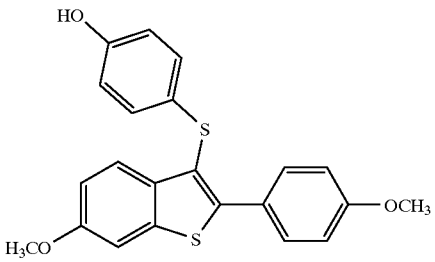

To a solution of [6-methoxy-2-(4-methoxyphenyl)-3-(4-methoxymethyleneoxy)thiophenoxy]benzo[b]thiophene (233 mg, 0.53 mmol) in 10 mL of a 1:1:2 mixture of methanol:water:tetrahydrofuran was added methane sulfonic acid (0.2 mL, 2.66 mmol). The mixture was heated to reflux for 5 hour. Upon cooling to ambient temperature, the reaction mixture was diluted with water. The aqueous phase was extracted with ethyl acetate (2×). The organic layer was washed with sat sodium bicarbonate solution several times. The organic layer was dried (sodium sulfate) and concentrated in vacuo to provide 206 mg (99%) of [6-methoxy-2-(4-methoxyphenyl)-3-(4-hydroxy)thiophenoxy]benzo-[b]thiophene as a colorless oil. $^1$H NMR (DMSO-$d_6$) d 9.43 (s, 1H), 7.63 (d, J=8.4 Hz, 2H), 7.61 (d, J=2.0 Hz, 1H), 7.59 (d, J=8.8 Hz, 1H), 7.08 (d, J=8.4 Hz, 2H), 7.02 (dd, J=8.8, 2.0 Hz, 1H), 6.90 (d, J=8.6 Hz, 2H), 6.63 (d, J=8.6 Hz, 2H). FD mass spec: 395. Anal. Calcd. for $C_{22}H_{18}O_3S_2$: C, 66.98; H, 4.60. Found: C, 67.26; H, 4.78.

EXAMPLE 51

[6-Methoxy-3-[4-[2-(1-piperidinyl)ethoxy]thiophenoxy]-2-(4-methoxyphenyl)]benzo[b]thiophene

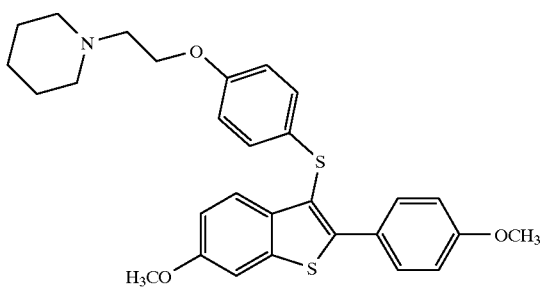

To a solution of [6-methoxy-2-(4-methoxyphenyl)-3-(4-hydroxy)thiophenoxy]benzo[b]thiophene (242 mg, 0.61 mmol) in 8.0 mL of anhydrous N,N-dimethylformamide was added cesium carbonate (820 mg, 2.5 mmol) followed by 2-chloroethylpiperidine hydrochloride (194 mg, 1.05 mmol). The resulting mixture was stirred for 48 hours at ambient temperature and then distributed between brine/ethyl acetate. The layers were separated, and the aqueous phase was extracted with ethyl acetate (3×). The organic layer was dried (sodium sulfate) and concentrated in vacuo to an oil. Chromatography (silicon dioxide, 0–2% methanol/chloroform) provided 244 mg (92%) of [6-methoxy-3-[4-[2-(1-piperidinyl) ethoxy]thiophenoxy]-2-(4-methoxyphenyl)]benzo-[b]thiophene as an amber oil.

EXAMPLE 52

A sample of [6-methoxy-3-[4-[2-(1-piperidinyl) ethoxy]-thiophenoxy]-2-(4-methoxyphenyl)]benzo[b]thiophene was converted to its hydrochloride salt according to the standard procedure in 72% yield

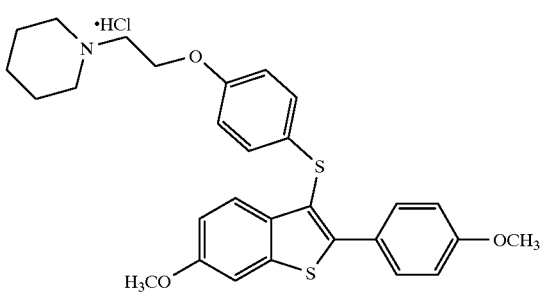

mp 198–201° C. $^1$H NMR (DMSO-$d_6$) d 7.63 (d, J=8.6 Hz, 2H), 7.62 (d, J=2.0 Hz, 1H), 7.58 (d, J=8.2 Hz, 1H), 7.07 (d, J=8.6 Hz, 2H), 7.02 (dd, J=8.2, 2.0 Hz, 1H), 6.92 (q, $J_{AB}$=9.0 Hz, 4H), 4.24 (bt, 2H), 3.82 (s, 3H), 3.80 (s, 3H), 3.49–3.39 (m, 4H), 2.93 (m, 2H), 1.82–1.62 (m, 5H), 1.38

(m, 1H). Anal. Calcd. for $C_{29}H_{32}NO_3S_2 \cdot 1.0$ HCl: C, 64.28; H, 5.95; N, 2.58. Found: C, 64.09; H, 6.08; N, 2.78.

EXAMPLE 53

[6-Hydroxy-3-[4-[2-(1-piperidinyl)ethoxy]-thiophenoxy]-2-(4-hydroxyphenyl)]benzo[b]thiophene

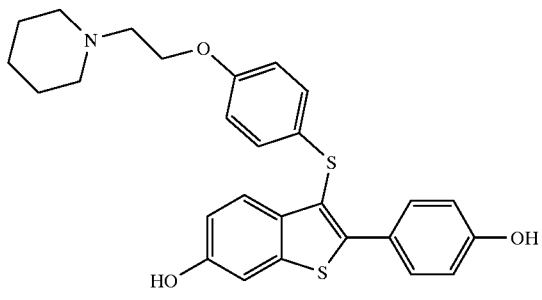

To a solution of [6-methoxy-3-[4-[2-(1-piperidinyl)ethoxy]-thiophenoxy]-2-(4-methoxyphenyl)]benzo[b]thiophene hydrochloride (160 mg, 0.29 mmol) in 15 mL of anhydrous methylene chloride at 0° C. under $N_2$ was added boron tribromide (0.15 mL). The resulting dark solution was stirred for 1 hour at 0° C. and then immediately poured into a stirred solution of ethyl acetate/sat sodium bicarbonate solution (50 mL each). The layers were separated, and the aqueous phase was washed with ethyl acetate (3×30 mL). The organic was dried (sodium sulfate) and concentrated in vacuo to a white solid. Chromatography (silicon dioxide, 0–5% methanol/ chloroform) provided 91 mg (60%) of [6-hydroxy-3-[4-[2-(1-piperidinyl)ethoxy]thiophenoxy]-2-(4-hydroxyphenyl)]benzo[b]-thiophene as a white solid. mp 123–127° C. $^1$H NMR (DMSO-$d_6$) d 9.79 (s, 1H), 9.71 (s, 1H), 7.46 (d, J=8.4 Hz, 2H), 7.42 (d, J=8.9 Hz, 1H), 7.26 (d, J=2.0 Hz, 1H), 6.91 (d, J=8.8 Hz, 2H), 6.82–6.76 (m, 5H), 3.91 (t, J=8.8 Hz, 2H), 2.56 (t, J=5.8 Hz, 2H), 2.40 (m, 4H), 1.41–1.28 (m, 6H). FD mass spec: 478. Anal. Calcd. for $C_{27}H_{27}NO_3S_2$: C, 67.90; H, 5.70; N, 2.93. Found: C, 68.14; H, 5.84; N, 2.65.

EXAMPLE 54

[6-Hydroxy-3-[4-[2-(1-piperidinyl)ethoxy]thiophenoxy]-2-(4-hydroxyphenyl)]benzo[b]thiophene hydrochloride

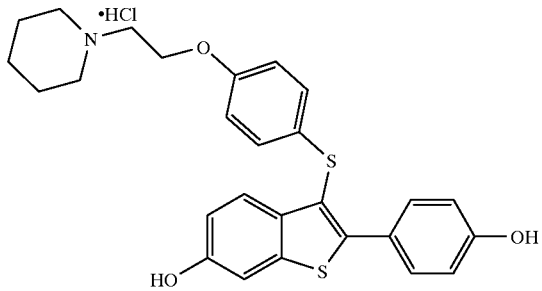

mp 180–190° C. $^1$H NMR (DMSO-$d_6$) d 9.86 (s, 1H), 9.79 (s, 1H), 7.46 (d, J=8.5 Hz, 2H), 7.42 (d, J=8.7 Hz, 1H), 7.29 (d, J=2.0 Hz, 1H), 6.96 (d, J=8.7 Hz, 2H), 6.86–6.81 (m, 5H), 4.27 (m, 2H), 3.41–3.37 (m, 4H), 2.96–2.84 (m, 2H), 1.77–1.60 (m, 5H), 1.35–1.28 (m, 1H). FD mass spec: 477. Anal. Calcd. for $C_{27}H_{27}NO_3S_2 \cdot 2.2$ HCl: C, 58.13; H, 5.28; N, 2.51. Found: C, 58.11; H, 5.10; N, 2.61.
Prepared by the same procedures were:

EXAMPLE 55

[6-Methoxy-3-[4-[2-(1-pyrolodinyl)ethoxy]thiophenoxy]-2-(4-methoxyphenyl)]benzo[b]thiophene hydrochloride

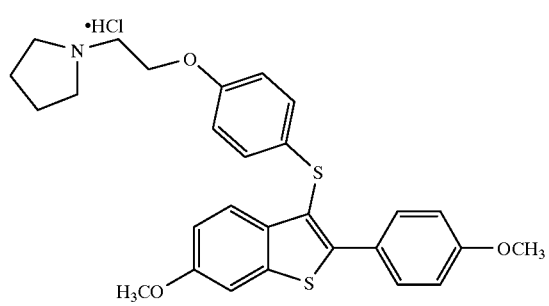

mp 215–218° C. $^1$H NMR (DMSO-$d_6$) d 7.61–7.58 (m, 3H), 7.52 (d, J=8.8 Hz, 1H), 7.04–6.95 (m, 5H), 6.86 (d, J=8.8 Hz, 2H), 4.22 (bt, 2H), 3.79 (s, 3H), 3.76 (s, 3H), 3.47–3.42 (m, 4H), 3.01 (m, 2H), 1.94–1.80 (m, 4H). FD mass spec: 491. Anal. Calcd. for $C_{28}H_{29}NO_3S_2 \cdot 1.0$ HCl: C, 63.67; H, 5.73; N, 2.65. Found: C, 63.47; H, 5.78; N, 2.65.

EXAMPLE 56

[6-Hydroxy-3-[4-[2-(1-pyrolodinyl)ethoxy]thiophenoxy]-2-(4-hydroxyphenyl)]benzo[b]thiophene hydrochloride

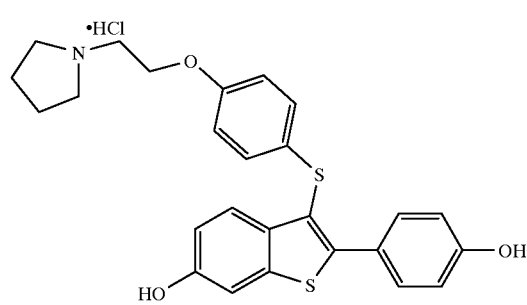

mp 137–140° C. (dec). $^1$H NMR (DMSO-$d_6$) d 9.86 (s, 1H), 9.80 (s, 1H), 7.46 (d, J=8.6 Hz, 2H), 7.42 (d, J=8.7 Hz, 1H), 7.29 (d, J=2.0 Hz, 1H), 6.96 (d, J=8.7 Hz, 2H), 6.87–6.81 (m, 5H), 4.21 (bt, 2H), 3.53–3.41 (m, 4H), 3.01 (m, 2H), 1.95–1.82 (m, 4H). FD mass spec: 464. Anal. Calcd. for $C_{26}H_{25}NO_3S_2 \cdot 1.0$ HCl: C, 62.45; H, 5.24; N, 2.80. Found: C, 62.36; H, 5.37; N, 2.61.

EXAMPLE 57

Prepared from the product of Example 45 by the hydrogenolysis of the triflate as described below in Example 58 was 6-methoxy-3-[4-[2-(1-piperidinyl)ethoxy]phenoxy]-2-(phenyl)]benzo[b]thiophene hydrochloride

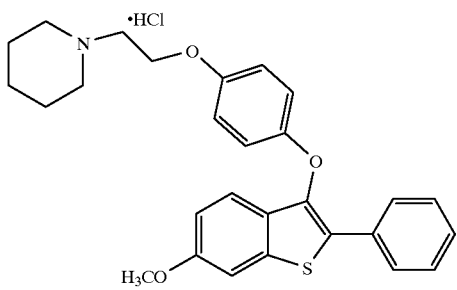

mp 187–195° C. $^1$H NMR (DMSO-$d_6$) d 7.66 (d, J=2.8 Hz, 2H), 7.58 (d, J=2.0 Hz, 1H), 7.39 (t, J=7.5 Hz, 2H), 7.28 (m, 1H), 7.17 (d, J=8.8 Hz, 1H), 6.91 (dd, J=8.8, 2.0 Hz, 1H), 6.89 (S, 4H), 4.23 (bt, J=5.7 Hz, 2H), 3.79 (s, 3H), 3.45–3.38 (m, 4H), 2.98 (m, 2H), 1.77–1.61 (m, 5H), 1.31 (m, 1H). FD mass spec: 460. Anal. Calcd. for $C_{28}H_{29}NO_3S \cdot 1.0$ HCl: C, 67.80; H, 6.10; N, 2.84. Found: C, 67.62; H, 5.89; N, 2.67.

EXAMPLE 58

6-Hydroxy-3-[4-[2-(1-piperidinyl)ethoxy]phenoxy]-2-(phenyl)]benzo[b]thiophene hydrochloride

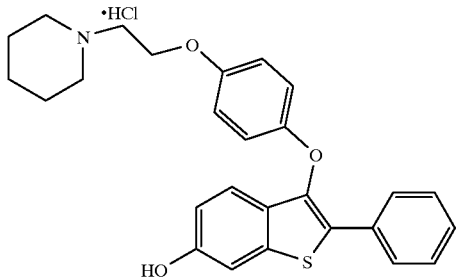

To a solution of 6-hydroxy-3-[4-[2-(1-piperidinyl)ethoxy]phenoxy]-2-(4-hydroxyphenyl)]benzo[b]thiophene hydrochloride (5.00 g, 10.0 mmol) in 100 mL of anhydrous methylene chloride at 0° C. under $N_2$ was added triethylamine (8.38 mL, 60.0 mmol) followed by triflouromethanesulfonic anhydride (1.69 mL, 10.0 mmol). The resulting mixture was allowed to gradually warm to room temperature and stirred for 1.5 hours. The reaction was then quenched by pouring into 200 mL of saturated sodium bicarbonate solution. The aqueous phase was then extracted with ethyl acetate (3×100 mL). The organic layer was dried (sodium sulfate) and concentrated in vacuo to an oil. Chromatography (0–3% methanol/chloroform) provided 2.82 g (39%) of 6-triflouromethanesulfonate-3-[4-[2-(1-piperidinyl)ethoxy]phenoxy]-2-(4-triflouromethane-sulfonatephenyl)]benzo[b]thiophene, 1.82 g (31%) of a 1:1 mixture of 6-triflouromethanesulfonate-3-[4-[2-(1-piperidinyl)ethoxy]phenoxy]-2-(4-phenyl)]benzo[b]thiophene and 3-[4-[2-(1-piperidinyl)ethoxy]phenoxy]-2-(4-triflouromethanesulfonatephenyl)]benzo[b]thiophene, and 1.48 g (36%) of recovered staring material as the free base.

To a solution of a 1:1 mixture of monotriflate derivatives from the last reaction (0.50 g, 0.84 mmol) in 60 mL of ethanol-ethyl acetate (5:1) was added triethylamine (2.0 mL) and 5% palladium-on-carbon (0.50 g). The resulting mixture was hydrogenated at 40 psi for 2 hours. The mixture was then filtered through Celite® to remove the catalyst. The filtrate was concentrated to an oil. The resulting mixture of monohydroxy derivatives was dissolved in ethyl acetate from which 3-[4-[2-(1-piperidinyl)ethoxy]phenoxy]-2-(4-hydroxyphenyl)]benzo[b]-thiophene precipitated. The filtrate consisted of a 4:1 mixture of monohydroxy derivatives where 6-hydroxy-3-[4-[2-(1-piperidinyl)ethoxy]phenoxy]-2-(phenyl)]benzo[b]thiophene was the major component. The filtrate was concentrated in vacuo, and the resulting solid dissolved in minimal ethyl acetate and treated with ethyl ether hydrochloric acid. The resulting solid was recrystallized from ethanol to give 69 mg (18%) of isomerically pure 6-hydroxy-3-[4-[2-(1-piperidinyl)ethoxy]phenoxy]-2-(phenyl)]benzo[b]thiophene hydrochloride. mp 217–219° C. $^1$H NMR (DMSO-$d_6$) d 9.87 (s, 1H), 7.64 (d, J=7.5 Hz, 2H), 7.39–7.26 (m, 4H), 7.10 (d, J=8.6 Hz, 1H), 6.89 (s, 4H), 6.78 (dd, J=8.6, 2.0 Hz, 1H), 4.22 (bt, 2H), 3.39–3.37 (m, 4H), 2.97–2.90 (m, 2H), 1.74–1.60 (m, 5H), 1.39 (m, 1H). FD mass spec: 446. Anal. Calcd. for $C_{27}H_{27}NO_3S \cdot 1.0$ HCl: C, 67.28; H, 5.86; N, 2.91. Found: C, 67.00; H, 5.59; N, 2.87. Alternatively, Example 58 is prepared by demethylation of the product of Example 57 as described in Example 18.

EXAMPLE 59

[6-Isoprpoxy-3-[4-[2-(1-piperidinyl)ethoxy]phenoxy]-2-(4-methoxyphenyl)]benzo[b]thiophene-(S-oxide) was prepared as described for [6-methoxy-3-[4-[2-(1-piperidinyl)ethoxy]phenoxy]-2-(4-methoxyphenyl)]benzo[b]thiophene-(S-oxide) (Example 30).

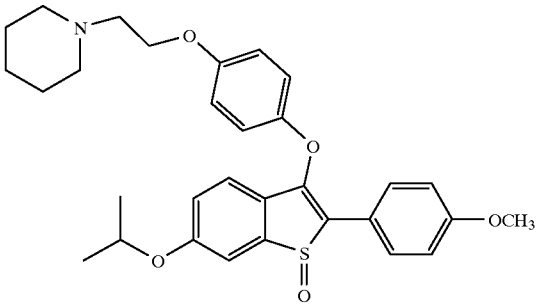

Yellow oil. $^1$H NMR (DMSO-$d_6$) d 7.69 (d, J=2.0 Hz, 1H), 7.67(d, J=8.6 Hz, 2H), 7.09–6.99 (m, 5H), 6.96–6.87 (m, 3H), 4.76 (septet, J=6.0 Hz, 1H), 3.99 (bt, J=6.0 Hz, 2H), 3.78 (s, 3H), 2.61 (bt, J=6.0 Hz, 2H), 2.44–2.37 (m, 4H), 1.53–1.43 (m, 4H), 1.40–1.32 (m, 2H), 1.29 (d, J=6.0 Hz, 6H). FD mass spec 533. Anal. Calcd. for $C_{31}H_{35}NO_5S \cdot 0.67$ $H_2O$: C, 68.23; H, 6.71; N, 2.57. Found: C, 67.90; H, 6.31; N, 2.53.

[6-Isoprpoxy-3-[4-[2-(1-piperidinyl)ethoxy]phenoxy]-2-(4-methoxyphenyl)]benzo[b]thiophene hydrochloride was prepared as described for [6-methoxy-3-[4-[2-(1-piperidinyl)ethoxy]phenoxy]-2-(4-methoxyphenyl)]benzo[b]thiophene (Example 32).

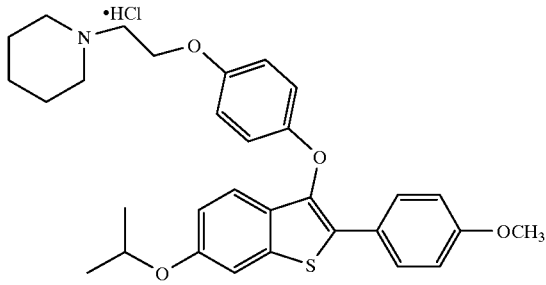

mp 168–170° C. $^1$H NMR (DMSO-$d_6$) d 10.37 (s, 1H), 7.58 (d, J=8.6 Hz, 2H), 7.52 (d, J=1.3 Hz, 1H), 7.12 (d, J=8.8 Hz, 1H), 6.95 (d, J=8.6 Hz, 2H), 6.92–6.85 (m, 5H), 4.64 (septet, J=6.0 Hz, 1H), 4.28 (bt, J=6.0 Hz, 2H), 3.72 (s, 3H), 3.44–3.37 (m, 4H), 2.95–2.89 (m, 2H), 1.73–1.60 (m, 5H), 1.36–1.28 (m, 1H), 1.25 (d, J=6.0 Hz, 6H). FD mass spec 517. Anal. Calcd. for $C_{31}H_{35}NO_4S \cdot HCl$: C, 67.19; H, 6.55; N, 2.53. Found: C, 67.15; H, 6.29; N, 2.62.

[6-Isoprpoxy-3-[4-[2-(1-piperidinyl)ethoxy]phenoxy]-2-(4-methoxyphenyl)]benzo[b]thiophene hydrochloride was converted to [6-hydroxy-3-[4-[2-(1-piperidinyl)ethoxy]phenoxy]-2-(4-methoxyphenyl)]benzo[b]thiophene by treatment with 2.0 equivalents of $BCl_3$ at 0–10° C. in anhydrous dichloromethane (the methyl ether is not cleaved under these conditions).

Test Procedure

General Preparation Procedure

In the examples illustrating the methods, a postmenopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection

After a one week acclimation period (therefore, two weeks post-OVX) daily dosing with test compound was initiated. 17a-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine: Xylazine (2:1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis

Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve. The entire assay was automated using a Biomek Automated Workstation.

Uterine Eosinophil Peroxidase (EPO) Assay

Uteri were kept at 4° C. until time of enzymatic analysis. The uteri were then homogenized in 50 volumes of 50 mM Tris buffer (pH-8.0) containing 0.005% Triton X-100. Upon addition of 0.01% hydrogen peroxide and 10 mM O-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound 17a-ethynyl estradiol was obtained from Sigma Chemical Co., St. Louis, Mo.

Influence of Formula I Compounds on Serum Cholesterol and Determination of Agonist/Non-Aaonist Activity Data presented in Table 1 below show comparative results among ovariectomized rats, rats treated with 17a-ethynyl estradiol ($EE_2$; an orally available form of estrogen), and rats treated with certain compounds of the present invention. Although $EE_2$ caused a decrease in serum cholesterol when orally administered at 0.1 mg/kg/day, it also exerted a stimulatory action on the uterus so that $EE_2$ uterine weight was substantially greater than the uterine weight of ovariectomized test animals. This uterine response to estrogen is well recognized in the art.

Not only did the compounds of the present invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the below data, estrogenicity also was assessed by evaluating the adverse response of eosinophil infiltration into the uterus. The compounds of the present invention did not cause any increase in the number of eosinophils observed in the stromal layer of ovariectomized rats, while estradiol cause a substantial, expected increase in eosinophil infiltration.

The data presented in the Tables 1 below reflects the response of 5 to 6 rats per treatment.

TABLE 1

| Compound | Dose mg/kg | Uterine Weight (% increase vs. OVX) | Uterine EPO (v. max) | Serum Cholesterol (% decrease vs. OVX) |
|---|---|---|---|---|
| $EE_2$ | 0.1 | 229.2 | 308.1 | 94.8 |
| Example 3 | 0.01 | 29.1 | 1.8 | 50.6 |
|  | 0.1 | 55.4 | 4.8 | 47.8 |
|  | 1.0 | 61.9 | 5.4 | 49.2 |
| Example 4 | 0.1 | 33.2 | 3.9 | 53.7 |
|  | 1.0 | 35.6 | 4.8 | 62.1 |
|  | 10.0 | 34.7 | 3.0 | 65.3 |
| Example 5 | 0.1 | 66.7 | 7.2 | 67.2 |
|  | 1.0 | 106.9 | 54.6 | 67.7 |
|  | 10.0 | 109.8 | 59.4 | 60.2 |

TABLE 1-continued

| Compound | Dose mg/kg | Uterine Weight (% increase vs. OVX) | Uterine EPO (v. max) | Serum Cholesterol (% decrease vs. OVX) |
|---|---|---|---|---|
| Example 7 | 0.1 | 32.0 | 4.8 | 56.2 |
| | 1.0 | 44.3 | 4.5 | 42.6 |
| | 5.0 | 41.6 | 4.8 | 29.5 |
| Example 10 | 0.1 | 19.7 | 12.0 | 50.2 |
| | 1.0 | 18.4 | 17.7 | 59.0 |
| | 10.0 | 13.3 | 4.8 | 38.9 |
| Example 19 | 0.01 | 11.4 | 2.1 | 25.1 |
| | 0.1 | 24.9 | 2.4 | 45.3 |
| | 1.0 | 24.7 | 3.6 | 53.6 |
| Example 20 | 0.01 | 16.9 | 0.9 | 29.4 |
| | 0.05 | 40.9 | 3.0 | 35.9 |
| | 0.1 | 30.6 | 3.0 | 58.7 |
| Example 21 | 0.01 | 21.0 | 1.2 | 26.8 |
| | 0.1 | 24.8 | 4.8 | 47.5 |
| | 1.0 | 51.4 | 9.3 | 54.4 |
| Example 23 | 0.01 | 21.6 | 3.3 | 36.2 |
| | 0.1 | 33.4 | 84.3 | 47.2 |
| | 1.0 | 148.9 | 150.6 | 66.1 |
| Example 24 | 0.01 | 9.2 | 3.6 | 23.7 |
| | 0.1 | 18.2 | 0.9 | 46.4 |
| | 1.0 | 81.0 | 29.4 | 79.3 |
| Example 25 | 0.01 | 5.4 | 3.0 | 13.1 |
| | 0.1 | 16.7 | 3.3 | 67.6 |
| | 1.0 | 96.6 | 36.0 | 73.9 |
| Example 26 | 0.01 | 14.0 | 4.8 | 29.0 |
| | 0.1 | 81.0 | 29.1 | 45.2 |
| | 1.0 | 117.1 | 175.1 | 62.7 |
| Example 27 | 0.01 | 2.2 | 3.3 | 12.2 |
| | 0.1 | 49.2 | 4.8 | 50.8 |
| | 1.0 | 86.4 | 52.5 | 76.5 |
| Example 43 | 0.01 | 0.0 | 3.39.2 | |
| | 0.1 | 17.2 | 4.8 | 43.8 |
| | 1.0 | 31.0 | 6.0 | 39.4 |
| Example 44 | 0.01 | 43.8 | 3.6 | 12.6 |
| | 0.1 | 80.5 | 88.5 | 43.8 |
| | 1.0 | 74.8 | 94.5 | 67.4 |
| Example 53 | 0.1 | 40.6 | 0.9 | 62.7 |
| | 1.0 | 24.1 | 1.3 | 57.5 |
| | 10.0 | 32.0 | 4.8 | 58.7 |

In addition to the demonstrated benefits of the compounds of the present invention, especially when compared to estradiol, the above data clearly demonstrate that compounds of Formula I are not estrogen mimetics. Furthermore, no deleterious toxicological effects (survival) were observed with any treatment.

Osteoporosis Test Procedure

Following the General Preparation Procedure, infra, the rats were treated daily for 35 days (6 rats per treatment group) and sacrificed by carbon dioxide asphyxiation on the 36th day. The 35 day time period was sufficient to allow maximal reduction in bone density, measured as described herein. At the time of sacrifice, the uteri were removed, dissected free of extraneous tissue, and the fluid contents were expelled before determination of wet weight in order to confirm estrogen deficiency associated with complete ovariectomy. Uterine weight was routinely reduced about 75% in response to ovariectomy. The uteri were then placed in 10% neutral buffered formalin to allow for subsequent histological analysis.

The right femurs were excised and digitilized x-rays generated and analyzed by an image analysis program (NIH image) at the distal metaphysis. The proximal aspect of the tibiae from these animals were also scanned by quantitative computed tomography.

In accordance with the above procedures, compounds of the present invention and ethynyl estradiol ($EE_2$) in 20% hydroxypropyl b-cyclodextrin were orally administered to test animals. Distal femur metaphysis data presented in Tables 2 and 3 below are the results of formula I compound treatments compared to intact and ovariectomized test animals. Results are reported as the mean ± the standard error of the mean.

TABLE 2

| Compound/Treatment | Dose /kg | Distal Femur Metaphysis (x-ray Image Analysis-Gray Score) |
|---|---|---|
| Sham (20% cyclodextrin) | — | 27.2 ± 6.0 |
| Overiectomy control (20% cyclodextrin) | — | 8.1 ± 1.8 |
| EE2 | 0.1 mg | 11.5 ± 2.9* |
| Example 19 | 0.1 mg | 14.7 ± 1.9 |
| | 1.0 mg | 15.0 ± 3.5* |
| | 10.0 mg | 15.3 ± 4.0* |

*P <= 0.5 two tailed Student's T Test on raw data.

TABLE 3

| Compound/Treatment | Dose /kg | Distal Femur Metaphysis (X-ray Image Analysis-Gray Score) |
|---|---|---|
| Sham (20% cyclodextrin) | — | 31.1 ± 6.3 |
| Overiectomy control (20% cyclodextrin) | — | 6.2 ± 1.4 |
| EE2 | 0.1 mg | 17.8 ± 3.5 |
| Example 10 | 0.1 mg | 15.3 ± 3.0 |
| | 1.0 mg | 15.2 ± 3.7 |
| | 3.0 mg | 18.5 ± 3.2* |
| Example 24 | 0.1 mg | 18.3 ± 2.6* |
| | 1.0 mg | 19.6 ± 2.3* |
| | 3.0 mg | 17.1 ± 5.5 |

*P <= 0.05 two tailed Student's Test on raw data.

In summary, ovariectomy of the test animals caused a significant reduction in femur density compared to intact, vehicle treated controls. Orally administered ethynyl estradiol ($EE_2$) prevented this loss, but the risk of uterine stimulation with this treatment is ever-present.

The compounds of the present invention also prevented bone loss in a general, dose-dependent manner. Accordingly, the compounds of the present invention are useful for the treatment of post-menopausal syndrome, particularly osteoporosis.

MCF-7 Proliferation Assay

MCF-7 breast adenocarcinoma cells (ATCC HTB 22) were maintained in MEM (minimal essential medium, phenol red-free, Sigma, St. Louis, Mo.) supplimented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 ug/mL) (maintenance medium). Ten days prior to assay, MCF-7 cells were switched to maintenance medium supplemented with 10% dextran coated charcoal stripped fetal bovine serum (DCC-FBS) assay medium) in place of 10% FBS to deplete internal stores of steroids. MCF-7 cells were removed from maintenance flasks using cell dissociation medium (Ca++/Mg++ free HBSS (phenol red-free) supplemented with 10 mM HEPES and 2 mM EDTA). Cells were washed twice with assay medium and adjusted to 80,000 cells/mL. Approximately 100 mL (8,000 cells) were added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control were prepared in assay medium and 50 mL transferred to triplicate microcultures followed by 50 mL assay medium for a final volume of 200 mL. After an additional 48 hours at 37° C. in a 5% $CO_2$ humidified incubator, microcultures were pulsed with tritiated thymidine (1 uCi/well) for 4 hours. Cultures were terminated by freezing at −70° C. for 24 hours followed by thawing and harvesting of microcultures using a Skatron Semiautomatic Cell Harvester. Samples were counted by liquid scintillation using a Wallac BetaPlace b counter. Results in Table 4 below show the $IC_{50}$ for certain compounds of the present invention.

TABLE 4

| Compound | $IC_{50}$nM |
|---|---|
| Example 3 | 4.0 |
| Example 10 | 2.00 |
| Example 19 | 0.028 |
| Example 21 | 0.05 |
| Example 23 | 0.08 |
| Example 53 | 0.28 |

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

Uterine Fibrosis Test Procedures

Test 1

Between 3 and 20 women having uterine fibrosis are administered a compound of the present invention. The amount of compound administered is from 0.1 to 1000 mg/day, and the period of administration is 3 months.

The women are observed during the period of administration, and up to 3 months after discontinuance of administration, for effects on uterine fibrosis.

Test 2

The same procedure is used as in Test 1, except the period of administration is 6 months.

Test 3

The same procedure is used as in Test 1, except the period of administration is 1 year.

Test 4

A. Induction of fibroid tumors in guinea pig.

Prolonged estrogen stimulation is used to induce leiomyomata in sexually mature female guinea pigs. Animals are dosed with estradiol 3–5 times per week by injection for 2–4 months or until tumors arise. Treatments consisting of a compound of the invention or vehicle is administered daily for 3–16 weeks and then animals are sacrificed and the uteri harvested and analyzed for tumor regression.

B. Implantation of human uterine fibroid tissue in nude mice.

Tissue from human leiomyomas are implanted into the peritoneal cavity and or uterine myometrium of sexually mature, castrated, female, nude mice. Exogenous estrogen are supplied to induce growth of the explanted tissue. In some cases, the harvested tumor cells are cultured in vitro prior to implantation. Treatment consisting of a compound of the present invention or vehicle is supplied by gastric lavage on a daily basis for 3–16 weeks and implants are removed and measured for growth or regression. At the time of sacrifice, the uteri is harvested to assess the status of the organ.

Test 5

A. Tissue from human uterine fibroid tumors is harvested and maintained, in vitro, as primary nontransformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the present invention and vehicle. Levels of steroid hormone receptors are assessed weekly to determine whether important cell characteristics are maintained in vitro. Tissue from 5–25 patients are utilized.

Activity in at least one of the above tests indicates the compounds of the present invention are of potential in the treatment of uterine fibrosis.

Endometriosis Test Procedure

In Tests 1 and 2, effects of 14-day and 21-day administration of compounds of the present invention on the growth of explanted endometrial tissue can be examined.

Test 1

Twelve to thirty adult CD strain female rats are used as test animals. They are divided into three groups of equal numbers. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. In addition, females in Group 2 have the ovaries removed.

On the day following surgery, animals in Groups 1 and 2 receive intraperitoneal injections of water for 14 days whereas animals in Group 3 receive intraperitoneal injections of 1.0 mg of a compound of the present invention per kilogram of body weight for the same duration. Following 14 days of treatment, each female is sacrificed and the endometrial explants, adrenals, remaining uterus, and ovaries, where applicable, are removed and prepared for histological examination. The ovaries and adrenals are weighed.

Test 2

Twelve to thirty adult CD strain female rats are used as test animals. They are divided into two equal groups. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow.

Approximately 50 days following surgery, animals assigned to Group 1 receive intraperitoneal injections of water for 21 days whereas animals in Group 2 receive intraperitoneal injections of 1.0 mg of a compound of the present invention per kilogram of body weight for the same duration. Following 21 days of treatment, each female is sacrificed and the endometrial explants and adrenals are removed and weighed. The explants are measured as an indication of growth. Estrous cycles are monitored.

Test 3

A. Surgical induction of endometriosis

Autographs of endometrial tissue are used to induce endometriosis in rats and/or rabbits. Female animals at reproductive maturity undergo bilateral oophorectomy, and estrogen is supplied exogenously thus providing a specific and constant level of hormone. Autologous endometrial tissue is implanted in the peritoneum of 5–150 animals and estrogen supplied to induce growth of the explanted tissue. Treatment consisting of a compound of the present invention is supplied by gastric lavage on a daily basis for 3–16 weeks, and implants are removed and measured for growth or regression. At the time of sacrifice, the intact horn of the uterus is harvested to assess status of endometrium.

B. Implantation of human endometrial tissue in nude mice

Tissue from human endometrial lesions is implanted into the peritoneum of sexually mature, castrated, female, nude mice. Exogenous estrogen is supplied to induce growth of the explanted tissue. In some cases, the harvested endometrial cells are cultured in vitro prior to implantation. Treatment consisting of a compound of the present invention supplied by gastric lavage on a daily basis for 3–16 weeks, and implants are removed and measured for growth or regression. At the time of sacrifice, the uteri is harvested to assess the status of the intact endometrium.

Test 4

A. Tissue from human endometrial lesions is harvested and maintained in vitro as primary nontransformed cultures.

Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the invention, and vehicle. Levels of steroid hormone receptors are assessed weekly to determine whether important cell characteristics are maintained in vitro. Tissue from 5–25 patients is utilized.

Activity in any of the above assays indicates that the compounds of the present invention are useful in the treatment of endometriosis.

The present invention also provides a method of alleviating post-menopausal syndrome in women which comprises the aforementioned method using compounds of Formula I and further comprises administering to a woman an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, infra, indicates that the combination treatments are useful for alleviating the symptoms of post-menopausal symptoms in women.

Various forms of estrogen and progestin are commercially available. Estrogen-based agents include, for example, ethynyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin, and norethylnodrel and norethindrone are preferred progestin-based agents.

The method of administration of each estrogen- and progestin-based agent is consistent with that which is known in the art. For the majority of the methods of the present invention, compounds of Formula I are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 5 mg to about 600 mg/day of a compound of the present invention. Preferred daily doses generally will be from about 15 mg to about 80 mg/day.

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well known and readily available ingredients. For example, the compounds of formula I, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I, alone or in combination with a pharmaceutical agent of the present invention, generally will be administered in a convenient formulation. The following formulation examples only are illustrative and are not intended to limit the scope of the present invention.

Formulations

In the formulations which follow, "active ingredient" means a compound of formula I, or a salt or solvate thereof.

Formulation 1: Gelatin Capsules

Hard gelatin capsules are prepared using the

| Ingredient | Quantity (mg/capsule) |
| --- | --- |
| Active ingredient | 0.1–1000 |
| Starch, NF | 0–650 |
| Starch flowable powder | 0–650 |
| Silicane fluid 350 centistokes | 0–15 |

The formulation above may be changed in compliance with the reasonable variations provided.

A tablet formulation is prepared using the ingredients below:

Formulation 2: Tablets

| Ingredient | Quantity (mg/tablet) |
| --- | --- |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

Formulation 3: Tablets

| Ingredient | Quantity (mg/tablet) |
| --- | --- |
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

Formulation 4: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity | |
| --- | --- | --- |
| Active ingredient | 50 | mg |
| Isotonic saline | 1,000 | mL |

The solution of the above ingredients is intravenously administered to a patient at a rate of about 1 mL per minute.

| Formulation 8: Combination Capsule I | |
|---|---|
| Ingredient | Quantity (mg/capsule) |
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

| Formulation 9: Combination Capsule II | |
|---|---|
| Ingredient | Quantity (mg/capsule) |
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

| Formulation 10: Combination Tablet | |
|---|---|
| Ingredient | Quantity (mg/capsule) |
| Active ingredient | 50 |
| Premarin | 1 |
| Corn Starch NF | 50 |
| Povidone, K29–32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

I claim:

1. A method for inhibiting estrogen-dependent cancer comprising administering co a patient in need of such treatment an effective amount of a compound of the formula

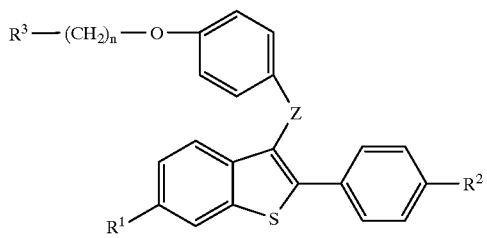

wherein $R^1$ is —H, —OH, —O($C_1$–$C_4$ alkyl), —OCOC$_6$H$_5$, —OCO($C_1$–$C_6$ alkyl), or —OSO$_2$($C_2$–$C_6$ alkyl);

$R^2$ is —H, —OH, —O($C_1$–$C_4$ alkyl), —OCOC$_6$H$_5$, —OCO($C_1$–$C_6$ alkyl), —OSO$_2$($C_2$–$C_6$ alkyl) or halo;

$R^3$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;

n is 2 or 3; and

Z is —O— or —S—;

or a pharmaceutically acceptable salt thereof; together with a progestin selected from progesterone, norethylnodrel, nongestrel, megestrol acetate and norethindrone.

2. A method according to claim 1 wherein Z is —O—, n is 2, and $R^3$ is 1-piperidinyl, or a pharmaceutically acceptable salt thereof.

3. A method according to claim 2 wherein $R^1$ and $R^2$ each are —O($C_1$–$C_4$ alkyl), or a pharmaceutically acceptable salt thereof.

4. A method according to claim 3 wherein $R^1$ and $R^2$ each are —OCH$_3$, or a pharmaceutically acceptable salt thereof.

5. A method according to claim 4 wherein said salt thereof is the hydrochloride salt.

6. A method according to claim 2 wherein $R^1$ is —OH and $R^2$ is —O($C_1$–$C_4$ alkyl), or a pharmaceutically acceptable salt thereof.

7. A method according to claim 1 wherein said estrogen dependent cancer is breast or uterine cancer.

8. A method for inhibiting estrogen-dependent cancer comprising administering to a patient in need of such treatment an effective amount of a compound of the formula

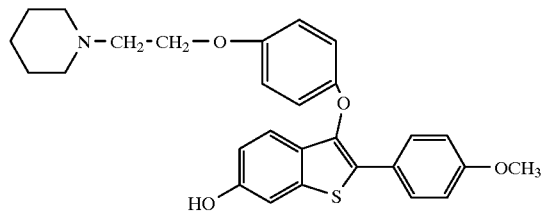

or a pharmaceutically acceptable salt thereof; together with a progestin selected from progesterone, norethylnodrel, nongestrel, megestrol acetate and norethindrone.

9. The method of claim 8 wherein said compound is the hydrochloride salt thereof.

10. A method according to claim 8 wherein said estrogen-dependent cancer is breast cancer.

11. The method of claim 10 wherein said compound is the hydrochloride salt thereof.

* * * * *